(12) United States Patent
Takahashi et al.

(10) Patent No.: US 8,716,451 B2
(45) Date of Patent: May 6, 2014

(54) STABILIZED HUMAN IGG2 AND IGG3 ANTIBODIES

(75) Inventors: Nobuaki Takahashi, Gunma (JP); Hideaki Yoshida, Gunma (JP)

(73) Assignee: Kyowa Hakko Kirin Co., Ltd, Tokyo (JP)

(*) Notice: Subject to any disclaimer, the term of this patent is extended or adjusted under 35 U.S.C. 154(b) by 1326 days.

(21) Appl. No.: 11/794,950

(22) PCT Filed: Jan. 12, 2006

(86) PCT No.: PCT/JP2006/300307
§ 371 (c)(1),
(2), (4) Date: Jul. 10, 2007

(87) PCT Pub. No.: WO2006/075668
PCT Pub. Date: Jul. 20, 2006

(65) Prior Publication Data
US 2008/0138335 A1 Jun. 12, 2008

(30) Foreign Application Priority Data
Jan. 12, 2005 (JP) ................. 2005-005794

(51) Int. Cl.
*C07K 16/00* (2006.01)
*C12N 15/00* (2006.01)

(52) U.S. Cl.
USPC ............... 530/387.3; 530/387.1; 435/69.6

(58) Field of Classification Search
None
See application file for complete search history.

(56) References Cited

U.S. PATENT DOCUMENTS

| | | | |
|---|---|---|---|
| 2003/0059472 A1 | 3/2003 | Brynjelsen et al. | |
| 2004/0002587 A1* | 1/2004 | Watkins et al. | 530/388.15 |
| 2004/0191265 A1 | 9/2004 | Schenerman et al. | |
| 2006/0134105 A1* | 6/2006 | Lazar et al. | 424/133.1 |
| 2007/0148163 A1 | 6/2007 | Takahashi et al. | |

FOREIGN PATENT DOCUMENTS

| | | |
|---|---|---|
| EP | 1 391 464 A1 | 2/2004 |
| EP | 1 707 627 A1 | 12/2004 |
| EP | 1 810 979 A1 | 7/2007 |
| WO | WO 02/088186 A1 | 11/2002 |
| WO | WO 03/040170 A2 | 5/2003 |
| WO | WO 2005/063981 A1 | 7/2005 |
| WO | WO 2005/092925 A2 | 10/2005 |

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Supplementary European Search Report EP 06 70 2685.
Mi-Huan Tao et al., "Structural Features of Human Immunoglobulin G that Determine Isotype-specific Differences in Complement Activation", Journal of Experimental Medicine, Tokyo JP, vol. 178, No. 2, Aug. 1, 1993, pp. 661-667.
Chappel M S et al: "Identification of the Fc γ receptor class I binding site in human IgG through the use of recombinant IgG1/IgG2 hybrid and point-mutated antibodies" Proceedings of the National Academy of Sciences of the United States (PNAS), National Academy of Science, vol. 88, No. 20, Oct. 1, 1991, pp. 9036-9040, XP002392092 ISSN: 0027-8424.
Little M et al: "Of mice and men: hybridoma and recombinant antibodies "Immunology Today, Elsevier Publications, Cambridge, GB, vol. 21, No. 8, Aug. 1, 2000, pp. 364-370, XP004215163 ISSN: 0167-5699.
Communication dated Jun. 18, 2010, from the European Patent Office issued in counterpart European Application No. 06702685.6-2405.
Chappel, M. Suzanne, et al., "Identification of a Secondary FcγRI Binding Site within a Genetically Engineered Human IgG Antibody" The Journal of Biological Chemistry (1993) pp. 25124-25131, vol. 268, No. 33.
Idusogie Esohe E, et al., "Mapping of the C1q Binding Site on Rituxan, a Chimeric Antibody with a Hunan IgG1 Fe" The Journal of Immunology (2000) pp. 4178-4184, vol. 164.
Japanese Office Action dated Jun. 7, 2011 issued in corresponding Japanese Patent Application No. 2006-552966.

* cited by examiner

*Primary Examiner* — Sharon Wen
(74) *Attorney, Agent, or Firm* — Sughrue Mion, PLLC

(57) ABSTRACT

It is intended to provide highly stable variants of human antibody IgG2 and IgG3 subclasses. The present invention provides an IgG heavy chain comprising the constant region of a human IgG2 heavy chain having at least a substitution of Y for F at the 300th position, L for V at the 309th position, or A for T at the 339th position designated by the EU index of Kabat et al. and an IgG heavy chain comprising the constant region of a human IgG3 heavy chain having at least a substitution of K for N at the 392nd position or V for M at the 397th position designated by the EU index of Kabat et al. The present invention also provides monoclonal antibodies comprising these heavy chains.

20 Claims, 8 Drawing Sheets

```
                         SEQUENCE LISTING

<160> NUMBER OF SEQ ID NOS: 88

<210> SEQ ID NO 1
<211> LENGTH: 1480
<212> TYPE: DNA
<213> ORGANISM: Homo sapiens

<400> SEQUENCE: 1
gtcgacgctg aattctggct gaccagggca gccaccagag ctccagacaa tgtctgtctc    60
cttcctcatc ttcctgcccg tgctgggcct cccatggggt gtcctgtcac aggtccaact   120
gcagcagtca ggtccaggac tggtgaagcc ctcgcagacc ctctcactca cctgtgccat   180
ctccggggac agtgtctcta gcaacagtgc tacttggaac tggatcaggc agtccccatc   240
```

```
gagagacctt gagtggctgg gaaggacata ctacaggtcc aagtggtatc gtgattatgt   300
aggatctgtg aaaagtcgaa taatcatcaa cccagacaca tccaacaacc agttctccct   360
gcagctgaac tctgtgactc ccgaggacac ggctatatat tactgtacaa gagcacagtg   420
gctgggaggg gattacccct actactacag tatggacgtc tggggccaag gaccacggt    480
caccgtctct tcagcctcca ccaagggccc atcggtcttc ccctggcgc cctgctccag    540
gagcacctcc gagagcacag cggccctggg ctgcctggtc aaggactact tccccgaacc   600
ggtgacggtg tcgtggaact caggcgctct gaccagcggc gtgcacacct tcccagctgt   660
cctacagtcc tcaggactct actccctcag cagcgtggtg accgtgccct ccagcaactt   720
cggcacccag acctacacct gcaacgtaga tcacaagccc agcaacacca aggtggacaa   780
gacagttgag cgcaaatgtt gtgtcgagtg cccaccgtgc ccagcaccac ctgtggcagg   840
accgtcagtc ttcctcttcc ccccaaaacc caaggacacc ctcatgatct cccggacccc   900
tgaggtcacg tgcgtggtgg tggacgtgag ccacgaagac cccgaggtcc agttcaactg   960
gtacgtggac ggcgtggagg tgcataatgc caagacaaag ccacgggagg agcagttcaa  1020
cagcacgttc cgtgtggtca gcgtcctcac cgttgtgcac caggactggc tgaacggcaa  1080
ggagtacaag tgcaaggtct ccaacaaagg cctcccagcc cccatcgaga aaaccatctc  1140
caaaaccaaa gggcagcccc gagaaccaca ggtgtacacc ctgccccat cccgggagga   1200
gatgaccaag aaccaggtca gcctgacctg cctggtcaaa ggcttctacc ccagcgacat  1260
cgccgtggag tgggagagca atgggcagcc ggagaacaac tacaagacca cacctcccat  1320
gctggactca gacggctcct tcttcctcta cagcaagctc accgtggaca gagcaggtg   1380
gcagcagggg aacgtcttct catgctccgt gatgcatgag gctctgcaca accactacac  1440
gcagaagagc ctctccctgt ctccgggtaa atgaggatcc                         1480
```

<210> SEQ ID NO 2
<211> LENGTH: 474
<212> TYPE: PRT
<213> ORGANISM: Homo sapiens

<400> SEQUENCE: 2

```
Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Thr Trp Asn Trp Ile Arg Gln Ser Pro Ser
    50                  55                  60

Arg Asp Leu Glu Trp Leu Gly Arg Thr Tyr Tyr Arg Ser Lys Trp Tyr
65                  70                  75                  80

Arg Asp Tyr Val Gly Ser Val Lys Ser Arg Ile Ile Ile Asn Pro Asp
                85                  90                  95

Thr Ser Asn Asn Gln Phe Ser Leu Gln Leu Asn Ser Val Thr Pro Glu
            100                 105                 110

Asp Thr Ala Ile Tyr Tyr Cys Thr Arg Ala Gln Trp Leu Gly Gly Asp
        115                 120                 125

Tyr Pro Tyr Tyr Tyr Ser Met Asp Val Trp Gly Gln Gly Thr Thr Val
    130                 135                 140

Thr Val Ser Ser Ala Ser Thr Lys Gly Pro Ser Val Phe Pro Leu Ala
145                 150                 155                 160
```

```
Pro Cys Ser Arg Ser Thr Ser Glu Ser Thr Ala Ala Leu Gly Cys Leu
            165                 170                 175

Val Lys Asp Tyr Phe Pro Glu Pro Val Thr Val Ser Trp Asn Ser Gly
        180                 185                 190

Ala Leu Thr Ser Gly Val His Thr Phe Pro Ala Val Leu Gln Ser Ser
    195                 200                 205

Gly Leu Tyr Ser Leu Ser Ser Val Val Thr Val Pro Ser Ser Asn Phe
210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350

Lys Gly Leu Pro Ala Pro Ile Glu Lys Thr Ile Ser Lys Thr Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 3
<211> LENGTH: 406
<212> TYPE: DNA
<213> ORGANISM: Homo sapiens

<400> SEQUENCE: 3
actgctcagt taggacccag agggaaccat ggaagcccca gctcagcttc tcttcctcct      60
gctactctgg ctcccagata ccaccggaga aattgtgttg acacagtctc cagccaccct     120
gtctttgtct ccaggggaaa gagccaccct ctcctgcagg gccagtcaga gtgttagcag     180
ctacttagcc tggtaccaac agaaacctgg ccaggctccc aggctcctca tctatgatgc     240
atccaacagg gccactggca tcccagccag gttcagtggc agtgggtctg ggacagactt     300
cactctcacc atcagcagcc tagagcctga agattttgca gtttattact gtcagcagcg     360
```
tagcaacact tcggccctg ggaccaaagt ggatatcaaa cgtacg    406

<210> SEQ ID NO 4
<211> LENGTH: 126
<212> TYPE: PRT
<213> ORGANISM: Homo sapiens

<400> SEQUENCE: 4

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Thr Phe Gly Pro Gly Thr Lys Val Asp Ile Lys Arg Thr
        115                 120                 125

<210> SEQ ID NO 5
<211> LENGTH: 508
<212> TYPE: DNA
<213> ORGANISM: Homo sapiens

<400> SEQUENCE: 5
ctgaacacag acccgtcgac tcccaggtgt ttccattcag tgatcagcac tgaacacaga    60
ggactcacca tggagttggg actgagctgg attttccttt ggctattttt aaaaggtgtc    120
cagtgtgaag tgcagctggt ggagtctggg ggaggcttgg tacagcctgg caggtccctg    180
agactctcct gtgcagcctc tggattcacc tttgatgatt atgccatgca ctgggtccgg    240
caagctccag ggaagggcct ggagtgggtc tcaggtatta gttggaatag tggtagcttg    300
gtgcatgcgg actctgtgaa gggccgattc accatctcca gagacaacgc caagaactcc    360
ctgtatctgc aaatgaacag tctgagagct gaggacacgg ccttgtatta ctgtgcaaga    420
gataggctat ttcggggagt taggtactac ggtatggacg tctggggcca agggaccacg    480
gtcaccgtct cctcagctag caccaagg    508

<210> SEQ ID NO 6
<211> LENGTH: 146
<212> TYPE: PRT
<213> ORGANISM: Homo sapiens

<400> SEQUENCE: 6

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Gly Ile Ser Trp Asn Ser Gly Ser Leu Val His Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Arg Leu Phe Arg Gly Val Arg Tyr Tyr Gly
        115                 120                 125

Met Asp Val Trp Gly Gln Gly Thr Thr Val Thr Val Ser Ser Ala Ser
    130                 135                 140

Thr Lys
145

<210> SEQ ID NO 7
<211> LENGTH: 414
<212> TYPE: DNA
<213> ORGANISM: Homo sapiens

<400> SEQUENCE: 7
ctgctcagtt aggacccaga gggaaccatg gaagcccag ctcagcttct cttcctcctg    60
ctactctggc tcccagatac caccggagaa attgtgttga cacagtctcc agccaccctg   120
tctttgtctc caggggaaag agccaccctc tcctgcaggg ccagtcagag tgttagcagc   180
tacttagcct ggtaccaaca gaaacctggc caggctccca ggctcctcat ctatgatgca   240
tccaacaggg ccactggcat cccagccagg ttcagtggca gtgggtctgg gacagacttc   300
actctcacca tcagcagcct agagcctgaa gattttgcag tttattactg tcagcagcgt   360
agccactggc tcactttcgg cggggggacc aaggtggaga tcaaacgtac ggtg         414

<210> SEQ ID NO 8
<211> LENGTH: 129
<212> TYPE: PRT
<213> ORGANISM: Homo sapiens

<400> SEQUENCE: 8

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

His Trp Leu Thr Phe Gly Gly Gly Thr Lys Val Glu Ile Lys Arg Thr
        115                 120                 125

Val

<210> SEQ ID NO 9
<211> LENGTH: 27
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 9
gggtacgtcc tcacattcag tgatcag                                              27

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggggtccgg gagatcatga gagtgtcctt                                           30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaggacactc tcatgatctc ccggacccct                                           30

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgatcatacg tagatatcac ggc                                                  23

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggtgtacacc tgtggctctc ggggctgccc                                           30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggcagcccc gagagccaca ggtgtacacc                                           30

<210> SEQ ID NO 15
<211> LENGTH: 1425
<212> TYPE: DNA
<213> ORGANISM: Homo sapiens

<400> SEQUENCE: 15
```

```
atgtctgtct ccttcctcat cttcctgccc gtgctgggcc tcccatgggg tgtcctgtca    60
caggtccaac tgcagcagtc aggtccagga ctggtgaagc cctcgcagac cctctcactc   120
acctgtgcca tctccgggga cagtgtctct agcaacagtg ctacttggaa ctggatcagg   180
cagtccccat cgagagacct tgagtggctg gaaggacat actacaggtc caagtggtat    240
cgtgattatg taggatctgt gaaaagtcga ataatcatca acccagacac atccaacaac   300
cagttctccc tgcagctgaa ctctgtgact cccgaggaca cggctatata ttactgtaca   360
agagcacagt ggctgggagg ggattacccc tactactaca gtatggacgt ctggggccaa   420
gggaccacgg tcaccgtctc ctcagctagc accaagggcc catcggtctt ccccctggcg   480
ccctgctcca ggagcacctc cgagagcaca gcggccctgg gctgcctggt caaggactac   540
ttccccgaac cggtgacggt gtcgtggaac tcaggcgctc tgaccagcgg cgtgcacacc   600
ttcccagctg tcctacagtc ctcaggactc tactccctca gcagcgtggt gaccgtgccc   660
tccagcaact tcggcaccca gacctacacc tgcaacgtag atcacaagcc cagcaacacc   720
aaggtggaca agacagttga gcgcaaatgt tgtgtcgagt gcccaccgtg cccagcacca   780
cctgtggcag gaccgtcagt cttcctcttc cccccaaaac ccaaggacac cctcatgatc   840
tcccggaccc ctgaggtcac gtgcgtggtg gtggacgtga gccacgaaga cccgaggtc    900
cagttcaact ggtacgtgga cggcgtggag gtgcataatg ccaagacaaa gccacgggag   960
gagcagttca acagcacgtt ccgtgtggtc agcgtcctca ccgttgtgca ccaggactgg  1020
ctgaacggca aggagtacaa gtgcaaggtc tccaacaaag gcctcccagc tcccatcgag  1080
aaaaccatct ccaaaaccaa agggcagccc cgagaaccac aggtgtacac cctgccccca  1140
tcccgggagg agatgaccaa gaaccaggtc agcctgacct gcctggtcaa aggcttctac  1200
cccagcgaca tcgccgtgga gtgggagagc aatgggcagc cggagaacaa ctacaagacc  1260
acacctccca tgctggactc cgacggctcc ttcttcctct acagcaagct caccgtggac  1320
aagagcaggt ggcagcaggg gaacgtcttc tcatgctccg tgatgcatga ggctctgcac  1380
aaccactaca cgcagaagag cctctccctg tctccgggta aatga              1425
```

<210> SEQ ID NO 16
<211> LENGTH: 474
<212> TYPE: PRT
<213> ORGANISM: Homo sapiens

<400> SEQUENCE: 16

```
Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Thr Trp Asn Trp Ile Arg Gln Ser Pro Ser
    50                  55                  60

Arg Asp Leu Glu Trp Leu Gly Arg Thr Tyr Tyr Arg Ser Lys Trp Tyr
65                  70                  75                  80

Arg Asp Tyr Val Gly Ser Val Lys Ser Arg Ile Ile Ile Asn Pro Asp
                85                  90                  95

Thr Ser Asn Asn Gln Phe Ser Leu Gln Leu Asn Ser Val Thr Pro Glu
            100                 105                 110

Asp Thr Ala Ile Tyr Tyr Cys Thr Arg Ala Gln Trp Leu Gly Gly Asp
        115                 120                 125
```

```
Tyr Pro Tyr Tyr Tyr Ser Met Asp Val Trp Gly Gln Gly Thr Thr Val
            130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Gln Phe Asn Trp
290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350

Lys Gly Leu Pro Ala Ser Ile Glu Lys Thr Ile Ser Lys Thr Lys Gly
        355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 17
<211> LENGTH: 696
<212> TYPE: DNA
<213> ORGANISM: Homo sapiens

<400> SEQUENCE: 17
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
```

| | | | | |
|---|---|---|---|---|
| ggccaggctc | ccaggctcct | catctatgat | gcatccaaca | gggccactgg | catcccagcc | 240 |
| aggttcagtg | gcagtgggtc | tgggacagac | ttcactctca | ccatcagcag | cctagagcct | 300 |
| gaagattttg | cagtttatta | ctgtcagcag | cgtagcaaca | ctttcggccc | tgggaccaaa | 360 |
| gtggatatca | aacgtacggt | ggctgcacca | tctgtcttca | tcttcccgcc | atctgatgag | 420 |
| cagttgaaat | ctggaactgc | ctctgttgtg | tgcctgctga | ataacttcta | tcccagagag | 480 |
| gccaaagtac | agtggaaggt | ggataacgcc | ctccaatcgg | gtaactccca | ggagagtgtc | 540 |
| acagagcagg | acagcaagga | cagcacctac | agcctcagca | gcaccctgac | gctgagcaaa | 600 |
| gcagactacg | agaaacacaa | agtctacgcc | tgcgaagtca | cccatcaggg | cctgagctcg | 660 |
| cccgtcacaa | agagcttcaa | caggggagag | tgttga | | | 696 |

<210> SEQ ID NO 18
<211> LENGTH: 231
<212> TYPE: PRT
<213> ORGANISM: Homo sapiens

<400> SEQUENCE: 18

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Thr Phe Gly Pro Gly Thr Lys Val Asp Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230

<210> SEQ ID NO 19
<211> LENGTH: 1407
<212> TYPE: DNA
<213> ORGANISM: Homo sapiens

<400> SEQUENCE: 19

| | | | | | |
|---|---|---|---|---|---|
| atggagttgg | gactgagctg | gattttcctt | ttggctattt | taaaaggtgt | ccagtgtgaa | 60 |

-continued

```
gtgcagctgg tggagtctgg gggaggcttg gtacagcctg gcaggtccct gagactctcc    120
tgtgcagcct ctggattcac ctttgatgat tatgccatgc actgggtccg gcaagctcca    180
gggaagggcc tggagtgggt ctcaggtatt agttggaata gtggtagctt ggtgcatgcg    240
gactctgtga agggccgatt caccatctcc agagacaacg ccaagaactc cctgtatctg    300
caaatgaaca gtctgagagc tgaggacacg gccttgtatt actgtgcaag agataggcta    360
tttcggggag ttaggtacta cggtatggac gtctggggcc aagggaccac ggtcaccgtc    420
tcctcagcta gcaccaaggg cccatcggtc ttccccctgg cgccctgctc caggagcacc    480
tccgagagca cagcggccct gggctgcctg gtcaaggact acttccccga accggtgacg    540
gtgtcgtgga actcaggcgc tctgaccagc ggcgtgcaca ccttcccagc tgtcctacag    600
tcctcaggac tctactccct cagcagcgtg gtgaccgtgc cctccagcaa cttcggcacc    660
cagacctaca cctgcaacgt agatcacaag cccagcaaca ccaaggtgga caagacagtt    720
gagcgcaaat gttgtgtcga gtgcccaccg tgcccagcac cacctgtggc aggaccgtca    780
gtcttcctct tccccccaaa acccaaggac accctcatga tctcccggac ccctgaggtc    840
acgtgcgtgg tggtggacgt gagccacgaa gaccccgagg tccagttcaa ctggtacgtg    900
gacggcgtgg aggtgcataa tgccaagaca aagccacggg aggagcagtt caacagcacg    960
ttccgtgtgg tcagcgtcct caccgttgtg caccaggact ggctgaacgg caaggagtac   1020
aagtgcaagg tctccaacaa aggcctccca gcctccatcg agaaaaccat ctccaaaacc   1080
aaagggcagc cccgagaacc acaggtgtac accctgcccc catcccggga ggagatgacc   1140
aagaaccagg tcagcctgac ctgcctggtc aaaggcttct accccagcga catcgccgtg   1200
gagtgggaga gcaatgggca gccggagaac aactacaaga ccacacctcc catgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                       1407
```

<210> SEQ ID NO 20
<211> LENGTH: 468
<212> TYPE: PRT
<213> ORGANISM: Homo sapiens

<400> SEQUENCE: 20

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Gly Ile Ser Trp Asn Ser Gly Ser Leu Val His Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Arg Leu Phe Arg Gly Val Arg Tyr Tyr Gly
        115                 120                 125

Met Asp Val Trp Gly Gln Gly Thr Thr Val Thr Val Ser Ser Ala Ser
```

| | | | | | | | | | | | | |
|---|---|---|---|---|---|---|---|---|---|---|---|---|
| | | 130 | | | | 135 | | | | 140 | | |
| Thr | Lys | Gly | Pro | Ser | Val | Phe | Pro | Leu | Ala | Pro | Cys | Ser | Arg | Ser | Thr |
| 145 | | | | 150 | | | | 155 | | | | 160 |
| Ser | Glu | Ser | Thr | Ala | Ala | Leu | Gly | Cys | Leu | Val | Lys | Asp | Tyr | Phe | Pro |
| | | | 165 | | | | 170 | | | | 175 | |
| Glu | Pro | Val | Thr | Val | Ser | Trp | Asn | Ser | Gly | Ala | Leu | Thr | Ser | Gly | Val |
| | | | 180 | | | | 185 | | | | 190 | |
| His | Thr | Phe | Pro | Ala | Val | Leu | Gln | Ser | Ser | Gly | Leu | Tyr | Ser | Leu | Ser |
| | | 195 | | | | 200 | | | | 205 | | |
| Ser | Val | Val | Thr | Val | Pro | Ser | Ser | Asn | Phe | Gly | Thr | Gln | Thr | Tyr | Thr |
| | 210 | | | | 215 | | | | 220 | | | |
| Cys | Asn | Val | Asp | His | Lys | Pro | Ser | Asn | Thr | Lys | Val | Asp | Lys | Thr | Val |
| 225 | | | | 230 | | | | 235 | | | | 240 |
| Glu | Arg | Lys | Cys | Cys | Val | Glu | Cys | Pro | Pro | Cys | Pro | Ala | Pro | Pro | Val |
| | | | 245 | | | | 250 | | | | 255 | |
| Ala | Gly | Pro | Ser | Val | Phe | Leu | Phe | Pro | Pro | Lys | Pro | Lys | Asp | Thr | Leu |
| | | | 260 | | | | 265 | | | | 270 | |
| Met | Ile | Ser | Arg | Thr | Pro | Glu | Val | Thr | Cys | Val | Val | Val | Asp | Val | Ser |
| | | 275 | | | | 280 | | | | 285 | | |
| His | Glu | Asp | Pro | Glu | Val | Gln | Phe | Asn | Trp | Tyr | Val | Asp | Gly | Val | Glu |
| | 290 | | | | 295 | | | | 300 | | | |
| Val | His | Asn | Ala | Lys | Thr | Lys | Pro | Arg | Glu | Glu | Gln | Phe | Asn | Ser | Thr |
| 305 | | | | 310 | | | | 315 | | | | 320 |
| Phe | Arg | Val | Val | Ser | Val | Leu | Thr | Val | Val | His | Gln | Asp | Trp | Leu | Asn |
| | | | 325 | | | | 330 | | | | 335 | |
| Gly | Lys | Glu | Tyr | Lys | Cys | Lys | Val | Ser | Asn | Lys | Gly | Leu | Pro | Ala | Ser |
| | | | 340 | | | | 345 | | | | 350 | |
| Ile | Glu | Lys | Thr | Ile | Ser | Lys | Thr | Lys | Gly | Gln | Pro | Arg | Glu | Pro | Gln |
| | | 355 | | | | 360 | | | | 365 | | |
| Val | Tyr | Thr | Leu | Pro | Pro | Ser | Arg | Glu | Glu | Met | Thr | Lys | Asn | Gln | Val |
| | 370 | | | | 375 | | | | 380 | | | |
| Ser | Leu | Thr | Cys | Leu | Val | Lys | Gly | Phe | Tyr | Pro | Ser | Asp | Ile | Ala | Val |
| 385 | | | | 390 | | | | 395 | | | | 400 |
| Glu | Trp | Glu | Ser | Asn | Gly | Gln | Pro | Glu | Asn | Asn | Tyr | Lys | Thr | Thr | Pro |
| | | | 405 | | | | 410 | | | | 415 | |
| Pro | Met | Leu | Asp | Ser | Asp | Gly | Ser | Phe | Phe | Leu | Tyr | Ser | Lys | Leu | Thr |
| | | | 420 | | | | 425 | | | | 430 | |
| Val | Asp | Lys | Ser | Arg | Trp | Gln | Gln | Gly | Asn | Val | Phe | Ser | Cys | Ser | Val |
| | | 435 | | | | 440 | | | | 445 | | |
| Met | His | Glu | Ala | Leu | His | Asn | His | Tyr | Thr | Gln | Lys | Ser | Leu | Ser | Leu |
| | 450 | | | | 455 | | | | 460 | | | |
| Ser | Pro | Gly | Lys |
| 465 | | | |

```
<210> SEQ ID NO 21
<211> LENGTH: 702
<212> TYPE: DNA
<213> ORGANISM: Homo sapiens

<400> SEQUENCE: 21
atggaagccc cagctcagct tctcttcctc ctgctactct ggctcccaga taccaccgga      60
gaaattgtgt tgacacagtc tccagccacc ctgtctttgt ctccagggga aagagccacc    120
ctctcctgca gggccagtca gagtgttagc agctacttag cctggtacca acagaaacct    180
ggccaggctc ccaggctcct catctatgat gcatccaaca gggccactgg catcccagcc    240
```

```
aggttcagtg gcagtgggtc tgggacagac ttcactctca ccatcagcag cctagagcct    300
gaagattttg cagtttatta ctgtcagcag cgtagccact ggctcacttt cggcggggggg   360 accaaggtgg agatcaaacg tacggtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag     540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ga                      702
```

<210> SEQ ID NO 22
<211> LENGTH: 233
<212> TYPE: PRT
<213> ORGANISM: Homo sapiens

<400> SEQUENCE: 22

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

His Trp Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agaccccgag gtcaagttca actggtacgt g                          31

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgggaggagc agtacaacag cacgttcc                              28

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agttcaacag cacgtaccgt gtggtcagc                             29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcgtcctcac cgttctgcac caggactgg                             29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aggtctccaa caaagccctc ccagcctcc                             29

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaaaaccatc tccaaagcca aagggcagcc c                          31

<210> SEQ ID NO 29
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agttcaacag cacgtaccgt gtggtcagcg tcctcaccgt tctgcaccag gactgg     56

<210> SEQ ID NO 30
<211> LENGTH: 1425
<212> TYPE: DNA
<213> ORGANISM: Homo sapiens

<400> SEQUENCE: 30

```
atgtctgtct ccttcctcat cttcctgccc gtgctgggcc tcccatgggg tgtcctgtca      60
caggtccaac tgcagcagtc aggtccagga ctggtgaagc cctcgcagac cctctcactc     120
acctgtgcca tctccgggga cagtgtctct agcaacagtg ctacttggaa ctggatcagg     180
cagtccccat cgagagacct tgagtggctg gaaggacat actacaggtc caagtggtat      240
cgtgattatg taggatctgt gaaaagtcga ataatcatca cccgagacac atccaacaac     300
cagttctccc tgcagctgaa ctctgtgact cccgaggaca cggctatata ttactgtaca     360
agagcacagt ggctgggagg ggattacccc tactactaca gtatggacgt ctggggccaa     420
gggaccacgg tcaccgtctc ctcagctagc accaagggcc catcggtctt ccccctggcg     480
ccctgctcca ggagcaccte cgagagcaca gcggccctgg gctgcctggt caaggactac     540
ttccccgaac cggtgacggt gtcgtggaac tcaggcgctc tgaccagcgg cgtgcacacc     600
ttcccagctg tcctacagtc ctcaggactc tactccctca gcagcgtggt gaccgtgccc     660
tccagcaact tcggcaccca gacctacacc tgcaacgtag atcacaagcc cagcaacacc     720
aaggtggaca agacagttga gcgcaaatgt tgtgtcgagt gcccaccgtg cccagcacca     780
cctgtggcag accgtcagt cttcctcttc cccccaaaac ccaaggacac cctcatgatc     840
tcccggaccc ctgaggtcac gtgcgtggtg gtggacgtga gccacgaaga ccccgaggtc     900
cagttcaact ggtacgtgga cggcgtggag gtgcataatg ccaagacaaa gccacgggag     960
gagcagttca acagcacgta ccgtgtggtc agcgtcctca ccgttctgca ccaggactgg    1020
ctgaacggca aggagtacaa gtgcaaggtc tccaacaaag gcctcccagc tcccatcgag    1080
aaaaccatct ccaaagccaa agggcagccc cgagaaccac aggtgtacac cctgcccca     1140
tcccgggagg agatgaccaa gaaccaggtc agcctgacct gcctggtcaa aggcttctac    1200
cccagcgaca tcgccgtgga gtgggagagc aatgggcagc cggagaacaa ctacaagacc    1260
acacctccca tgctggactc cgacggctcc ttcttcctct acagcaagct caccgtggac    1320
aagagcaggt ggcagcaggg gaacgtcttc tcatgctccg tgatgcatga ggctctgcac    1380
aaccactaca cgcagaagag cctctccctg tctccgggta atga                     1425
```

<210> SEQ ID NO 31
<211> LENGTH: 474
<212> TYPE: PRT
<213> ORGANISM: Homo sapiens

<400> SEQUENCE: 31

```
Met Ser Val Ser Phe Leu Ile Phe Leu Pro Val Leu Gly Leu Pro Trp
  1               5                  10                  15

Gly Val Leu Ser Gln Val Gln Leu Gln Gln Ser Gly Pro Gly Leu Val
             20                  25                  30

Lys Pro Ser Gln Thr Leu Ser Leu Thr Cys Ala Ile Ser Gly Asp Ser
         35                  40                  45

Val Ser Ser Asn Ser Ala Thr Trp Asn Trp Ile Arg Gln Ser Pro Ser
     50                  55                  60

Arg Asp Leu Glu Trp Leu Gly Arg Thr Tyr Tyr Arg Ser Lys Trp Tyr
 65                  70                  75                  80
```

```
Arg Asp Tyr Val Gly Ser Val Lys Ser Arg Ile Ile Asn Pro Asp
             85                  90                  95

Thr Ser Asn Asn Gln Phe Ser Leu Gln Leu Asn Ser Val Thr Pro Glu
        100                 105                 110

Asp Thr Ala Ile Tyr Tyr Cys Thr Arg Ala Gln Trp Leu Gly Gly Asp
        115                 120                 125

Tyr Pro Tyr Tyr Tyr Ser Met Asp Val Trp Gly Gln Gly Thr Thr Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ala Ser Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 32
<211> LENGTH: 696
<212> TYPE: DNA
<213> ORGANISM: Homo sapiens
```

<400> SEQUENCE: 32

```
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaaca cttttcggcc ctgggaccaaa    360
gtggatatca aacgtacggt ggctgcacca tctgtcttca tcttcccgcc atctgatgag     420
cagttgaaat ctggaactgc ctctgttgtg tgcctgctga ataacttcta tcccagagag     480
gccaaagtac agtggaaggt ggataacgcc ctccaatcgg gtaactccca ggagagtgtc     540
acagagcagg acagcaagga cagcacctac agcctcagca gcaccctgac gctgagcaaa     600
gcagactacg agaaacacaa agtctacgcc tgcgaagtca cccatcaggg cctgagctcg     660
cccgtcacaa agagcttcaa caggggagag tgttga                               696
```

<210> SEQ ID NO 33
<211> LENGTH: 231
<212> TYPE: PRT
<213> ORGANISM: Homo sapiens

<400> SEQUENCE: 33

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Thr Phe Gly Pro Gly Thr Lys Val Asp Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230
```

<210> SEQ ID NO 34
<211> LENGTH: 1407
<212> TYPE: DNA
<213> ORGANISM: Homo sapiens

<400> SEQUENCE: 34

```
atggagttgg gactgagctg gattttcctt ttggctattt taaaaggtgt ccagtgtgaa      60
gtgcagctgg tggagtctgg gggaggcttg gtacagcctg gcaggtccct gagactctcc     120
tgtgcagcct ctggattcac ctttgatgat tatgccatgc actgggtccg gcaagctcca     180
gggaagggcc tggagtgggt ctcaggtatt agttggaata gtggtagctt ggtgcatgcg     240
gactctgtga agggccgatt caccatctcc agagacaacg ccaagaactc cctgtatctg     300
caaatgaaca gtctgagagc tgaggacacg gccttgtatt actgtgcaag agataggcta     360
tttcggggag ttaggtacta cggtatggac gtctggggcc aagggaccac ggtcaccgtc     420
tcctcagcta gcaccaaggg cccatcggtc ttccccctgg cgccctgctc caggagcacc     480
tccgagagca cagcggccct gggctgcctg gtcaaggact acttccccga accggtgacg     540
gtgtcgtgga actcaggcgc tctgaccagc ggcgtgcaca ccttcccagc tgtcctacag     600
tcctcaggac tctactccct cagcagcgtg gtgaccgtgc cctccagcaa cttcggcacc     660
cagacctaca cctgcaacgt agatcacaag cccagcaaca ccaaggtgga caagacagtt     720
gagcgcaaat gttgtgtcga gtgcccaccg tgcccagcac acctgtggc aggaccgtca     780
gtcttcctct tccccccaaa acccaaggac accctcatga tctcccggac ccctgaggtc     840
acgtgcgtgg tggtggacgt gagccacgaa gaccccgagg tccagttcaa ctggtacgtg     900
gacggcgtgg aggtgcataa tgccaagaca aagccacggg aggagcagtt caacagcacg     960
taccgtgtgg tcagcgtcct caccgttctg caccaggact ggctgaacgg caaggagtac    1020
aagtgcaagg tctccaacaa aggcctccca gcctccatcg agaaaaccat ctccaaagcc    1080
aaagggcagc cccgagaacc acaggtgtac accctgcccc catcccggga ggagatgacc    1140
aagaaccagg tcagcctgac ctgcctggtc aaaggcttct accccagcga catcgccgtg    1200
gagtgggaga gcaatgggca gccggagaac aactacaaga ccacacctcc catgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                        1407
```

<210> SEQ ID NO 35
<211> LENGTH: 468
<212> TYPE: PRT
<213> ORGANISM: Homo sapiens

<400> SEQUENCE: 35

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Asp Asp Tyr Ala Met His Trp Val Arg Gln Ala Pro Gly Lys Gly Leu
        50                  55                  60

Glu Trp Val Ser Gly Ile Ser Trp Asn Ser Gly Ser Leu Val His Ala
65                  70                  75                  80

Asp Ser Val Lys Gly Arg Phe Thr Ile Ser Arg Asp Asn Ala Lys Asn
```

```
                    85                  90                  95
Ser Leu Tyr Leu Gln Met Asn Ser Leu Arg Ala Glu Asp Thr Ala Leu
                100                 105                 110

Tyr Tyr Cys Ala Arg Asp Arg Leu Phe Arg Gly Val Arg Tyr Tyr Gly
            115                 120                 125

Met Asp Val Trp Gly Gln Gly Thr Thr Val Thr Val Ser Ser Ala Ser
        130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ala Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 36
<211> LENGTH: 702
<212> TYPE: DNA
<213> ORGANISM: Homo sapiens
```

<400> SEQUENCE: 36

```
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagccact ggctcacttt cggcggggg     360
accaaggtgg agatcaaacg tacggtggct gcaccatctg tcttcatctt cccgccatct     420
gatgagcagt tgaaatctgg aactgcctct gttgtgtgcc tgctgaataa cttctatccc     480
agagaggcca agtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ga                       702
```

<210> SEQ ID NO 37
<211> LENGTH: 233
<212> TYPE: PRT
<213> ORGANISM: Homo sapiens

<400> SEQUENCE: 37

```
Met Glu Ala Pro Ala Gln Leu Leu Phe Leu Leu Leu Leu Trp Leu Pro
 1               5                  10                  15

Asp Thr Thr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Gln Ser
         35                  40                  45

Val Ser Ser Tyr Leu Ala Trp Tyr Gln Gln Lys Pro Gly Gln Ala Pro
     50                  55                  60

Arg Leu Leu Ile Tyr Asp Ala Ser Asn Arg Ala Thr Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln Gln Arg Ser
            100                 105                 110

His Trp Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

-continued

<210> SEQ ID NO 38
<211> LENGTH: 462
<212> TYPE: DNA
<213> ORGANISM: Homo sapiens

<400> SEQUENCE: 38

```
atatgtcgac gagtcatgga tctcatgtgc aagaaaatga agcacctgtg gttcttcctc      60
ctgctggtgg cggctcccag atgggtcctg tcccagctgc agctgcagga gtcgggccca     120
ggactactga agccttcgga gaccctgtcc ctcacctgca ctgtctctgg cggctccatc     180
agcagtcctg gttactacgg gggctggatc cgccagcccc cagggaaggg gctggagtgg     240
attgggagta tctataaaag tgggagcacc taccacaacc cgtccctcaa gagtcgagtc     300
accatatccg tagacacgtc caagaaccag ttctccctga agctgagctc tgtgaccgcc     360
gcagacacgg ctgtgtatta ctgtacgaga cctgtagtac gatattttgg gtggttcgac     420
ccctggggcc aggaaccct ggtcaccgtc tcctcagcta gc                          462
```

<210> SEQ ID NO 39
<211> LENGTH: 149
<212> TYPE: PRT
<213> ORGANISM: Homo sapiens

<400> SEQUENCE: 39

```
Met Asp Leu Met Cys Lys Lys Met Lys His Leu Trp Phe Phe Leu Leu
1               5                  10                  15
Leu Val Ala Ala Pro Arg Trp Val Leu Ser Gln Leu Gln Leu Gln Glu
            20                  25                  30
Ser Gly Pro Gly Leu Leu Lys Pro Ser Glu Thr Leu Ser Leu Thr Cys
        35                  40                  45
Thr Val Ser Gly Gly Ser Ile Ser Ser Pro Gly Tyr Tyr Gly Gly Trp
    50                  55                  60
Ile Arg Gln Pro Pro Gly Lys Gly Leu Glu Trp Ile Gly Ser Ile Tyr
65                  70                  75                  80
Lys Ser Gly Ser Thr Tyr His Asn Pro Ser Leu Lys Ser Arg Val Thr
                85                  90                  95
Ile Ser Val Asp Thr Ser Lys Asn Gln Phe Ser Leu Lys Leu Ser Ser
            100                 105                 110
Val Thr Ala Ala Asp Thr Ala Val Tyr Tyr Cys Thr Arg Pro Val Val
        115                 120                 125
Arg Tyr Phe Gly Trp Phe Asp Pro Trp Gly Gln Gly Thr Leu Val Thr
    130                 135                 140
Val Ser Ser Ala Ser
145
```

<210> SEQ ID NO 40
<211> LENGTH: 448
<212> TYPE: DNA
<213> ORGANISM: Homo sapiens

<400> SEQUENCE: 40

```
agatcttaag caagtgtaac aactcagagt acgcggggag acccactcag gacacagcat      60
ggacatgagg gtccccgctc agctcctggg gcttctgctg ctctggctcc caggtgccag     120
atgtgccatc cagttgaccc agtctccatc ctccctgtct gcatctgtag gagacagagt     180
caccatcact tgccgggcaa gtcagggcat tagcagtgct ttagcctggt atcagcagaa     240
accagggaaa gctcctaagc tcctgatcta tgatgcctcc aatttggaaa gtggggtccc     300
atcaaggttc agcggcagtg gatctgggac agatttcact ctcaccatca gcagcctgca     360
```

```
gcctgaagat tttgcaactt attactgtca acagtttaat agttacccga cgttcggcca    420
agggaccaag gtggaaatca aacgtacg                                       448
```

<210> SEQ ID NO 41
<211> LENGTH: 130
<212> TYPE: PRT
<213> ORGANISM: Homo sapiens

<400> SEQUENCE: 41

```
Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Asn Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Thr Phe Gly Gln Gly Thr Lys Val Glu Ile Lys
        115                 120                 125

Arg Thr
    130
```

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
gtcttcgtgg ctcacgtcca ccaccacgca                                     30
```

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
tgcgtggtgg tggacgtgag ccacgaagac                                     30
```

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
cttggtcatc tcatcccggg atggggg                                        27
```

```
<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cccccatccc gggatgagat gaccaag                                           27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctggttcttg gtcagctcct cccggga                                           27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcccgggagg agctgaccaa gaaccag                                           27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gggaggcgtg gtcttgtagt tgttctc                                           27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gagaacaact acaagaccac gcctccc                                           27

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggagcatgag aagacgttcc cctgctg                                           27

<210> SEQ ID NO 51
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cagcagggga acgtcttctc atgctcc                                         27

<210> SEQ ID NO 52
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cccggatcct catttacccg gagacaggga gaggctcttc tgcgtgtagt ggttgtg        57

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
caccacgcct cccgtgctgg actccgac                                        28

<210> SEQ ID NO 54
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gggcagccgg agaacaacta caagaccacg cctcccgtgc tggactccga cggctcc        57

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cagtacaaca gcacgtaccg tgtggtcagc                                      30

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gaaaaccatc tccaaagcca aaggacagcc c                                    31

<210> SEQ ID NO 57
<211> LENGTH: 57
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 57
gggcagccgg agaacaacta caagaccacg cctcccgtgc tggactccga cggctcc        57

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cagtacaaca gcacgtaccg tgtggtcagc                                      30

<210> SEQ ID NO 59
<211> LENGTH: 1575
<212> TYPE: DNA
<213> ORGANISM: Homo sapiens

<400> SEQUENCE: 59
atggatctca tgtgcaagaa aatgaagcac ctgtggttct tcctcctgct ggtggcggct      60
cccagatggg tcctgtccca gctgcagctg caggagtcgg gcccaggact actgaagcct     120
tcggagaccc tgtccctcac ctgcactgtc tctggcggct ccatcagcag tcctggttac     180
tacgggggct ggatccgcca gccccaggg aaggggctgg agtggattgg agtatctat       240 aaaagtggga gcacctacca caacccgtcc ctcaagagtc gagtcaccat atccgtagac     300
acgtccaaga accagttctc cctgaagctg agctctgtga ccgccgcaga cacggctgtg     360
tattactgta cgagacctgt agtacgatat tttgggtggt cgacccctg gggccaggga     420 accctggtca ccgtctcctc agctagcacc aagggcccat cggtcttccc cctggcgccc     480
tgctccagga gcacctctgg gggcacagcg gccctgggct gcctggtcaa ggactacttc     540
cccgaaccgg tgacggtgtc gtggaactca ggcgccctga ccagcggcgt gcacaccttc     600
ccggctgtcc tacagtcctc aggactctac tccctcagca gcgtggtgac cgtgccctcc     660
agcagtttgg gcacccagac ctacacctgc aacgtgaatc acaagcccag caacaccaag     720
gtggacaaga gagttgagct caaaaccccca cttggtgaca aactcacac atgcccacgg      780 tgcccagagc ccaaatcttg tgacacacct ccccgtgcc cacggtgccc agagcccaaa     840
tcttgtgaca cacctccccc atgcccacgg tgcccagagc ccaaatcttg tgacacacct     900
cccccgtgcc caaggtgccc agcacctgaa ctcctgggag gaccgtcagt cttcctcttc     960
cccccaaaac ccaaggatac ccttatgatt tcccggaccc ctgaggtcac gtgcgtggtg    1020
gtggacgtga gccacgaaga cccgaggtc cagttcaagt ggtacgtgga cggcgtggag     1080
gtgcataatg ccaagacaaa gctgcgggag gagcagtaca acagcacgta ccgtgtggtc    1140
agcgtcctca ccgtcctgca ccaggactgg ctgaacggca aggagtacaa gtgcaaggtc    1200
tccaacaaag ccctcccagc ccccatcgag aaaaccatct ccaaaaccaa aggacagccc     1260
cgagaaccac aggtgtacac cctgccccca tcccgggagg agatgaccaa gaaccaggtc     1320
agcctgacct gcctggtcaa aggcttctac cccagcgaca tcgccgtgga gtgggagagc     1380
aatgggcagc cggagaacaa ctacaagacc acgcctcccg tgctggactc cgacggctcc     1440
ttcttcctct acagcaagct caccgtggac aagagcaggt ggcagcaggg gaacatcttc     1500
tcatgctccg tgatgcatga ggctctgcac aaccactaca cgcagaagag cctctccctg     1560
```

```
tctccgggta aatga                                            1575
```

<210> SEQ ID NO 60
<211> LENGTH: 524
<212> TYPE: PRT
<213> ORGANISM: Homo sapiens

<400> SEQUENCE: 60

```
Met Asp Leu Met Cys Lys Lys Met Lys His Leu Trp Phe Phe Leu Leu
1               5                   10                  15

Leu Val Ala Ala Pro Arg Trp Val Leu Ser Gln Leu Gln Leu Gln Glu
            20                  25                  30

Ser Gly Pro Gly Leu Leu Lys Pro Ser Glu Thr Leu Ser Leu Thr Cys
        35                  40                  45

Thr Val Ser Gly Gly Ser Ile Ser Ser Pro Gly Tyr Tyr Gly Gly Trp
    50                  55                  60

Ile Arg Gln Pro Pro Gly Lys Gly Leu Glu Trp Ile Gly Ser Ile Tyr
65                  70                  75                  80

Lys Ser Gly Ser Thr Tyr His Asn Pro Ser Leu Lys Ser Arg Val Thr
                85                  90                  95

Ile Ser Val Asp Thr Ser Lys Asn Gln Phe Ser Leu Lys Leu Ser Ser
            100                 105                 110

Val Thr Ala Ala Asp Thr Ala Val Tyr Tyr Cys Thr Arg Pro Val Val
        115                 120                 125

Arg Tyr Phe Gly Trp Phe Asp Pro Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Thr Cys Asn Val Asn His Lys Pro Ser Asn Thr Lys
225                 230                 235                 240

Val Asp Lys Arg Val Glu Leu Lys Thr Pro Leu Gly Asp Thr Thr His
                245                 250                 255

Thr Cys Pro Arg Cys Pro Glu Pro Lys Ser Cys Asp Thr Pro Pro Pro
            260                 265                 270

Cys Pro Arg Cys Pro Glu Pro Lys Ser Cys Asp Thr Pro Pro Cys
        275                 280                 285

Pro Arg Cys Pro Glu Pro Lys Ser Cys Asp Thr Pro Pro Cys Pro
    290                 295                 300

Arg Cys Pro Ala Pro Glu Leu Leu Gly Gly Pro Ser Val Phe Leu Phe
305                 310                 315                 320

Pro Pro Lys Pro Lys Asp Thr Leu Met Ile Ser Arg Thr Pro Glu Val
                325                 330                 335

Thr Cys Val Val Val Asp Val Ser His Glu Asp Pro Glu Val Gln Phe
            340                 345                 350

Lys Trp Tyr Val Asp Gly Val Glu Val His Asn Ala Lys Thr Lys Leu
        355                 360                 365
```

```
Arg Glu Glu Gln Tyr Asn Ser Thr Tyr Arg Val Val Ser Val Leu Thr
        370                 375                 380
Val Leu His Gln Asp Trp Leu Asn Gly Lys Glu Tyr Lys Cys Lys Val
385                 390                 395                 400
Ser Asn Lys Ala Leu Pro Ala Pro Ile Glu Lys Thr Ile Ser Lys Thr
                405                 410                 415
Lys Gly Gln Pro Arg Glu Pro Gln Val Tyr Thr Leu Pro Pro Ser Arg
            420                 425                 430
Glu Glu Met Thr Lys Asn Gln Val Ser Leu Thr Cys Leu Val Lys Gly
        435                 440                 445
Phe Tyr Pro Ser Asp Ile Ala Val Glu Trp Ser Asn Gly Gln Pro
    450                 455                 460
Glu Asn Asn Tyr Lys Thr Thr Pro Pro Val Leu Asp Ser Asp Gly Ser
465                 470                 475                 480
Phe Phe Leu Tyr Ser Lys Leu Thr Val Asp Lys Ser Arg Trp Gln Gln
                485                 490                 495
Gly Asn Ile Phe Ser Cys Ser Val Met His Glu Ala Leu His Asn His
            500                 505                 510
Tyr Thr Gln Lys Ser Leu Ser Leu Ser Pro Gly Lys
        515                 520
```

<210> SEQ ID NO 61
<211> LENGTH: 708
<212> TYPE: DNA
<213> ORGANISM: Homo sapiens

<400> SEQUENCE: 61

```
atggacatga gggtccccgc tcagctcctg gggcttctgc tgctctggct cccaggtgcc    60
agatgtgcca tccagttgac ccagtctcca tcctccctgt ctgcatctgt aggagacaga   120
gtcaccatca cttgccgggc aagtcagggc attagcagtg ctttagcctg gtatcagcag   180
aaaccaggga aagctcctaa gctcctgatc tatgatgcct ccaatttgga aagtggggtc   240
ccatcaaggt tcagcggcag tggatctggg acagatttca ctctcaccat cagcagcctg   300
cagcctgaag attttgcaac ttattactgt caacagttta atagttaccc gacgttcggc   360
caagggacca aggtggaaat caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca agcagactac gagaaacac aaagtctacg cctgcgaagt cacccatcag   660
ggcctgagct cgcccgtcac aaagagcttc aacaggggag agtgttga              708
```

<210> SEQ ID NO 62
<211> LENGTH: 235
<212> TYPE: PRT
<213> ORGANISM: Homo sapiens

<400> SEQUENCE: 62

```
Met Asp Met Arg Val Pro Ala Gln Leu Leu Gly Leu Leu Leu Leu Trp
1               5                   10                  15
Leu Pro Gly Ala Arg Cys Ala Ile Gln Leu Thr Gln Ser Pro Ser Ser
            20                  25                  30
Leu Ser Ala Ser Val Gly Asp Arg Val Thr Ile Thr Cys Arg Ala Ser
        35                  40                  45
Gln Gly Ile Ser Ser Ala Leu Ala Trp Tyr Gln Gln Lys Pro Gly Lys
```

Ala Pro Lys Leu Leu Ile Tyr Asp Ala Ser Asn Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Thr Phe Gly Gln Gly Thr Lys Val Glu Ile Lys
                115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 63
<211> LENGTH: 377
<212> TYPE: PRT
<213> ORGANISM: Homo sapiens

<400> SEQUENCE: 63

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
                115                 120                 125

Cys Pro Glu Pro Lys Ser Cys Asp Thr Pro Pro Pro Cys Pro Arg Cys
130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr

```
                        195                 200                 205
Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
        245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
        340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 64
<211> LENGTH: 2009
<212> TYPE: DNA
<213> ORGANISM: Homo sapiens

<400> SEQUENCE: 64
agctttctgg ggcgagccgg gcctgacttt ggctttgggg cagggagtgg gctaaggtga      60
ggcaggtggc gccagccagg tgcacaccca atgcccgtga gcccagacac tggaccctgc     120
ctggaccctc gtggatagac aagaaccgag gggcctctgc gcctgggccc agctctgtcc     180
cacaccgcgg tcacatggca ccacctctct tgcagcctcc accaagggcc catcggtctt     240 cccccctggcg ccctgctcca ggagcacctc cgagagcaca gccgccctgg gctgcctggt     300
caaggactac ttccccgaac cggtgacggt gtcgtggaac tcaggcgctc tgaccagcgg     360
cgtgcacacc ttcccagctg tcctacagtc tcaggactc tactcctca gcagcgtggt     420 gaccgtgccc tccagcaact tcggcaccca gacctacacc tgcaacgtag atcacaagcc     480
cagcaacacc aaggtggaca agacagttgg tgagaggcca gctcagggag ggagggtgtc     540
tgctggaagc caggctcagc cctcctgcct ggacgcaccc cggctgtgca gccccagccc     600
agggcagcaa ggcaggcccc atctgtctcc tcacccggag gcctctgccc gccccactca     660
tgctcaggga gagggtcttc tggctttttc caccaggctc caggcaggca caggctgggt     720
gcccctaccc caggccctc acacacaggg gcaggtgctt ggctcagacc tgccaaaagc     780
catatccggg aggaccctgc ccctgaccta agcccacccc aaaggccaaa ctgtccactc     840
cctcagctcg acaccttct ctcctcccag atccgagtaa ctcccaatct tctctctgca     900
gagcgcaaat gttgtgtcga gtgcccaccg tgcccaggta agcagcccca ggcctcgccc     960
tccagctcaa ggcgggacag gtgccctaga gtagcctgca tccagggaca ggccccagct    1020
gggtgctgac acgtccacct ccatctcttc ctcagcacca cctgtggcag gaccgtcagt    1080
cttcctcttc cccccaaaac ccaaggacac cctcatgatc tcccggaccc ctgaggtcac    1140
```

```
gtgcgtggtg gtggacgtga gccacgaaga ccccgaggtc cagttcaact ggtacgtgga    1200
cggcgtggag gtgcataatg ccaagacaaa gccacgggag gagcagttca acagcacgtt    1260
ccgtgtggtc agcgtcctca ccgttgtgca ccaggactgg ctgaacggca aggagtacaa    1320
gtgcaaggtc tccaacaaag gcctcccagc ccccatcgag aaaaccatct ccaaaaccaa    1380
aggtgggacc cgcggggtat gagggccaca tggacagagg ccggctcggc ccaccctctg    1440
ccctgggagt gaccgctgtg ccaacctctg tccctacagg gcagcccga gaaccacagg     1500 tgtacaccct gccccatcc cgggaggaga tgaccaagaa ccaggtcagc ctgacctgcc     1560
tggtcaaagg cttctacccc agcgacatcg ccgtggagtg ggagagcaat gggcagccgg    1620
agaacaacta caagaccaca cctcccatgc tggactccga cggctccttc ttcctctaca    1680
gcaagctcac cgtggacaag agcaggtggc agcagggaa cgtcttctca tgctccgtga     1740
tgcatgaggc tctgcacaac cactacacg agaagagcct ctccctgtct ccgggtaaat     1800
gagtgccacg gccggcaagc ccccgctccc caggctctcg gggtcgcgtg aggatgcttg    1860
gcacgtaccc cgtgtacata cttcccaggc acccagcatg gaaataaagc acccagcgct    1920
gccctgggcc cctgcgagac tgtgatggtt ctttccgtgg gtcaggccga gtctgaggcc    1980
tgagtggcat gagggaggca gagtgggtc                                      2009
```

<210> SEQ ID NO 65
<211> LENGTH: 2010
<212> TYPE: DNA
<213> ORGANISM: Homo sapiens

<400> SEQUENCE: 65

```
agctttctgg ggcgagccgg gcctgacttt ggctttgggg cagggagtgg gctaaggtga      60
ggcaggtggc gccagccagg tgcacaccca atgcccgtga gcccagacac tggaccctgc     120
ctggaccctc gtggatagac aagaaccgag gggcctctgc gccctgggcc cagctctgtc    180
ccacaccgcg gtcacatggc accacctctc ttgcagcctc caccaagggc ccatcggtct    240
tccccctggc gccctgctcc aggagcacct ccgagagcac agcggccctg gctgcctgg    300 tcaaggacta cttccccgaa ccggtgacgg tgtcgtggaa ctcaggcgct ctgaccagcg    360
gcgtgcacac cttcccggct gtcctacagt cctcaggact ctactccctc agcagcgtgg    420
tgaccgtgac ctccagcaac ttcggcaccc agacctacac ctgcaacgta gatcacaagc    480
ccagcaacac caaggtggac aagacagttg gtgagaggcc agctcaggga gggagggtgt    540
ctgctggaag ccaggctcag ccctcctgcc tggacgcacc ccggctgtgc agccccagcc    600
cagggcagca aggcaggccc catctgtctc ctcacccgga ggcctctgcc cgccccactc    660
atgctcaggg agagggtctt ctggcttttt ccaccaggct ccaggcaggc acaggctggg    720
tgcccctacc ccaggccctt cacacacagg ggcaggtgct tggctcagac ctgccaaaag    780
ccatatccgg gaggaccctg cccctgacct aagccgaccc caaaggccaa actgtccact    840
ccctcagctc ggacaccttc tctcctccca gatccgagta actcccaatc ttctctctgc    900
agagcgcaaa tgttgtgtcg agtgcccacc gtgcccagg aagccagccc aggcctcgcc     960
ctccagctca aggcgggaca ggtgccctag agtagcctgc atccagggac aggccccagc    1020
tgggtgctga cacgtccacc tccatctctt cctcagcacc acctgtggca ggaccgtcag    1080
tcttcctctt ccccccaaaa cccaaggaca ccctcatgat ctcccggacc cctgaggtca    1140
cgtgcgtggt ggtggacgtg agccacgaag acccgaggt ccagttcaac tggtacgtgg     1200
acggcatgga ggtgcataat gccaagacaa agccacggga ggagcagttc aacagcacgt    1260
```

```
tccgtgtggt cagcgtcctc accgtcgtgc accaggactg gctgaacggc aaggagtaca    1320
agtgcaaggt ctccaacaaa ggcctcccag cccccatcga gaaaaccatc tccaaaacca    1380
aaggtgggac ccgcggggta tgagggccac atggacagag gccggctcgg cccaccctct    1440
gccctgggag tgaccgctgt gccaacctct gtccctacag ggcagccccg agaaccacag    1500
gtgtacaccc tgccccatc ccgggaggag atgaccaaga accaggtcag cctgacctgc    1560
ctggtcaaag gcttctaccc cagcgacatc gccgtggagt gggagagcaa tgggcagccg    1620
gagaacaact acaagaccac acctcccatg ctggactccg acggctcctt cttcctctac    1680
agcaagctca ccgtggacaa gagcaggtgg cagcagggga acgtcttctc atgctccgtg    1740
atgcatgagg ctctgcacaa ccactacaca cagaagagcc tctccctgtc tccgggtaaa    1800
tgagtgccac ggccagcaag cccccgctcc ccaggctctc ggggtcgcgc gaggatgctt    1860
ggcacgtacc ccgtgtacat acttcccggg cacccagcat ggaaataaag cacccagcgc    1920
ttccctgggc ccctgcgaga ctgtgatggt tctttccacg ggtcaggccg agtctgaggc    1980
ctgagtggca tgagggaggc agagtgggtc                                    2010

<210> SEQ ID NO 66
<211> LENGTH: 2010
<212> TYPE: DNA
<213> ORGANISM: Homo sapiens

<400> SEQUENCE: 66
agctttctgg ggcgagccgg gcctgacttt ggctttgggg cagggagtgg gctaaggtga     60
ggcaggtggc gccagccagg tgcacaccca atgcccgtga gcccagacac tggaccctgc    120
ctggaccctc gtggatagac aagaaccgag gggcctctgc gccctgggcc cagctctgtc    180
ccacaccgcg gtcacatggc accacctctc ttgcagcctc caccaagggc ccatcggtct    240
tccccctggc gccctgctcc aggagcacct ccgagagcac agcggccctg ggctgcctgg    300
tcaaggacta cttccccgaa ccggtgacgg tgtcgtggaa ctcaggcgct ctgaccagcg    360
gcgtgcacac cttcccagct gtcctacagt cctcaggact ctactccctc agcagcgtgg    420
tgaccgtgcc ctccagcaac ttcggcaccc agacctacac ctgcaacgta gatcacaagc    480
ccagcaacac caaggtggac aagacagttg gtgagaggcc agctcaggga gggagggtgt    540
ctgctggaag ccaggctcag ccctcctgcc tggacgcacc ccggctgtgc agccccagcc    600
cagggcagca aggcaggccc catctgtctc ctcacccgga ggcctctgcc cgccccactc    660
atgctcaggg agagggtctt ctggcttttt ccaccaggct ccaggcaggc acaggctggg    720 tgccctacc ccaggccctt cacacacagg ggcaggtgct tggctcagac ctgccaaaag    780
ccatatccgg gaggaccctg cccctgacct aagccgaccc caaaggccaa actgtccact    840
ccctcagctc ggacaccttc tctcctccca gatcccgagta actcccaatc ttctctctgc    900
agagcgcaaa tgttgtgtcg agtgcccacc gtgcccagg aagccagccc aggcctcgcc    960
ctccagctca aggcgggaca ggtgccctag agtagcctgc atccagggac aggccccagc    1020
tgggtgctga cacgtccacc tccatctctt cctcagcacc acctgtggca ggaccgtcag    1080
tcttcctctt ccccccaaaa cccaaggaca ccctcatgat ctcccggacc cctgaggtca    1140
cgtgcgtggt ggtggacgtg agccacgaag acccgaggt ccagttcaac tggtacgtgg    1200
acggcgtgga ggtgcataat gccaagacaa agccacggga ggagcagttc aacagcacgt    1260
tccgtgtggt cagcgtcctc accgttgtgc accaggactg gctgaacggc aaggagtaca    1320
agtgcaaggt ctccaacaaa ggcctcccag cccccatcga gaaaaccatc tccaaaacca    1380
```

| | |
|---|---|
| aaggtgggac cgcggggta tgagggccac atggacagag gccggctcgg cccaccctct | 1440 |
| gccctgggag tgaccgctgt gccaacctct gtccctacag ggcagccccg agaaccacag | 1500 |
| gtgtacaccc tgcccccatc ccgggaggag atgaccaaga accaggtcag cctgacctgc | 1560 |
| ctggtcaaag gcttctaccc cagcgacatc gccgtggagt gggagagcaa tgggcagccg | 1620 |
| gagaacaact acaagaccac acctcccatg ctggactccg acggctcctt cttcctctac | 1680 |
| agcaagctca ccgtggacaa gagcaggtgg cagcagggga acgtcttctc atgctccgtg | 1740 |
| atgcatgagg ctctgcacaa ccactacacg cagaagagcc tctccctgtc tccgggtaaa | 1800 |
| tgagtgccac ggccggcaag cccccgctcc ccaggctctc ggggtcgcgt gaggatgctt | 1860 |
| ggcacgtacc ccgtgtacat acttcccagg cacccagcat ggaaataaag cacccagcgc | 1920 |
| tgccctgggc cctgcgaga ctgtgatggt tctttccgtg ggtcaggccg agtctgaggc | 1980 |
| ctgagtggca tgagggaggc agagtgggtc | 2010 |

<210> SEQ ID NO 67
<211> LENGTH: 2010
<212> TYPE: DNA
<213> ORGANISM: Homo sapiens

<400> SEQUENCE: 67

| | |
|---|---|
| agctttctgg ggcgagccgg gcctgacttt ggctttgggg cagggagtgg gctaaggtga | 60 |
| ggcaggtggc gccagccagg tgcacaccca atgcccgtga gcccagacac tggaccctgc | 120 |
| ctggaccctc gtggatagac aagaaccgag gggcctctgc gccctgggcc cagctctgtc | 180 |
| ccacaccgcg gtcacatggc accacctctc ttgcagcctc caccaagggc ccatcggtct | 240 |
| tccccctggc gccctgctcc aggagcacct ccgagagcac agcggccctg gctgcctgg | 300 |
| tcaaggacta cttccccgaa ccggtgacgg tgtcgtggaa ctcaggcgct ctgaccagcg | 360 |
| gcgtgcacac cttcccagct gtcctacagt cctcaggact ctactccctc agcagcgtgg | 420 |
| tgaccgtgcc ctccagcagc ttgggcaccc agacctacac ctgcaacgta gatcacaagc | 480 |
| ccagcaacac caaggtggac aagacagttg gtgagaggcc agctcaggga gggagggtgt | 540 |
| ctgctggaag ccaggctcag ccctcctgcc tggacgcacc ccggctgtgc agccccagcc | 600 |
| cagggcagca aggcaggccc catctgtctc ctcaccccgga ggcctctgcc cgccccactc | 660 |
| atgctcaggg agagggtctt ctggcttttt ccaccaggct ccaggcaggc acaggctggg | 720 |
| tgccctacc ccaggccctt cacacacagg ggcaggtgct tggctcagac ctgccaaaag | 780 |
| ccatatccgg gaggaccctg cccctgacct aagccgaccc caaaggccaa actgtccact | 840 |
| ccctcagctc ggacaccttc tctcctccca gatcccgagta actcccaatc ttctctctgc | 900 |
| agagcgcaaa tgttgtgtcg agtgcccacc gtgcccaggt aagccagccc aggcctcgcc | 960 |
| ctccagctca aggcgggaca ggtgccctag agtagcctgc atccagggac aggccccagc | 1020 |
| tgggtgctga cacgtccacc tccatctctt cctcagcacc acctgtggca ggaccgtcag | 1080 |
| tcttcctctt ccccccaaaa cccaaggaca ccctcatgat ctcccggacc cctgaggtca | 1140 |
| cgtgcgtggt ggtggacgtg agccacgaag acccccgaggt ccagttcaac tggtacgtgg | 1200 |
| acggcgtgga ggtgcataat gccaagacaa agccacggga ggagcagttc aacagcacgt | 1260 |
| tccgtgtggt cagcgtcctc accgttgtgc caccaggactg gctgaacggc aaggagtaca | 1320 |
| agtgcaaggt ctccaacaaa ggcctcccag cccccatcga gaaaaccatc tccaaaacca | 1380 |
| aaggtgggac cgcggggta tgagggccac atggacagag gccggctcgg cccaccctct | 1440 |
| gccctgggag tgaccgctgt gccaacctct gtccctacag ggcagccccg agaaccacag | 1500 |

```
gtgtacaccc tgcccccatc ccgggaggag atgaccaaga accaggtcag cctgacctgc    1560
ctggtcaaag gcttctaccc cagcgacatc gccgtggagt gggagagcaa tgggcagccg    1620
gagaacaact acaagaccac acctcccatg ctggactccg acggctcctt cttcctctac    1680
agcaagctca ccgtggacaa gagcaggtgg cagcagggga acgtcttctc atgctccgtg    1740
atgcatgagg ctctgcacaa ccactacacg cagaagagcc tctccctgtc tccgggtaaa    1800
tgagtgccac ggccggcaag cccccgctcc ccaggctctc ggggtcgcgt gaggatgctt    1860
ggcacgtacc ccgtgtacat acttcccagg cacccagcat ggaaataaag cacccagcgc    1920
tgccctgggc ccctgcgaga ctgtgatggt tctttccgtg ggtcaggccg agtctgaggc    1980
ctgagtggca tgagggaggc agagtgggtc                                     2010
```

<210> SEQ ID NO 68
<211> LENGTH: 2010
<212> TYPE: DNA
<213> ORGANISM: Homo sapiens

<400> SEQUENCE: 68

```
agctttctgg ggcgagccgg gcctgacttt ggctttgggg cagggagtgg gctaaggtga      60
ggcaggtggc gccagccagg tgcacaccca atgcccgtga gcccagacac tggaccctgc     120
ctggaccctc gtggatagac aagaaccgag gggcctctgc gccctgggcc cagctctgtc     180
ccacaccgcg gtcacatggc accacctctc ttgcagcctc caccaagggc ccatcggtct     240
tccccctggc gccctgctcc aggagcacct ccgagagcac agcggccctg gctgcctgg     300 tcaaggacta cttccccgaa ccggtgacgg tgtcgtggaa ctcaggcgct ctgaccagcg     360
gcgtgcacac cttcccagct gtcctacagt cctcaggact ctactccctc agcagcgtgg     420
tgaccgtgcc ctccagcaac ttcggcaccc agacctacac ctgcaacgta gatcacaagc     480
ccagcaacac caaggtggac aagacagttg gtgagaggcc agctcaggga gggagggtgt     540
ctgctggaag ccaggctcag ccctcctgcc tggacgcacc ccggctgtgc agccccagcc     600
cagggcagca aggcaggccc catctgtctc ctcacccgga ggcctctgcc cgccccactc     660
atgctcaggg agagggtctt ctggcttttt ccaccaggct ccaggcaggc acaggctggg     720
tgcccctacc ccaggccctt cacacacagg ggcaggtgct tggctcagac ctgccaaaag     780
ccatatccgg gaggaccctg cccctgacct aagccgaccc caaaggccaa actgtccact     840
ccctcagctc ggacaccttc tctcctccca gatccgagta actcccaatc ttctctctgc     900
agagcgcaaa tgttgtgtcg agtgcccacc gtgcccaggt aagccagccc aggcctcgcc     960
ctccagctca aggcgggaca ggtgccctag agtagcctgc atccagggac aggccccagc    1020
tgggtgctga cacgtccacc tccatctctt cctcagcacc acctgtggca ggaccgtcag    1080
tcttcctctt ccccccaaaa cccaaggaca cctcatgat ctcccggacc cctgaggtca    1140
cgtgcgtggt ggtggacgtg agccacgaag acccgaggt ccagttcaac tggtacgtgg    1200
acggcgtgga ggtgcataat gccaagacaa agccacggga ggagcagttc aacagcacgt    1260
tccgtgtggt cagcgtcctc accgttgtgc accaggactg gctgaacggc aaggagtaca    1320
agtgcaaggt ctccaacaaa ggcctcccag cccccatcga aaaaccatc tccaaaacca    1380 aaggtgggac ccgcggggta tgagggcac atggacagag gccggctcgg cccacctct    1440 gccctgggag tgaccgctgt gccaacctct gtcctacag gcagcccga gaaccacag    1500 gtgtacaccc tgcccccatc ccgggaggag atgaccaaga accaggtcag cctgacctgc    1560
ctggtcaaag gcttctaccc cagcgacatc gccgtggagt gggagagcaa tgggcagccg    1620
```

| | |
|---|---:|
| gagaacaact acaagaccac gcctcccatg ctggactccg acggctcctt cttcctctac | 1680 |
| agcaagctca ccgtggacaa gagcaggtgg cagcagggga acgtcttctc atgctccgtg | 1740 |
| atgcatgagg ctctgcacaa ccactacacg cagaagagcc tctccctgtc tccgggtaaa | 1800 |
| tgagtgccac ggccggcaag ccccgctcc ccaggctctc ggggtcgcgt gaggatgctt | 1860 |
| ggcacgtacc ccgtgtacat acttcccagg cacccagcat ggaaataaag cacccagcgc | 1920 |
| tgccctgggc ccctgcgaga ctgtgatggt tctttccgtg ggtcaggccg agtctgaggc | 1980 |
| ctgagtggca tgagggaggc agagtgggtc | 2010 |

<210> SEQ ID NO 69
<211> LENGTH: 935
<212> TYPE: DNA
<213> ORGANISM: Homo sapiens

<400> SEQUENCE: 69

| | |
|---|---:|
| tcttctctct gcagagcgca aatgttgtgt cgagtgccca ccgtgcccag gtaagccagc | 60 |
| ccaggcctcg ccctccagct caaggcggga caggtgccct agagtagcct gcatccaggg | 120 |
| acaggcccca gctgggtgct gacacgtcca cctccatctc ttcctcagca ccacctgtgg | 180 |
| caggaccgtc agtcttcctc ttcccccaa aacccaagga caccctcatg atctcccgga | 240 |
| cccctgaggt cacgtgcgtg gtggtggacg tgagccacga agaccccgag gtccagttca | 300 |
| actggtacgt ggacggcgtg gaggtgcata atgccaagac aaagccacgg gaggagcagt | 360 |
| tcaacagcac gttccgtgtg gtcagcgtcc tcaccgttgt gcaccaggac tggctgaacg | 420 |
| gcaaggagta caagtgcaag gtctccaaca aaggcctccc agcccccatc gagaaaacca | 480 |
| tctccaaaac caaggtggg acccgcgggg tatgagggcc acatggacag acggcggctt | 540 |
| cggcccaccc tctgccctgg gagtgaccgc tgtgccaacc tctgtcccta cagggcagcc | 600 |
| ccgagaacca caggtgtaca ccctgccccc atcccgggag gagatgacca agaaccaggt | 660 |
| cagcctgacc tgcctggtca aaggcttcta ccccagcgac atcgccgtgg agtgggagag | 720 |
| caatgggcag ccggagaaca actacaagac cacacctccc atgctggact ccgacggctc | 780 |
| cttcttcctc tacagcaagc tcaccgtgga caagagcagg tggcagcagg ggaacgtctt | 840 |
| ctcatgctcc gtgatgcatg aggctctgca caaccactac acgcagaaga gcctctccct | 900 |
| gtctccgggt aaatgagtgc cacggccggc aagcc | 935 |

<210> SEQ ID NO 70
<211> LENGTH: 935
<212> TYPE: DNA
<213> ORGANISM: Homo sapiens

<400> SEQUENCE: 70

| | |
|---|---:|
| tcttctctct gcagagcgca aatgttgtgt cgagtgccca ccgtgcccag gtaagccagc | 60 |
| ccaggcctcg ccctccagct caaggcggga caggtgccct agagtagcct gcatccaggg | 120 |
| acaggcccca gctgggtgct gacacgtcca cctccatctc ttcctcagca ccacctgtgg | 180 |
| caggaccgtc agtcttcctc ttcccccaa aacccaagga caccctcatg atctcccgga | 240 |
| cccctgaggt cacgtgcgtg gtggtggacg tgagccacga agaccccgag gtccagttca | 300 |
| actggtacgt ggacggcatg gaggtgcata atgccaagac aaagccacgg gaggagcagt | 360 |
| tcaacagcac gttccgtgtg gtcagcgtcc tcaccgtcgt gcaccaggac tggctgaacg | 420 |
| gcaaggagta caagtgcaag gtctccaaca aaggcctccc agcccccatc gagaaaacca | 480 |
| tctccaaaac caaggtggg acccgcgggg tatgagggcc acatggacag acggcggctt | 540 |

```
cggcccaccc tctgccctgg gagtgaccgc tgtgccaacc tctgtcccta cagggcagcc    600
ccgagaacca caggtgtaca ccctgccccc atcccgggag gagatgacca agaaccaggt    660
cagcctgacc tgcctggtca aaggcttcta ccccagcgac atcgccgtgg agtgggagag    720
caatgggcag ccggagaaca actacaagac cacacctccc atgctggact ccgacggctc    780
cttcttcctc tacagcaagc tcaccgtgga caagagcagg tggcagcagg ggaacgtctt    840
ctcatgctcc gtgatgcatg aggctctgca caaccactac acacagaaga gcctctccct    900
gtctccgggt aaatgagtgc cacggccggc aagcc                               935
```

<210> SEQ ID NO 71
<211> LENGTH: 1208
<212> TYPE: DNA
<213> ORGANISM: Homo sapiens

<400> SEQUENCE: 71

```
caagcccagc aacaccaagg tggacaagag agttggtgag aggccagcgc agggagggag      60
ggtgtctact ggaagccagc tcagccctcc tgcctggacg catcccggct gtgcagtccc     120
agcccagggc accaaggcag gccccgtctg actcctcacc cggaggcctc tgcccgcccc     180
actcatgctc agggagaggg tcttctggct ttttccacca ggctccaggc aggcacaggc     240 tgggtgccc tacccaggc ccttcacaca caggggcagg tgctgcgctc agacgtgcca      300
gagccatatc caggaggacc ctgcccctga cctaagccca ccccaaaggc caaactctct     360
actcactcag ctcagacacc ttctctcttc ccagatctga gtaactccca atcttctctc     420
tgcagagctc aaaaccccac ttggtgacac aactcacaca tgcccacggt gcccaggtaa     480
gccagcccag gcctcgccct ccagctcaag gcgggacaag agcccctagag tggcctgagt     540 ccagggacag gccccagcag ggtgctgacg catccacctc catcccagat ccccgtaact     600
cccaatcttc tctctgcaga gcctaaatct tgtgacacac ctcccccgtg cccacggtgc     660
ccaggtaagc cagcccaggc ctcgccctcc agctcaaggc aggacaggtg ccctagagtg     720
gcctgagtcc agggacaggc cccagcaggg tgctgacgca tccacctcca tcccagatcc     780
ccgtaactcc caatcttctc tctgcagagc ctaaatcttg tgacacacct cccccgtgcc     840
cacggtgccc aggtaagcca gcccaggcct cgcctccag ctcaaggcag gacaggtgcc      900
ctagagtggc ctgagtccag ggacaggccc cagcagggtg ctgacgcatc cacctccatc     960
ccagatcccc gtaactccca atcttctctc tgcagagccc aaatcttgtg acacacctcc    1020
cccgtgccca aggtgcccag gtaagccagc ccaggcctcg ccctccagct caaggcagga   1080
caggtgccct agagtggcct gcatccaggg acaggtccca gtcgggtgct gacacatctg   1140
cctccatctc ttcctcagca cctgaactcc tgggaggacc gtcagtcttc ctcttccccc   1200
ctaaaccc                                                            1208
```

<210> SEQ ID NO 72
<211> LENGTH: 2372
<212> TYPE: DNA
<213> ORGANISM: Homo sapiens

<400> SEQUENCE: 72

```
agctttctgg ggcaggccag gcctgacttt ggctgggggc agggaggggg ctaaggtgac      60
gcaggtggcg ccagccaggc gcacacccaa tgcccgtgag cccagacact ggaccctgcc     120
tggaccctcg tggatagaca agaaccgagg ggcctctgcg ccctgggccc agctctgtcc     180
cacaccgcag tcacatggcg ccatctctct tgcagcttcc accaagggcc catcggtctt     240
```

```
cccctggcg ccctgctcca ggagcacctc tggggcaca gcggccctgg gctgcctggt    300
caaggactac ttccccgaac cggtgacggt gtcgtggaac tcaggcgccc tgaccagcgg    360
cgtgcacacc ttcccggctg tcctacagtc ctcaggactc tactccctca gcagcgtggt    420
gaccgtgccc tccagcagct gggcaccca gacctacacc tgcaacgtga atcacaagcc    480
cagcaacacc aaggtggaca gagagttgg tgagaggcca gcgcagggag ggagggtgtc    540
tgctggaagc caggctcagc cctcctgcct ggacgcatcc cggctgtgca gtcccagccc    600
agggcaccaa gcaggcccc gtctgactcc tcacccggag gcctctgccc gccccactca    660
tgctcaggga gagggtcttc tggcttttc caccaggctc cgggcaggca caggctggat    720
gcccctaccc caggcccttc acacacaggg gcaggtgctg cgctcagagc tgccaaaagc    780
catatccagg aggaccctgc ccctgacctg agcccacccc aaaggccaaa ctctctactc    840
actcagctca gacaccttct ctcttcccag atctgagtaa ctcccaatct tctctctgca    900
gagctcaaaa ccccacttgg tgacacaact cacacatgcc cacggtgccc aggtaagcca    960
gcccaggact cgcccctccag ctcaaggcgg gacaagagcc ctagagtggc ctgagtccag    1020
ggacaggccc cagcagggtg ctgacgcgtc cacctccatc ccagatcccc gtaactccca    1080
atcttctctc tgcagagccc aaatcttgtg acacacctcc cccatgccca cggtgcccag    1140
gtaagccagc ccaggcctcg ccctccagct caaggcggga caagagccct agagtggcct    1200
gagtccaggg acaggcccca gcaggtgct gacgcatcca cctccatccc agatccccgt    1260
aactcccaat cttctctctg cagagcccaa atcttgtgac acacctcccc cgtgcccaag    1320
gtgcccaggt aagccagccc aggcctcgcc ctccagctca aggcaggaca ggtgccctag    1380
agtggcctgc atccagggac aggtcccagt cgggtgctga cacatctgcc tccatctctt    1440
cctcagcacc tgaactcctg ggaggaccgt cagtcttcct cttcccccca aacccaagg    1500 atacccttat gatttcccgg acccctgagg tcacgtgcgt ggtggtggac gtgagccacg    1560
aagaccccga ggtccagttc aagtggtacg tggacggcgt ggaggtgcat aatgccaaga    1620
caaagccgcg ggaggagcag tacaacagca cgttccgtgt ggtcagcgtc ctcaccgtcc    1680
tgcaccagga ctggctgaac ggcaaggagt acaagtgcaa ggtctccaac aaagccctcc    1740
cagcccccat cgagaaaacc atctccaaaa ccaaaggtgg gacccgcggg gtatgagggc    1800
cacatggaca gaggccagct tgacccaccc tctgccctgg gagtgaccgc tgtgccaacc    1860
tctgtcccta caggacagcc ccgagaacca caggtgtaca ccctgccccc atcccgggag    1920
gagatgacca agaaccaggt cagcctgacc tgcctggtca aaggcttcta ccccagcgac    1980
atcgccgtgg agtgggagag cagcgggcag ccggagaaca actacaacac cacgcctccc    2040
gtgctggact ccgacggctc cttcttcctc tacagcaggc taaccgtgga caagagcagg    2100
tggcaggagg ggaatgtctt ctcatgctcc gtgatgcatg aggctctgca caaccgcttc    2160
acgcagaaga gcctctccct gtctccgggt aaatgagtgc gacggccggc aagcccccgc    2220
tccccaggct ctcggggtcg cgcgaggatg cttggcacgt accccgtgta catacttccc    2280
gggcgcccag catggaaata aagcacccag cgctgccctg gccccctgca agactgtgat    2340
ggttcattct gcgggtcagg ccgagtctga gg                                   2372
```

<210> SEQ ID NO 73
<211> LENGTH: 1816
<212> TYPE: DNA
<213> ORGANISM: Homo sapiens

<400> SEQUENCE: 73

```
ttgcagcctc caccaagggc ccatcggtct tcccccctggc gccctgctcc aggagcacct      60
ctgggggcac agcggccctg ggctgcctgg tcaaggacta cttccccgaa ccggtgacgg     120
tgtcgtggaa ctcaggcgcc ctgaccagcg cgtgcacac cttcccggct gtcctacagt      180
cctcaggact ctactccctc agcagcgtgg tgaccgtgcc ctccagcagc ttgggcaccc     240
agacctacac ctgcaacgtg aatcacaagc cagcaacac caaggtggac aagagagttg      300
gtgagaggcc agcgcaggga gggagggtgt ctgctggaag ccaggctcag ccctcctgcc     360
tggacgcatc ccggctgtgc agtcccagcc cagggcacca aggcaggccc cgtctgactc     420
ctcacccgga ggcctctgcc cgcccactc atgctcaggg agagggtctt ctggcttttt      480
ccaccaggct ccgggcaggc acaggctgga tgccctacc ccaggccctt cacacacagg      540
ggcaggtgct gcgctcagag ctgccaagag ccatatccag gaggaccctg cccctgacct     600
aagcccaccc caaaggccaa actctctact cactcagctc agacaccttc tctcttccca     660
gatctgagta actcccaatc ttctctctgc agagctcaaa accccacttg gtgacacaac     720
tcacacatgc ccacggtgcc caggtaagcc agcccaggcc tcgccctcca gctcaaggcg     780
ggacaagagc cctagagtgg cctgagtcca gggacaggcc ccagcagggt gctgacgcat     840
ccacctccat cccagatccc cgtaactccc aatcttctct ctgcagagcc caaatcttgt     900
gacacacctc ccccgtgccc aaggtgccca ggtaagccag cccaggcctc gccctccagc     960
tcaaggcagg acaggtgccc tagagtggcc tgcatccagg acaggtccc agtcgggtgc     1020 tgacacatct gcctccatct cttcctcagc acctgaactc ctgggaggac cgtcagtctt    1080
cctcttcccc ccaaaaccca aggatacct tatgattcc cggacccctg aggtcacgtg      1140
cgtggtggtg gacgtgagcc acgaagaccc cgaggtccag ttcaagtggt acgtggacgg    1200
cgtggaggtg cataatgcca agacaaagcc gcgggaggag cagtacaaca gcacgttccg    1260
tgtggtcagc gtcctcaccg tcctgcacca ggactggctg aacggcaagg agtacaagtg    1320
caaggtctcc aacaaagccc tcccagcccc catcgagaaa accatctcca aaccaaagg    1380 tgggacccgc ggggtatgag ggccacatgg acagaggcca gcttgaccca ccctctgccc    1440
tgggagtgac cgctgtgcca acctctgtcc ctacaggaca gccccgagaa ccacaggtgt    1500
acaccctgcc cccatcccgg gaggagatga ccaagaacca ggtcagcctg acctgcctgg    1560
tcaaaggctt ctaccccagc gacatcgccg tggagtggga gagcagcggg cagccggaga    1620 caactacaa caccacgcct cccatgctgg actccgacgg ctccttcttc ctctacagca     1680
agctcaccgt ggacaagagc aggtggcagc aggggaacat cttctcatgc tccgtgatgc    1740
atgaggctct gcacaaccgc ttcacgcaga agagcctctc cctgtctccg ggtaaatgag    1800
tgcgacggcc ggcaag                                                    1816
```

<210> SEQ ID NO 74
<211> LENGTH: 2211
<212> TYPE: DNA
<213> ORGANISM: Homo sapiens

<400> SEQUENCE: 74

```
tcacatggcg ccatctctct tgcagcttcc accaagggcc catcggtctt cccccctggcg      60 ccctgctcca ggagcacctc tggggcaca gcggccctgg gctgcctggt caaggactac     120
ttccccgaac cggtgacggt gtcgtggaac tcaggcgccc tgaccagcgg cgtgcacacc    180
ttcccggctc tcctacagtc ctcaggactc tactccctca gcagcgtggt gaccgtgccc    240
tccagcagct gggcaccca gacctacacc tgcaacgtga atcacaagcc cagcaacacc    300
```

```
aaggtggaca agagagttgg tgagaggcca gcgcagggag ggagggtgtc tgctggaagc      360
caggctcagc cctcctgcct ggacgcatcc cggctgtgca gtcccagccc agggcaccaa      420
ggcaggcccc gtctgactcc tcacccggag gcctctgccc gccccactca tgctcaggga      480
gagggtcttc tggcttttc caccaggctc cgggcaggca caggctggat gcccctaccc       540
caggcccttc acacacaggg gcaggtgctg cgctcagagc tgccaagagc catatccagg      600
aggaccctgc ccctgaccta agcccacccc aaaggccaaa ctctctactc actcagctca      660
gacaccttct ctcttcccag atctgagtaa ctcccaatct tctctctgca gagctcaaaa      720
ccccacttgg tgacacaact cacacatgcc cacggtgccc aggtaagcca gcccaggcct      780
cgccctccag ctcaaggcgg gacaagagcc ctagagtggc ctgagtccag ggacaggccc      840
cagcagggtg ctgacgcatc cacctccatc ccagatcccc gtaactccca atcttctctc      900
tgcagagccc aaatcttgtg acacacctcc cccgtgccca cggtgcccag gtaagccagc      960
ccaggcctcg ccctccagct caaggcagga caagagccct agagtggcct gagtccaggg      1020
acaggcccca gcagggtgct gacgcgtcca cctccatccc agatccccgt aactcccaat      1080
cttctctctg cagagcccaa atcttgtgac acacctcccc catgcccacg gtgcccaggt      1140
aagccagccc aggcctcgcc ctcagctca aggcgggaca agagccctag agtggcctga      1200
gtccagggac aggccccagc agggtgctga cgcatccacc tccatcccag atccccgtaa      1260
ctcccaatct tctctctgca gagcccaaat cttgtgacac acctcccccg tgcccaaggt      1320
gcccaggtaa gccagcccag gcctcgccct ccagctcaag gcaggacagg tgccctagag      1380
tggcctgcat ccagggacag gtcccagtcg ggtgctgaca catctgcctc catctcttcc      1440
tcagcacctg aactcctggg aggaccgtca gtcttcctct tcccccaaa acccaaggat       1500 acccttatga tttcccggac ccctgaggtc acgtgcgtgg tggtggacgt gagccacgaa      1560
gaccccgagg tccagttcaa gtggtacgtg gacggcgtgg aggtgcataa tgccaagaca      1620
aagccgcggg aggagcagta caacagcacg ttccgtgtgg tcagcgtcct caccgtcctg      1680
caccaggact ggctgaacgg caaggagtac aagtgcaagg tctccaacaa agccctccca      1740
gcccccatcg agaaaaccat ctccaaaacc aaaggtggga cccgcggggt atgagggcca      1800
catggacaga ggccagcttg acccaccctc tgccctggga gtgaccgctg tgccaacctc      1860
tgtccctaca ggacagcccc gagaaccaca ggtgtacacc ctgcccccat cccgggagga      1920
gatgaccaag aaccaggtca gcctgacctg cctggtcaaa ggcttctacc ccagcgacat      1980
cgccgtggag tgggagagca cgggcagcc ggagaacaac tacaacacca cgcctcccat       2040
gctggactcc gacggctcct tcttcctcta cagcaagctc accgtggaca agagcaggtg      2100
gcagcagggg aacatcttct catgctccgt gatgcatgag gctctgcaca accgcttcac      2160
gcagaagagc ctctccctgt ctccgggtaa atgagtgcga cggccggcaa g              2211
```

<210> SEQ ID NO 75
<211> LENGTH: 2211
<212> TYPE: DNA
<213> ORGANISM: Homo sapiens

<400> SEQUENCE: 75

```
tcacatggcg ccatctctct tgcagcttcc accaagggcc catcggtctt ccccctggcg       60
ccctgctcca ggagcacctc tgggggcaca gcggccctgg gctgcctggt caaggactac      120 ttccccagaac cggtgacggt gtcgtggaac tcaggcgccc tgaccagcgg cgtgcacacc      180
ttcccggctg tcctacagtc ctcaggactc tactccctca gcagcgtggt gaccgtgccc      240
```

```
tccagcagct tgggcaccca gacctacacc tgcaacgtga atcacaagcc cagcaacacc      300
aaggtggaca agagagttgg tgagaggcca gcgcagggag ggagggtgtc tgctggaagc      360
caggctcagc cctcctgcct ggacgcatcc cggctgtgca gtcccagccc agggcaccaa      420
ggcaggcccc gtctgactcc tcacccggag gcctctgccc gccccactca tgctcaggga      480
gagggtcttc tggcttttc caccaggctc cgggcaggca caggctggat gcccctaccc       540
caggcccttc acacacaggg gcaggtgctg cgctcagagc tgccaagagc catatccagg      600
aggaccctgc ccctgaccta agcccacccc aaaggccaaa ctctctactc actcagctca      660
gacaccttct ctcttcccag atctgagtaa ctcccaatct tctctctgca gagctcaaaa      720
ccccacttgg tgacacaact cacacatgcc cacggtgccc aggtaagcca gcccaggcct      780
cgccctccag ctcaaggcgg gacaagagcc ctagagtggc ctgagtccag ggacaggccc      840
cagcagggtg ctgacgcatc cacctccatc ccagatcccc gtaactccca atcttctctc      900
tgcagagccc aaatcttgtg acacacctcc cccgtgccca cggtgcccag gtaagccagc      960
ccaggcctcg ccctccagct caaggcagga caagagccct agagtggcct gagtccaggg      1020
acaggcccca gcgggtgct gacgcgtcca cctccatccc agatcccgt aactcccaat        1080 cttctctctg cagagcccaa atcttgtgac acacctcccc catgcccacg gtgcccaggt      1140
aagccagccc aggcctcgcc ctcagctca aggcgggaca agagccctag agtggcctga       1200
gtccagggac aggccccagc agggtgctga cgcatccacc tccatcccag atccccgtaa      1260
ctcccaatct tctctctgca gagcccaaat cttgtgacac acctcccccg tgcccaaggt      1320
gcccaggtaa gccagcccag gcctcgccct ccagctcaag gcaggacagg tgccctagag      1380
tggcctgcat ccaggacag gtcccagtcg ggtgctgaca catctgcctc catctcttcc       1440
tcagcacctg aactcctggg aggaccgtca gtcttcctct tcccccaaa acccaaggat       1500 accctttatga tttcccggac ccctgaggtc acgtgcgtgg tggtggacgt gagccacgaa     1560
gaccccgagg tccagttcaa gtggtacgtg gacggcgtgg aggtgcataa tgccaagaca     1620
aagccgcggg aggagcagta caacagcacg ttccgtgtgg tcagcgtcct caccgtcctg    1680
caccaggact ggctgaacgg caaggagtac aagtgcaagg tctccaacaa agccctccca    1740
gcccccatcg agaaaaccat ctccaaaacc aaaggtggga cccgcggggt atgagggcca     1800
catggacaga ggccagcttg acccaccctc tgccctggga gtgaccgctg tgccaacctc    1860
tgtccctaca gggcagcccc gagaaccaca ggtgtacacc ctgccccat cccgggagga     1920 gatgaccaag aaccaggtca gcctgacctg cctggtcaaa ggcttctacc ccagcgacat    1980
cgccgtggag tgggagagca gcgggcagcc ggagaacaac tacaagacca cgcctcccat    2040
gctggactcc gacggctcct tcttcctcta cagcaagctc accgtggaca agagcaggtg    2100
gcagcagggg aacatcttct catgctccgt gatgcatgag gctctgcaca accgcttcac    2160
gcagaagagc ctctccctgt ctccgggtaa atgagtgcga cggccggcaa g              2211

<210> SEQ ID NO 76
<211> LENGTH: 2211
<212> TYPE: DNA
<213> ORGANISM: Homo sapiens

<400> SEQUENCE: 76
tcacatggcg ccatctctct tgcagcttcc accaagggcc catcggtctt cccctggcg        60 ccctgctcca ggagcacctc tgggggcaca gcggccctgg gctgcctggt caaggactac      120
ttccccgaac cggtgacggt gtcgtggaac tcaggcgccc tgaccagcgg cgtgcacacc      180
```

```
ttcccggctg tcctacagtc ctcaggactc tactccctca gcagcgtggt gaccgtgccc      240
tccagcagct tgggcaccca gacctacacc tgcaacgtga atcacaagcc cagcaacacc      300
aaggtggaca agagagttgg tgagaggcca gcgcagggag ggagggtgtc tgctggaagc      360
caggctcagc cctcctgcct ggacgcatcc cggctgtgca gtcccagccc agggcaccaa      420
ggcaggcccc gtctgactcc tcacccggag gcctctgccc gccccactca tgctcaggga      480
gagggtcttc tggcttttc caccaggctc cgggcaggca caggctggat gcccctaccc       540
caggcccttc acacacaggg gcaggtgctg cgctcagagc tgccaagagc catatccagg      600
aggaccctgc ccctgaccta gcccaccccc aaaggccaaa ctctctactc actcagctca      660
gacaccttct ctcttcccag atctgagtaa ctcccaatct tctctctgca gagctcaaaa      720
ccccacttgg tgacacaact cacacatgcc cacggtgccc aggtaagcca gcccaggcct      780
cgccctccag ctcaaggcgg gacaagagcc ctagagtggc ctgagtccag gacaggccc      840 cagcagggtg ctgacgcatc cacctccatc ccagatcccc gtaactccca atcttctctc      900
tgcagagccc aaatcttgtg acacacctcc cccgtgccca ggtgcccag gtaagccagc      960 ccaggcctcg ccctccagct caaggcagga caagagccct agagtggcct gagtccaggg      1020
acaggcccca gcagggtgct gacgcgtcca cctccatccc agatccccgt aactcccaat      1080
cttctctctg cagagcccaa atcttgtgac acacctcccc catgcccacg gtgcccaggt      1140
aagccagccc aggcctcgcc ctcagctca aggcgggaca agagccctag agtggcctga       1200
gtccagggac aggccccagc agggtgctga cgcatccacc tccatcccag atccccgtaa      1260
ctcccaatct tctctctgca gagcccaaat cttgtgacac acctcccccg tgcccaaggt      1320
gcccaggtaa gccagcccag gcctcgccct ccagctcaag gcaggacagg tgccctagag      1380
tggcctgcat ccagggacag gtcccagtcg ggtgctgaca catctgcctc catctcttcc      1440
tcagcacctg aactcctggg aggaccgtca gtcttcctct tcccccaaa acccaaggat       1500 acccttatga tttcccggac ccctgaggtc acgtgcgtgg tggtggacgt gagccacgaa      1560
gaccccgagg tccagttcaa gtggtacgtg gacggcgtgg aggtgcataa tgccaagaca      1620
aagccgcggg aggagcagta acagcacg ttccgtgtgg tcagcgtcct caccgtcctg        1680
caccaggact ggctgaacgg caaggagtac aagtgcaagg tctccaacaa agccctccca      1740
gcccccatcg agaaaaccat ctccaaaacc aaagtgggga cccgcggggt atgagggcca      1800
catggacaga ggccagcttg acccaccctc tgccctggga gtgaccgctg tgccaacctc      1860
tgtccctaca gggcagcccc gagaaccaca ggtgtacacc ctgccccat cccgggagga      1920 gatgaccaag aaccaggtca gcctgacctg cctggtcaaa ggcttctacc ccagcgacat      1980
cgccgtggag tgggagagca gcgggcagcc ggagaacaac tacaagacca cgcctcccat      2040
gctggactcc gacggctcct tcttcctcta cagcaagctc accgtggaca agagcaggtg      2100
gcagcagggg aacatcttct catgctccgt gatgcatgag gctctgcaca accgcttcac      2160
gcagaagagc ctctccctgt ctccgggtaa atgagtgcga cggccggcaa g              2211
```

<210> SEQ ID NO 77
<211> LENGTH: 2211
<212> TYPE: DNA
<213> ORGANISM: Homo sapiens

<400> SEQUENCE: 77

```
tcacatggcg ccatctctct tgcagcttcc accaagggcc catcggtctt ccccctggcg       60
ccctgctcca ggagcacctc tgggggcaca gcggccctgg gctgcctggt caaggactac      120
```

```
ttccccgaac cggtgacggt gtcgtggaac tcaggcgccc tgaccagcgg cgtgcacacc    180
ttcccggctg tcctacagtc ctcaggactc tactccctca gcagcgtggt gaccgtgccc    240
tccagcagct tgggcaccca gacctacacc tgcaacgtga atcacaagcc cagcaacacc    300
aaggtggaca agagagttgg tgagaggcca gcgcagggag ggagggtgtc tgctggaagc    360
caggctcagc cctcctgcct ggacgcatcc cggctgtgca gtcccagccc agggcaccaa    420
ggcaggcccc gtctgactcc tcacccggag gcctctgccc gccccactca tgctcaggga    480
gagggtcttc tggcttttc caccaggctc cgggcaggca caggctggat gcccctaccc    540
caggcccttc acacacaggg gcaggtgctg cgctcagagc tgccaagagc catatccagg    600
aggaccctgc ccctgaccta agcccacccc aaaggccaaa ctctctactc actcagctca    660
gacaccttct ctcttcccag atctgagtaa ctcccaatct tctctctgca gagctcaaaa    720
ccccacttgg tgacacaact cacacatgcc cacggtgccc aggtaagcca gcccaggcct    780
cgccctccag ctcaaggcgg gacaagagcc ctagagtggc ctgagtccag ggacaggccc    840
cagcagggtg ctgacgcatc cacctccatc ccagatcccc gtaactccca atcttctctc    900
tgcagagccc aaatcttgtg acacacctcc cccgtgccca cggtgcccag gtaagccagc    960
ccaggcctcg ccctccagct caaggcagga caagagccct agagtggcct gagtccaggg   1020
acaggcccca gcagggtgct gacgcgtcca cctccatccc agatccccgt aactcccaat   1080
cttctctctg cagagcccaa atcttgtgac acacctcccc catgcccacg gtgcccaggt   1140
aagccagccc aggcctcgcc ctccagctca aggcgggaca agagccctag agtggcctga   1200
gtccagggac aggccccagc agggtgctga cgcatccacc tccatcccag atccccgtaa   1260
ctcccaatct tctctctgca gagcccaaat cttgtgacac acctccccg tgcccaaggt   1320 gcccaggtaa gccagcccag gcctcgccct ccagctcaag gcaggacagg tgccctagag   1380
tggcctgcat ccagggacag gtcccagtcg ggtgctgaca catctgcctc catctcttcc   1440
tcagcacctg aactcctggg aggaccgtca gtcttcctct ccccccaaa acccaaggat   1500 acccttatga tttcccggac ccctgaggtc acgtgcgtgg tggtggacgt gagccacgaa   1560
gaccccgagg tccagttcaa gtggtacgtg gacggcgtgg aggtgcataa tgccaagaca   1620
aagccgcggg aggagcagta caacagcacg ttccgtgtgg tcagcgtcct caccgtcctg   1680
caccaggact ggctgaacgg caaggagtac aagtgcaagg tctccaacaa agccctccca   1740 gccccatcg agaaaaccat ctccaaaacc aaaggtggga cccgcggggt atgagggcca   1800
catggacaga ggccagcttg acccaccctc tgccctggga gtgaccgctg tgccaacctc   1860
tgtccctaca ggacagcccc gagaaccaca ggtgtacacc ctgcccccat ccgggagga   1920 gatgaccaag aaccaggtca gcctgacctg cctggtcaaa ggcttctacc ccagcgacat   1980
cgccgtggag tgggagagca atgggcagcc ggagaacaac tacaacacca cgcctcccat   2040
gctggactcc gacggctcct tcttcctcta cagcaagctc accgtggaca gagcaggtg   2100 gcagcagggg aacatcttct catgctccgt gatgcatgag gctctgcaca accgcttcac   2160
gcagaagagc ctctccctgt ctccgggtaa atgagtgcga cggccggcaa g            2211

<210> SEQ ID NO 78
<211> LENGTH: 2211
<212> TYPE: DNA
<213> ORGANISM: Homo sapiens

<400> SEQUENCE: 78
tcacatggcg ccatctctct tgcagcttcc accaagggcc catcggtctt ccccctggcg    60
```

```
ccctgctcca ggagcacctc tgggggcaca gcggccctgg gctgcctggt caaggactac    120
ttccccgaac cggtgacggt gtcgtggaac tcaggcgccc tgaccagcgg cgtgcacacc    180 ttccggctg tcctacagtc ctcaggactc tactccctca gcagcgtggt gaccgtgccc     240
tccagcagct tgggcaccca gacctacacc tgcaacgtga atcacaagcc cagcaacacc    300
aaggtggaca gagagttgg tgagaggcca gcgcagggag ggagggtgtc tgctggaagc     360
caggctcagc cctcctgcct ggacgcatcc cggctgtgcg gtcccagccc agggcaccaa    420
ggcaggcccc gtctgactcc tcacccggag gcctctgccc gccccactca tgctcaggga    480
gagggtcttc tggcttttc caccaggctc cgggcaggca caggctggat gccctaccc     540 caggcccttc acacacaggg gcaggtgctg cgctcagagc tgccaagagc catatccagg    600
aggaccctgc ccctgaccta agcccacccc aaaggccaaa ctctctactc actcagctca    660
gacaccttct ctcttcccag atctgagtaa ctcccaatct tctctctgca gagctcaaaa    720
ccccacttgg tgacacaact cacacatgcc cacggtgccc aggtaagcca gcccaggcct    780
cgccctccag ctcaaggcgg gacaagagcc ctagagtggc ctgagtccag ggacaggccc    840
cagcagggtg ctgacgcatc cacctccatc ccagatcccc gtaactccca atcttctctc    900
tgcagagccc aaatcttgtg acacacctcc cccgtgccca cggtgcccag gtaagccagc    960
ccaggcctcg ccctccagct caaggcagga caagagccct agagtggcct gagtccaggg    1020
acaggcccca gcagggtgct gacgcgtcca cctccatccc agatccccgt aactcccaat    1080
cttctctctg cagagcccaa atcttgtgac acacctcccc catgcccacg gtgcccaggt    1140
aagccagccc aggcctcgcc ctcagctca aggcgggaca agagcctag agtggcctga    1200 gtccagggac aggccccagc agggtgctga cgcatccacc tccatcccag atccccgtaa    1260
ctcccaatct tctctctgca gagcccaaat cttgtgacac acctccccg tgcccaaggt     1320 gcccaggtaa gccagcccag gcctcgccct ccagctcaag gcaggacagg tgccctagag    1380
tggcctgcat ccagggacag gtcccagtcg ggtgctgaca catctgcctc catctcttcc    1440
tcagcacctg aactcctggg aggaccgtca gtcttcctct tccccccaaa acccaaggat    1500
acccttatga tttcccggac ccctgaggtc acgtgcgtgg tggtggacgt gagccacgaa    1560
gaccccgagg tccagttcaa gtggtacgtg gacggcgtgg aggtgcataa tgccaagaca    1620
aagccgcggg aggagcagta caacagcacg ttccgtgtgg tcagcgtcct caccgtcgtg    1680
caccaggact ggctgaacgg caaggagtac aagtgcaagg tctccaacaa agccctccca    1740 gccccccatcg agaaaaccat ctccaaaacc aaaggtggga cccgcggggt atgagggcca    1800
catggacaga ggccagcttg acccaccctc tgccctggga gtgaccgctg tgccaacctc    1860
tgtccctaca ggacagcccc gagaaccaca ggtgtacacc ctgcccccat cccgggagga    1920
gatgaccaag aaccaggtca gcctgacctg cctggtcaaa ggcttctacc ccagcgacat    1980
cgccgtggag tgggagagca gcgggcagcc ggagaacaac tacaacacca cgcctcccat    2040
gctggactcc gacggctcct tcttcctcta cagcaagctc actgtggaca agagcaggtg    2100
gcagcagggg aacatcttct catgctccgt gatgcatgag gctctgcaca accgcttcac    2160
gcagaagagc ctctccctgt ctccgggtaa atgagtgcga cggccggcaa g             2211
```

<210> SEQ ID NO 79
<211> LENGTH: 2211
<212> TYPE: DNA
<213> ORGANISM: Homo sapiens

<400> SEQUENCE: 79

```
tcacatggcg ccatctctct tgcagcttcc accaagggcc catcggtctt ccccctggcg    60
ccctgctcca ggagcacctc tgggggcaca gcggccctgg gctgcctggt caaggactac   120
ttcccagaac cggtgacggt gtcgtggaac tcaggcgccc tgaccagcgg cgtgcacacc   180
ttcccggctg tcctacagtc ctcaggactc tactccctca gcagcgtggt gaccgtgccc   240
tccagcagct tgggcaccca gacctacacc tgcaacgtga atcacaagcc cagcaacacc   300
aaggtggaca agagagttgg tgagaggcca gcgcaggag ggagggtgtc tgctggaagc    360
caggctcagc cctcctgcct ggacgcatcc cggctgtgca gtcccagccc agggcaccaa   420
ggcaggcccc gtctgactcc tcacccggag gcctctgccc gccccactca tgctcaggga   480
gagggtcttc tggcttttc caccaggctc cgggcaggca caggctggat gcccctaccc   540
caggcccttc acacacaggg gcaggtgctg cgctcagagc tgccaagagc catatccagg   600
aggaccctgc ccctgaccta agcccacccc aaaggccaaa ctctctactc actcagctca   660
gatacccttct ctcttcccag atctgagtaa ctcccaatct tctctctgca gagctcaaaa   720
ccccacttgg tgacacaact cacacatgcc cacggtgccc aggtaagcca gcccaggcct   780
cgccctccag ctcaaggcgg gacaagagcc ctagagtggc ctgagtccag ggacaggccc   840
cagcagggtg ctgacgcatc cacctccatc ccagatcccc gtaactccca atcttctctc   900
tgcagagccc aaatcttgtg acacacctcc ccgtgccca cggtgcccag gtaagcagc    960
ccaggcctcg ccctccagct caaggcagga caagagccct agagtggcct gagtccaggg  1020
acaggcccca gcagggtgct gacgcgtcca cctccatccc agatcccgt aactcccaat   1080
cttctctctg cagagcccaa atcttgtgac acacctcccc catgcccacg gtgcccaggt  1140
aagccagccc aggcctcgcc ctcagctca aggcggaca agagcctag agtggcctga    1200
gtccagggac aggccccagc agggtgctga cgcatccacc tccatcccag atccccgtaa  1260
ctcccaatct tctctctgca gagcccaaat cttgtgacac acctccccg tgcccaaggt   1320
gcccaggtaa gccagcccag gcctcgccct ccagctcaag gcaggacagg tgccctagag  1380
tggcctgcat ccaggacag gtcccagtcg ggtgctgaca catctgcctc catctcttcc   1440
tcagcacctg aactcctggg aggaccgtca gtcttcctct tcccccaaa acccaaggat   1500
acccttatga tttcccggac ccctgaggtc acgtgcgtgg tggtggacgt gagccacgaa  1560
gaccccgagg tccagttcaa gtggtacgtg gacggcgtgg aggtgcataa tgccaagaca  1620
aagccgcggg aggagcagta caacagcacg ttccgtgtgg tcagcgtcct caccgtcctg  1680
caccaggact ggctgaacgg caaggagtac aagtgcaagg tctccaacaa agccctccca  1740
gcccccatcg agaaaaccat ctccaaaacc aaaggtggga cccgcggggt atgagggcca  1800
catggacaga ggccagcttg acccaccctc tgccctggga gtgaccgctg tgccaacctc  1860
tgtccctaca ggacagcccc gagaaccaca ggtgtacacc ctgccccat cccgggagga   1920
gatgaccaag aaccaggtca gcctgacctg cctggtcaaa ggcttctacc ccagcgacat  1980
cgccgtggag tgggagagca gcgggcagcc ggagaacaac tacaacacca cgcctcccat  2040
gctggactcc gacggctcct tcttcctcta cagcaagctc accgtggaca agagcaggtg  2100
gcagcagggg aacatcttct catgctccgt gatgcatgag gctctgcaca accgcttcac  2160
gcagaagagc ctctccctgt ctccgggtaa atgagtgcga cggccggcaa g           2211
```

<210> SEQ ID NO 80
<211> LENGTH: 2211
<212> TYPE: DNA
<213> ORGANISM: Homo sapiens

```
<400> SEQUENCE: 80
tcacatggcg ccatctctct tgcagcttcc accaagggcc catcggtctt ccccctggcg      60
ccctgctcca ggagcacctc tgggggcaca gcggccctgg gctgcctggt caaggactac     120
ttccccgaac cggtgacggt gtcgtggaac tcaggcgccc tgaccagcgg cgtgcacacc     180
ttccggctg tcctacagtc ctcaggactc tactccctca gcagcgtggt gaccgtgccc      240
tccagcagct gggcaccca gacctacacc tgcaacgtga atcacaagcc cagcaacacc      300
aaggtggaca gagagttgg tgagaggcca gcgcagggag ggagggtgtc tgctggaagc      360
caggctcagc cctcctgcct ggacgcatcc cggctgtgca gtcccagccc agggcaccaa     420
ggcaggcccc gtctgactcc tcacccggag gcctctgccc gccccactca tgctcaggga     480
gagggtcttc tggcttttc caccaggctc cgggcaggca caggctggat gcccctaccc      540
caggcccttc acacacaggg gcaggtgctg cgctcagagc tgccaagagc catatccagg     600
aggaccctgc ccctgaccta agcccacccc aaaggccaaa ctctctactc actcagctca     660
gacaccttct ctcttcccag atctgagtaa ctcccaatct tctctctgca gagctcaaaa     720
ccccacttgg tgacacaact cacacatgcc cacggtgccc aggtaagcca gcccaggcct     780
cgccctccag ctcaaggcgg gacaagagcc ctagagtggc ctgagtccag gacaggccc      840
cagcagggtg ctgacgcatc cacctccatc ccagatcccc gtaactccca atcttctctc     900
tgcagagccc aaatcttgtg acacacctcc cccgtgccca cggtgcccag gtaagccagc     960
ccaggcctcg ccctccagct caaggcagga caagagccct agagtggcct gagtccaggg    1020
acaggcccca gcagggtgct gacgcgtcca cctccatccc agatccccgt aactcccaat    1080
cttctctctg cagagcccaa atcttgtgac acacctcccc catgcccacg gtgcccaggt    1140
aagccagccc aggcctcgcc ctccagctca aggcgggaca gagccctag agtggcctga    1200
gtccagggac aggccccagc agggtgctga cgcatccacc tccatcccag atccccgtaa    1260
ctcccaatct tctctctgca gagcccaaat cttgtgacac acctccccca tgcccacggt    1320
gcccaggtaa gccagcccag gcctcgccct ccagctcaag gcaggacagg tgccctagag    1380
tggcctgcat ccagggacag gtcccagtcg ggtgctgaca catctgcctc catctcttcc    1440
tcagcacctg aactcctggg aggaccgtca gtcttcctct tcccccaaa acccaaggat     1500
acccttatga tttccggac ccctgaggtc acgtgcgtgg tggtggacgt gagccacgaa     1560
gaccccgagg tccagttcaa gtggtacgtg gacggcgtgg aggtgcataa tgccaagaca    1620
aagccgcggg aggagcagtt caacagcacg ttccgtgtgg tcagcgtcct caccgtcctg    1680
caccaggact ggctgaacgg caaggagtac aagtgcaagg tctccaacaa agccctccca    1740
gcccccatcg agaaaaccat ctccaaaacc aaaggtggga cccgcgggt atgagggcca    1800
catggacaga ggccagcttg acccacctc tgccctggga gtgaccgctg tgccaacctc    1860
tgtccctaca ggacagcccc gagaaccaca ggtgtacacc ctgccccat cccgggagga    1920
gatgaccaag aaccaggtca gcctgacctg cctggtcaaa ggcttctacc ccagcgacat    1980
cgccgtggag tgggagagca gcgggcagcc ggagaacaac tacaacacca cgcctcccat    2040
gctggactcc gacggctcct tcttcctcta cagcaagctc accgtggaca agagcaggtg    2100
gcagcagggg aacatcttct catgctccgt gatgcatgag gctctgcaca accgcttcac    2160
gcagaagagc ctctccctgt ctccgggtaa atgagtgcga cggccggcaa g             2211

<210> SEQ ID NO 81
<211> LENGTH: 2023
```

<212> TYPE: DNA
<213> ORGANISM: Homo sapiens

<400> SEQUENCE: 81

| | | | | | |
|---|---|---|---|---|---|
| tcacatggcg | ccatctctct | tgcagcttcc | accaagggcc | catcggtctt | cccctggcg | 60 |
| ccctgctcca | ggagcacctc | tgggggcaca | gcggccctgg | gctgcctggt | caaggactac | 120 |
| ttccccgaac | cggtgacggt | gtcgtggaac | tcaggcgccc | tgaccagcgg | cgtgcacacc | 180 |
| ttccggctg | tcctacagtc | ctcaggactc | tactccctca | gcagcgtggt | gaccgtgccc | 240 |
| tccagcagct | tgggcaccca | gacctacacc | tgcaacgtga | atcacaagcc | cagcaacacc | 300 |
| aaggtggaca | agagagttgg | tgagaggcca | gcgcaggga | ggagggtgtc | tgctggaagc | 360 |
| caggctcagc | cctcctgcct | ggacgcatcc | cggctgtgca | gtcccagccc | agggcaccaa | 420 |
| ggcaggcccc | gtctgactcc | tcacccggag | gcctctgccc | gccccactca | tgctcaggga | 480 |
| gagggtcttc | tggcttttc | caccaggctc | cgggcaggca | caggctggat | gcccctaccc | 540 |
| caggcccttc | acacacaggg | gcaggtgctg | cgctcagagc | tgccaagagc | catatccagg | 600 |
| aggaccctgc | ccctgaccta | agcccacccc | aaaggccaaa | ctctctactc | actcagctca | 660 |
| gacaccttct | ctcttcccag | atctgagtaa | ctcccaatct | tctctctgca | gagctcaaaa | 720 |
| ccccacttgg | tgacacaact | cacacatgcc | cacggtgccc | aggtaagcca | gcccaggcct | 780 |
| cgccctccag | ctcaaggcgg | gacaagagcc | ctagagtggc | ctgagtccag | ggacaggccc | 840 |
| cagcagggtg | ctgacgcatc | cacctccatc | ccagatcccc | gtaactccca | atcttctctc | 900 |
| tgcagagccc | aaatcttgtg | acacacctcc | ccgtgccca | cggtgcccag | gtaagccagc | 960 |
| ccaggcctcg | ccctccagct | caaggcagga | caagagccct | agagtggcct | gagtccaggg | 1020 |
| acaggcccca | gcagggtgct | gacgcgtcca | cctccatccc | agatcccgt | aactcccaat | 1080 |
| cttctctctg | cagagcccaa | atcttgtgac | acacctcccc | catgcccacg | gtgcccaggt | 1140 |
| aagccagccc | aggcctcgcc | ctccagctca | aggcaggaca | ggtgcccctag | agtggcctgc | 1200 |
| atccagggac | aggtcccagt | cgggtgctga | cacatctgcc | tccatctctt | cctcagcacc | 1260 |
| tgaactcctg | ggaggaccgt | cagtcttcct | cttccccca | aaacccaagg | ataccctat | 1320 |
| gatttcccgg | acccctgagg | tcacgtgcgt | ggtggtggac | gtgagccacg | aagacccga | 1380 |
| ggtccagttc | aagtggtacg | tggacggcgt | ggaggtgcat | aatgccaaga | caaagccgcg | 1440 |
| ggaggagcag | ttcaacagca | cgttccgtgt | ggtcagcgtc | ctcaccgtcc | tgcaccagga | 1500 |
| ctggctgaac | ggcaaggagt | acaagtgcaa | ggtctccaac | aaagccctcc | cagcccccat | 1560 |
| cgagaaaacc | atctccaaaa | ccaaaggtgg | gacccgcggg | gtatgagggc | cacatggaca | 1620 |
| gaggccagct | tgacccaccc | tctgccctgg | gagtgaccgc | tgtgccaacc | tctgtcccta | 1680 |
| caggacagcc | ccgagaacca | caggtgtaca | ccctgccccc | atcccgggag | gagatgacca | 1740 |
| agaaccaggt | cagcctgacc | tgcctggtca | aaggcttcta | ccccagcgac | atcgccgtgg | 1800 |
| agtgggagag | cagcgggcag | ccggagaaca | actacaacac | cacgcctccc | atgctggact | 1860 |
| ccgacggctc | cttcttcctc | tacagcaagc | tcaccgtgga | caagagcagg | tggcagcagg | 1920 |
| ggaacatctt | ctcatgctcc | gtgatgcatg | aggctctgca | caaccgcttc | acgcagaaga | 1980 |
| gcctctccct | gtctccgggt | aaatgagtgc | gacggccggc | aag | 2023 |

<210> SEQ ID NO 82
<211> LENGTH: 2211
<212> TYPE: DNA
<213> ORGANISM: Homo sapiens

<400> SEQUENCE: 82

```
tcacatggcg ccatctctct tgcagcttcc accaagggcc catcggtctt ccccctggcg      60
ccctgctcca ggagcacctc tgggggcaca gcggccctgg gctgcctggt caaggactac     120
ttccccgaac cggtgacggt gtcgtggaac tcaggcgccc tgaccagcgg cgtgcacacc     180
ttcccggctg tcctacagtc ctcaggactc tactccctca gcagcgtggt gaccgtgccc     240
tccagcagct tgggcaccca gacctacacc tgcaacgtga atcacaagcc cagcaacacc     300
aaggtggaca agagagttgg tgagaggcca gcgcaggag ggagggtgtc tgctggaagc      360
caggctcagc cctcctgcct ggacgcatcc cggctgtgca gtcccagccc agggcaccaa     420
ggcaggcccc gtctgactcc tcacccggag gcctctgccc gccccactca tgctcaggga     480
gagggtcttc tggcttttc caccaggctc cgggcaggca caggctggat gcccctaccc      540
caggccttc acacacaggg gcaggtgctg cgctcagagc tgccaagagc catatccagg      600
aggaccctgc ccctgaccta agcccacccc aaaggccaaa ctctctactc actcagctca     660
gacaccttct ctcttcccag atctgagtaa ctcccaatct tctctctgca gagctcaaaa     720
ccccacttgg tgacacaact cacacatgcc cacggtgccc aggtaagcca gcccaggcct     780
cgccctccag ctcaaggcgg gacaagagcc ctagagtggc ctgagtccag gacaggccc     840
cagcagggtg ctgacgcatc cacctccatc ccagatcccc gtaactccca atcttctctc     900
tgcagagccc aaatcttgtg acacacctcc ccgtgccca cggtgcccag gtaagccagc      960
ccaggcctcg ccctccagct caaggcagga caagagccct agagtggcct gagtccaggg    1020
acaggcccca gcagggtgct gacgcgtcca cctccatccc agatcccgt aactcccaat     1080
cttctctctg cagagcccaa atcttgtgac acacctcccc catgcccacg gtgcccaggt    1140
aagccagccc aggcctcgcc ctccagctca aggcggaca agagcccctag agtggcctga    1200
gtccagggac aggccccagc agggtgctga cgcatccacc tccatcccag atccccgtaa    1260
ctcccaatct tctctctgca gagcccaaat cttgtgacac acctcccccg tgcccaaggt    1320
gcccaggtaa gccagcccag gcctcgccct ccagctcaag gcaggacagg tgccctagag    1380
tggcctgcat ccagggacag gtcccagtcg ggtgctgaca catctgcctc catctcttcc    1440
tcagcacctg aactcctggg aggaccgtca gtcttcctct tccccccaaa acccaaggat    1500
acccttatga tttcccggac ccctgaggtc acgtgcgtgg tggtggacgt gagccacgaa    1560
gaccccgagg tccagttcaa gtggtacgtg gacggcgtgg aggtgcataa tgccaagaca    1620
aagccgcggg aggagcagta acagcacg ttcgtgtgg tcagcgtcct caccgtcctg       1680
caccaggact ggctgaacgg caaggagtac aagtgcaagg tctccaacaa agccctccca    1740
gcccccatcg agaaaaccat ctccaaaacc aaaggtggga cccgcggggt atgagggcca    1800
catggacaga ggccagcttg acccaccctc tgccctggga gtgaccgctg tgccaacctc    1860
tgtccctaca ggacagcccc gagaaccaca ggtgtacacc ctgccccat cccgggagga     1920
gatgaccaag aaccaggtca gcctgacctg cctggtcaaa ggcttctacc ccagcgacat    1980
cgccgtggag tgggagagca gcgggcagcc ggagaacaac tacaagacca cacctcccat    2040
gctggactcc gacggctcct tcttcctcta cagcaagctc accgtggaca gagcaggtg     2100
gcaggagggg aacatcttct catgctccgt gatgcatgag gctctgcaca accgcttcac    2160
gcagaagagc ctctccctgt ctccgggtaa atgagtgcga cggccggcaa g             2211
```

<210> SEQ ID NO 83
<211> LENGTH: 2211
<212> TYPE: DNA
<213> ORGANISM: Homo sapiens

<400> SEQUENCE: 83

```
tcacatggcg ccatctctct tgcagcttcc accaagggcc catcggtctt cccctggcg      60
ccctgctcca ggagcacctc tgggggcaca gcggccctgg gctgcctggt caaggactac    120
ttccccgaac cggtgacggt gtcgtggaac tcaggcgccc tgaccagcgg cgtgcacacc    180
ttccggctg tcctacagtc ctcaggactc tactccctca gcagcgtggt gaccgtgccc     240
tccagcagct gggcaccca gacctacacc tgcaacgtga atcacaagcc cagcaacacc     300
aaggtggaca gagagttgg tgagaggcca gcgcagggag ggagggtgtc tgctggaagc     360
caggctcagc cctcctgcct ggacgcatcc cggctgtgca gtcccagccc agggcaccaa    420
ggcaggcccc gtctgactcc tcacccggag gcctctgccc gccccactca tgctcaggga    480
gagggtcttc tggctttttc caccaggctc cgggcaggca caggctggat gcccctaccc    540
caggcccttc acacacaggg gcaggtgctg cgctcagagc tgccaagagc catatccagg    600
aggaccctgc ccctgaccta gcccacccc aaaggccaaa ctctctactc actcagctca    660
gacaccttct ctcttcccag atctgagtaa ctcccaatct tctctctgca gagctcaaaa    720
ccccacttgg tgacacaact cacacatgcc cacggtgccc aggtaagcca gcccaggcct    780
cgccctccag ctcaaggcgg gacaagagcc ctagagtggc ctgagtccag ggacaggccc    840
cagcagggtg ctgacgcatc cacctccatc ccagatcccc gtaactccca atcttctctc    900
tgcagagccc aaatcttgtg acacacctcc cccgtgccca cggtgcccag gtaagccagc    960
ccaggcctcg ccctccagct caaggcagga caagagccct agagtggcct gagtccaggg   1020
acaggcccca gcagggtgct gacgcgtcca cctccatccc agatccccgt aactcccaat   1080
cttctctctg cagagcccaa atcttgtgac acacctcccc catgcccacg tgcccaggt    1140
aagccagccc aggcctcgcc ctcagctca aggcgggaca agagcctag agtggcctga    1200
gtccagggac aggccccagc agggtgctga cgcatccacc tccatcccag atccccgtaa   1260
ctcccaatct tctctctgca gagcccaaat cttgtgacac acctcccccg tgcccaaggt   1320
gcccaggtaa gccagcccag gcctcgccct ccagctcaag gcaggacagg tgccctagag   1380
tggcctgcat ccagggacag gtcccagtcg ggtgctgaca catctgcctc catctcttcc   1440
tcagcacctg aactcctggg aggaccgtca gtcttcctct tccccccaaa acccaaggat   1500
acccttatga tttcccggac ccctgaggtc acgtgcgtgg tggtggacgt gagccacgaa   1560
gaccccgagg tccagttcaa gtggtacgtg gacggcgtgg aggtgcataa tgccaagaca   1620
aagctgcggg aggagcagta caacagcacg ttccgtgtgg tcagcgtcct caccgtcctg   1680
caccaggact ggctgaacgg caaggagtac aagtgcaagg tctccaacaa agccctccca   1740
gcccccatcg agaaaaccat ctccaaaacc aaaggtggga cccgcggggt atgagggcca   1800
catggacaga ggccagcttg acccaccctc tgccctggga gtgaccgctg tgccaacctc   1860
tgtccctaca ggacagcccc gagaaccaca ggtgtacacc ctgcccccat cccgggagga   1920
gatgaccaag aaccaggtca gcctgacctg cctggtcaaa ggcttctacc ccagcgacat   1980
cgccgtggag tgggagagca atgggcagcc ggagaacaac tacaacacca cgcctcccat   2040
gctggactcc gacggctcct tcttcctcta cagcaagctc accgtggaca agagcaggtg   2100
gcagcagggg aacatcttct catgctccgt gatgcatgag gctctgcaca accgctacac   2160
gcagaagagc ctctccctgt ctccgggtaa atgagtgcca tggccggcaa g            2211
```

<210> SEQ ID NO 84
<211> LENGTH: 2211

<212> TYPE: DNA
<213> ORGANISM: Homo sapiens

<400> SEQUENCE: 84

```
tcacatggcg ccatctctct tgcagcttcc accaagggcc catcggtctt ccccctggcg      60
ccctgctcca ggagcacctc tgggggcaca gcggccctgg gctgcctggt caaggactac     120
ttccccgaac cggtgacggt gtcgtggaac tcaggcgccc tgaccagcgg cgtgcacacc     180
ttcccggctg tcctacagtc ctcaggactc tactccctca gcagcgtggt gaccgtgccc     240
tccagcagct tgggcaccca gacctacacc tgcaacgtga atcacaagcc cagcaacacc     300
aaggtggaca agagagttgg tgagaggcca gcgcaggggag ggagggtgtc tgctggaagc     360
caggctcagc cctcctgcct ggacgcatcc cggctgtgca gtcccagccc agggcaccaa     420
ggcaggcccc gtctgactcc tcacccggag gcctctgccc gccccactca tgctcaggga     480
gagggtcttc tggcttttc caccaggctc cgggcaggca caggctggat gccctaccc     540
caggcccttc acacacaggg gcaggtgctg cgctcagagc tgccaagagc catatccagg     600
aggaccctgc ccctgaccta agcccacccc aaaggccaaa ctctctactc actcagctca     660
gacaccttct ctcttcccag atctgagtaa ctcccaatct tctctctgca gagctcaaaa     720
ccccacttgg tgacacaact cacacatgcc cacggtgccc aggtaagcca gcccaggcct     780
cgccctccag ctcaaggcgg gacaagagcc ctagagtggc ctgagtccag ggacaggccc     840
cagcagggtg ctgacgcatc cacctccatc ccagatcccc gtaactccca atcttctctc     900
tgcagagccc aaatcttgtg acacacctcc ccgtgccca cggtgcccag gtaagccagc     960
ccaggcctcg ccctccagct caaggcagga caagagccct agagtggcct gagtccaggg    1020
acaggcccca gcagggtgct gacgcgtcca cctccatccc agatcccgt aactcccaat    1080
cttctctctg cagagcccaa atcttgtgac acacctcccc catgcccacg gtgcccaggt    1140
aagccagccc aggcctcgcc ctccagctca aggcgggaca agagcctag agtggcctga    1200
gtccagggac aggcccagc agggtgctga cgcatccacc tccatcccag atccccgtaa    1260
ctcccaatct tctctctgca gagcccaaat cttgtgacac acctccccg tgcccaaggt    1320
gcccaggtaa gccagcccag gcctcgccct ccagctcaag gcaggacagg tgccctagag    1380
tggcctgcat ccagggacag gtcccagtcg ggtgctgaca catctgcctc catctcttcc    1440
tcagcacctg aactcctggg aggaccgtca gtcttcctct tccccccaaa acccaaggat    1500
acccttatga tttcccggac ccctgaggtc acgtgcgtgg tggtggacgt gagccacgaa    1560
gaccccgagg tccagttcaa gtggtacgtg gacggcgtgg aggtgcataa tgccaagaca    1620
aagctgcggg aggagcagta caacagcacg ttcgtgtggt cagcgtcct caccgtcctg    1680
caccaggact ggctgaacgg caaggagtac aagtgcaagg tctccaacaa agccctccca    1740
gcccccatcg agaaaaccat ctccaaaacc aaaggtggga cccgcggggt atgagggcca    1800
catggacaga ggccagcttg acccaccctc tgccctggga gtgaccgctg tgccaacctc    1860
tgtccctaca ggacagcccc gagaaccaca ggtgtacacc ctgccccat cccgggagga    1920
gatgaccaag aaccaggtca gcctgacctg cctggtcaaa ggcttctacc ccagcgacat    1980
cgccgtggag tgggagagca atgggcagcc ggagaacaac tacaagacca cgcctcccat    2040
gctggactcc gacggctcct tcttcctcta cagcaagctc accgtggaca gagcaggtg    2100
gcagcagggg aacatcttct catgctccgt gatgcatgag gctctgcaca accgctacac    2160
gcagaagagc ctctccctgt ctccgggtaa atgagtgcca tggccggcaa g            2211
```

<210> SEQ ID NO 85
<211> LENGTH: 2211
<212> TYPE: DNA
<213> ORGANISM: Homo sapiens

<400> SEQUENCE: 85

| | | | | | |
|---|---|---|---|---|---|
| tcacatggcg | ccatctctct | tgcagcttcc | accaagggcc | catcggtctt | ccccctggcg | 60 |
| ccctgctcca | ggagcacctc | tgggggcaca | gcggccctgg | gctgcctggt | caaggactac | 120 |
| ttccccgaac | cggtgacggt | gtcgtggaac | tcaggcgccc | tgaccagcgg | cgtgcacacc | 180 |
| ttccggctg | tcctacagtc | ctcaggactc | tactccctca | gcagcgtggt | gaccgtgccc | 240 |
| tccagcagct | tgggcaccca | gacctacacc | tgcaacgtga | atcacaagcc | cagcaacacc | 300 |
| aaggtggaca | agagagttgg | tgagaggcca | gcgcagggag | ggagggtgtc | tgctggaagc | 360 |
| caggctcagc | cctcctgcct | ggacgcatcc | cggctgtgca | gtcccagccc | agggcaccaa | 420 |
| ggcaggcccc | gtctgactcc | tcacccggag | gcctctgccc | gccccactca | tgctcaggga | 480 |
| gagggtcttc | tggcttttc | caccaggctc | cgggcaggca | caggctggat | gcccctaccc | 540 |
| caggcccttc | acacacaggg | gcaggtgctg | cgctcagagc | tgccaagagc | catatccagg | 600 |
| aggaccctgc | ccctgaccta | agcccacccc | aaaggccaaa | ctctctactc | actcagctca | 660 |
| gacaccttct | ctcttcccag | atctgagtaa | ctcccaatct | tctctctgca | gagctcaaaa | 720 |
| ccccacttgg | tgacacaact | cacacatgcc | cacggtgccc | aggtaagcca | gcccaggcct | 780 |
| cgccctccag | ctcaaggcgg | gacaagagcc | ctagagtggc | ctgagtccag | ggacaggccc | 840 |
| cagcagggtg | ctgacgcatc | cacctccatc | ccagatcccc | gtaactccca | atcttctctc | 900 |
| tgcagagccc | aaatcttgtg | acacacctcc | cccgtgccca | cggtgcccag | gtaagccagc | 960 |
| ccaggcctcg | ccctccagct | caaggcagga | caagagccct | agagtggcct | gagtccaggg | 1020 |
| acaggcccca | gcagggtgct | gacgcgtcca | cctccatccc | agatccccgt | aactcccaat | 1080 |
| cttctctctg | cagagcccaa | atcttgtgac | acacctcccc | catgcccacg | gtgcccaggt | 1140 |
| aagccagccc | aggcctcgcc | ctccagctca | aggcgggaca | agagccctag | agtggcctga | 1200 |
| gtccagggac | aggccccagc | agggtgctga | cgcatccacc | tccatcccag | atccccgtaa | 1260 |
| ctcccaatct | tctctctgca | gagcccaaat | cttgtgacac | acctcccccg | tgcccaaggt | 1320 |
| gcccaggtaa | gccagcccag | gcctcgccct | ccagctcaag | gcaggacagg | tgccctagag | 1380 |
| tggcctgcat | ccagggacag | gtcccagtcg | ggtgctgaca | catctgcctc | catctcttcc | 1440 |
| tcagcacctg | aactcctggg | aggaccgtca | gtcttcctct | tccccccaaa | acccaaggat | 1500 |
| acccttatga | tttcccggac | ccctgaggtc | acgtgcgtgg | tggtggacgt | gagccacgaa | 1560 |
| gaccccgagg | tccagttcaa | gtggtacgtg | gacggcgtgg | aggtgcataa | tgccaagaca | 1620 |
| aagctgcggg | aggagcagta | caacagcacg | ttccgtgtgg | tcagcgtcct | caccgtcctg | 1680 |
| caccaggact | ggctgaacgg | caaggagtac | aagtgcaagg | tctccaacaa | agccctccca | 1740 |
| gcccccatcg | agaaaaccat | ctccaaagcc | aaaggtggga | cccgcggggt | atgagggcca | 1800 |
| cgtggacaga | ggccagcttg | acccaccctc | tgccctggga | gtgaccgctg | tgccaacctc | 1860 |
| tgtccctaca | ggacagcccc | gagaaccaca | ggtgtacacc | ctgcccccat | cccgggagga | 1920 |
| gatgaccaag | aaccaggtca | gcctgacctg | cctggtcaaa | ggcttctacc | ccagcgacat | 1980 |
| cgccgtggag | tgggagagca | atgggcagcc | ggagaacaac | tacaacacca | cgcctcccat | 2040 |
| gctggactcc | gacggctcct | tcttcctcta | cagcaagctc | accgtggaca | agagcaggtg | 2100 |
| gcagcagggg | aacatcttct | catgctccgt | gatgcatgag | gctctgcaca | accgctacac | 2160 |
| gcagaagagc | ctctccctgt | ctccgggtaa | atgagtgcca | tggccggcaa | g | 2211 |

<210> SEQ ID NO 86
<211> LENGTH: 2023
<212> TYPE: DNA
<213> ORGANISM: Homo sapiens

<400> SEQUENCE: 86

```
tcacatggcg ccatctctct tgcagcttcc accaagggcc catcggtctt ccccctggcg      60
ccctgctcca ggagcacctc tggggcaca  gcggccctgg gctgcctggt caaggactac     120
ttccccgaac cggtgacggt gtcgtggaac tcaggcgccc tgaccagcgg cgtgcacacc     180
ttcccggctg tcctacagtc ctcaggactc tactccctca gcagcgtggt gaccgtgccc     240
tccagcaact tcggcaccca gacctacacc tgcaacgtga atcacaagcc cagcaacacc     300
aaggtggaca agagagttgg tgagaggcca gcgcaggag  ggagggtgtc tgctggaagc     360
caggctcagc gctcctgcct ggacgcatcc cggctgtgca gtcccagccc agggcaccaa     420
ggcaggcccc gtctgactcc tcacccggag gcctctgccc gccccactca tgctcaggga     480
gagggtcttc tggcttttc  caccaggctc cgggcaggca caggctggat gcccctaccc     540
caggcccttc acacacaggg gcaggtgctg cgctcagagc tgccaagagc catatccagg     600
aggaccctgc ccctgaccta agcccacccc aaaggccaaa ctctctactc actcagctca     660
gacaccttct ctcttcccag atctgagtaa ctcccaatct tctctctgca gagctcaaaa     720
ccccacttgg tgacacaact cacacatgcc cacggtgccc aggtaagcca gcccaggcct     780
cgccctccag ctcaaggcgg gacaagagcc ctagagtggc ctgagtccag ggacaggccc     840
cagcagggtg ctgacgcgtc cacctccatc ccagatcccc gtaactccca atcttctctc     900
tgcagagccc aaatcttgtg acacacctcc ccgtgcccaa cggtgcccag gtaagccagc     960
ccaggcctcg ccctccagct caaggcggga caagagccct agagtggcct gagtccaggg    1020
acaggcccca gcagggtgct gacgcatcca cctccatccc agatcccgt  aactcccaat    1080
cttctctctg cagagcccaa atcttgtgac acacctcccc cgtgcccaag gtgcccaggt    1140
aagccagccc aggcctcgcc ctcagctca  aggcaggaca ggtgcccag  agtggcctgc    1200
atccagggac aggtccagt  cgggtgctga cacatctgcc tccatctctt cctcagcacc    1260
tgaactcctg ggaggaccgt cagtcttcct cttcccccca aaacccaagg atacccttat    1320
gatttcccgg accctgagg  tcacgtgcgt ggtggtggac gtgagccacg aagaccccga    1380
ggtccagttc aagtggtacg tggacggcgt ggaggtgcat aatgccaaga caaagccgcg    1440
ggaggagcag tacaacagca cgttccgtgt ggtcagcgtc ctcaccgtcc tgcaccagga    1500
ctggctgaac ggcaaggagt acaagtgcaa ggtctccaac aaagccctcc cagcccccat    1560
cgagaaaacc atctccaaaa ccaaaggtgg gacccgcggg gtatgagggc cacatggaca    1620
gaggccagct tgacccaccc tctgccctgg gagtgaccgc tgtgccaacc tctgtccctac    1680
caggacagcc ccgagaacca caggtgtaca ccctgccccc atcccgggag gagatgacca    1740
agaaccaggt cagcctgacc tgcctggtca aaggcttcta ccccagcgac atcgccatgg    1800
agtgggagag cagcggcag  ccggagaaca actacaagac cacgcctccc gtgctggact    1860
ccgacggctc cttcttcctc tacagcaagc tcaccgtgga caagagcagg tggcagcagg    1920
ggaacatctt ctcatgctcc gtgatgcatg aggctctgca caaccactac acgcagaaga    1980
gcctctccct gtctccgggt aaatgagtgc gacggccggc aag                      2023
```

<210> SEQ ID NO 87
<211> LENGTH: 2023

<212> TYPE: DNA
<213> ORGANISM: Homo sapiens

<400> SEQUENCE: 87

```
tcacatggcg ccatctctct tgcagcttcc accaagggcc catcggtctt ccccctggcg      60
ccctgctcca ggagcacctc tgggggcaca gcggccctgg gctgcctggt caaggactac    120
ttccccgaac cggtgacggt gtcgtggaac tcaggcgccc tgaccagcgg cgtgcacacc    180
ttcccggctg tcctacagta ctcaggactc tactccctca gcagcgtggt gaccgtgccc    240
tccagcagct tgggcaccca gacctacacc tgcaacgtga atcacaagcc cagcaacacc    300
aaggtggaca agagagttgg tgagaggcca gcgcaggag ggagggtgtc tgctggaagc     360
caggctcagc cctcctgcct ggacgcatcc cggctgtgca gtcccagccc agggcaccaa    420
ggcaggcccc gtctgactcc tcacccggag gcctctgccc gccccactca tgctcaggga    480
gagggtcttc tggcttttc caccaggctc cgggcaggca caggctggat gcccctaccc     540
caggcccttc acacacaggg gcaggtgctg cgctcagagc tgccaagagc catatccagg    600
aggaccctgc ccctgaccta agcccacccc aaaggccaaa ctctctactc actcagctca    660
gacaccttct ctcttcccag atctgagtaa ctcccaatct tctctctgca gagctcaaaa    720
ccccacttgg tgacacaact cacacatgcc cacggtgccc aggtaagcca gcccaggcct    780
cgccctccag ctcaaggcgg gacaagagcc ctagagtggc ctgagtccag ggacaggccc    840
cagcagggtg ctgacgcgtc cacctccatc ccagatcccc gtaactccca atcttctctc    900
tgcagagccc aaatcttgtg acacacctcc ccgtgcccca cggtgcccag gtaagccagc    960
ccaggcctcg ccctccagct caaggcggga caagagccct agagtggcct gagtccaggg   1020
acaggcccca gcagggtgct gacgcatcca cctccatccc agatcccgt aactcccaat    1080
cttctctctg cagagcccaa atcttgtgac acacctcccc gtgcccaag gtgcccaggt     1140
aagccagccc aggcctcgcc ctcagctca aggcaggaca ggtgcccctag agtggcctgc   1200
atccagggac aggtcccagt cgggtgctga cacatctgcc tccatctctt cctcagcacc   1260
tgaactcctg ggaggaccgt cagtcttcct cttccccca aaacccaagg ataccttat     1320
gatttcccgg acccctgagg tcacgtgcgt ggtggtggac gtgagccacg aagacccga    1380
ggtccagttc aagtggtacg tggacggcgt ggaggtgcat aatgccaaga caaagccgtg   1440
ggaggagcag tacaacagca cgttccgtgt ggtcagcgtc ctcaccgtcc tgcaccagga   1500
ctggctgaac ggcaaggagt acaagtgcaa ggtctccaac aaagccctcc cagccccat    1560
cgagaaaacc atctccaaaa ccaaaggtgg gacccgcggg gtatgagggc cacatggaca   1620
gaggccagct tgacccaccc tctgccctgg gagtgaccac tgtgccaacc tctgtcccta   1680
caggacagcc ccgagaacca caggtgtaca ccctgccccc atcccgggag gagatgacca   1740
agaaccaggt cagcctgacc tgcctggtca aaggcttcta ccccagcgac atcgccatgg   1800
agtgggagag cagcggcag ccggagaaca actacaagac cacgcctccc gtgctggact   1860
ccgacggctc cttcttcctc tacagcaagc tcaccgtgga caagagcagg tggcagcagg   1920
ggaacatctt ctcatgctcc gtgatgcatg aggctctgca caaccactac acgcagaaga   1980
gcctctccct gtctccgggt aaatgagtgc gacggccggc aag                      2023
```

<210> SEQ ID NO 88
<211> LENGTH: 2023
<212> TYPE: DNA
<213> ORGANISM: Homo sapiens

<400> SEQUENCE: 88

```
tcacatggcg ccatctctct tgcagcttcc accaagggcc catcggtctt ccccctggcg    60
ccctgctcca ggagcacctc tgggggcaca gcggccctgg gctgcctggt caaggactac   120
ttccccgaac cggtgacggt gtcgtggaac tcaggcgccc tgaccagcgg cgtgcacacc   180
ttcccggctg tcctacagtc ctcaggactc tactccctca gcagcgtggt gaccgtgccc   240
tccagcagct tgggcaccca gacctacacc tgcaacgtga atcacaagcc cagcaacacc   300
aaggtggaca gagagttgg tgagaggcca gcgcagggag ggagggtgtc tgctggaagc   360
caggctcagc cctcctgcct ggacgcatcc cggctgtgca gtcccagccc agggcaccaa   420
ggcaggcccc gtctgactcc tcacccggag gcctctgccc gccccactca tgctcaggga   480
gagggtcttc tggcttttc caccaggctc cgggcaggca caggctggat gcccctaccc   540 caggccttc acacacaggg gcaggtgctg cgctcagagc tgccaagagc catatccagg   600 aggacctgc ccctgaccta agcccacccc aaaggccaaa ctctctactc actcagctca   660
gacaccttct ctcttcccag atctgagtaa ctcccaatct tctctctgca gagctcaaaa   720
ccccacttgg tgacacaact cacacatgcc cacggtgccc aggtaagcca gcccaggcct   780
cgccctccag ctcaaggcgg gacaagagcc ctagagtggc ctgagtccag ggacaggccc   840
cagcagggtg ctgacgcgtc cacctccatc ccagatcccc gtaactccca atcttctctc   900
tgcagagccc aaatcttgtg acacacctcc cccgtgccca cggtgcccag gtaagccagc   960
ccaggcctcg ccctccagct caaggcggga caagagccct agagtggcct gagtccaggg   1020
acaggcccca gcagggtgct gacgcatcca cctccatccc agatcccgt aactcccaat   1080 cttctctctg cagagcccaa atcttgtgac acacctcccc gtgcccaag gtgcccaggt   1140 aagccagccc aggcctcgcc ctcagctca aggcaggaca ggtgccctag agtggcctgc   1200
atccagggac aggtccagt cgggtgctga cacatctgcc tccatctctt cctcagcacc   1260
tgaactcctg ggaggaccgt cagtcttcct cttcccccca aaacccaagg atacccttat   1320
gatttcccgg acccctgagg tcacgtgcgt ggtggtggac gtgagccacg aagaccccga   1380
ggtccagttc aagtggtacg tggacggcgt ggaggtgcat aatgccaaga caaagccgtg   1440
ggaggagcag tacaacagca cgttccgtgt ggtcagcgtc ctcaccgtcc tgcaccagga   1500
ctggctgaac ggcaaggagt acaagtgcaa ggtctccaac aaagccctcc cagccccat   1560 cgagaaaacc atctccaaaa ccaaaggtgg gacccgcggg gtatgagggc cacatggaca   1620
gaggccagct tgacccaccc tctgccctgg gagtgaccac tgtgccaacc tctgtcccta   1680
caggacagcc ccgagaacca caggtgtaca ccctgccccc atcccgggag gagatgacca   1740
agaaccaggt cagcctgacc tgcctggtca aaggcttcta ccccagcgac atcgccatgg   1800
agtgggagag cagcgggcag ccggagaaca actacaagac cacgcctccc gtgctggact   1860
ccgacggctc cttcttcctc tacagcaagc tcaccgtgga caagagcagg tggcagcagg   1920
ggaacatctt ctcatgctcc gtgatgcatg aggctctgca caaccactac acgcagaaga   1980
gcctctccct gtctccgggt aaatgagtgc gacggccggc aag                    2023
```

STABILIZED HUMAN IGG2 AND IGG3 ANTIBODIES

TECHNICAL FIELD

The present invention relates to IgG2 and IgG3 antibodies improved in stability, which are obtained by introducing a variation into the constant regions of human IgG2 and IgG3 heavy chains.

BACKGROUND ART

Immunoglobulins, which are glycoproteins present in the serum, tissue, or body fluid of every mammal, have the function of recognizing foreign antigens. The immunoglobulins participate through antibody binding to antigens in biophylaxis via the activation of the complement system or via the activation of effector functions such as enhancement in cellular phagocytosis, antibody-dependent cytotoxicity, mediator release, and antigen presentation via an Fc receptor (FcR) present in cell surface.

Human immunoglobulins are divided into 5 different classes consisting of IgG, IgA, IgM, IgD, and IgE. IgG can further be classified into 4 subclasses consisting of IgG1, IgG2, IgG3, and IgG4, while IgA can further be classified into 2 subclasses consisting of IgA1 and IgA2. The basic structure of immunoglobulin comprises 2 homologous light chains (L chains) and 2 homologous heavy chains (H chains). The immunoglobulin classes and subclasses are determined depending on H chains.

Different types of immunoglobulins are known to have different functions. For example, complement-binding ability is high in IgM>IgG3>IgG1>IgG2 in this order, and affinity for Fc receptor I is high in IgG3>IgG1>IgG4>IgG2 in this order. Moreover, IgG1, IgG2, and IgG4 are capable of binding to Protein A.

Human antibodies used as drugs are collected and purified from blood. Many monoclonal antibodies have undergone clinical trials in recent years and have been placed on the market. However, the monoclonal antibodies placed on the market or clinically developed for pharmaceutical applications are mostly derived from the IgG1 subclass and hardly derived from the IgG2 and IgG3 subclasses. IgG2 is only one IgG that can activate the alternative pathway in complement activation and has been reported to be associated with infectious diseases such as influenza. IgG2 is also known to have little antibody-dependent cytotoxicity. On the other hand, IgG3 is known to have very strong antibody-dependent complement-activating capacity and antibody-dependent cytotoxicity. The development of antibody drugs having novel activity can be expected by exploiting such characteristics.

However, IgG2 and IgG3 have hardly been developed so far as drugs. Therefore, production techniques thereof mostly remain uncertain.

DISCLOSURE OF THE INVENTION

An object of the present invention is to prepare highly stable variants of human IgG2 and IgG3 antibodies.

The present inventors have found that IgG2 and IgG3 antibodies are instable at low pH, specifically, tend to form aggregates at low pH.

In general, an affinity purification method using Protein A is used in the production of antibodies as drugs. In this method, a buffer solution with low pH is often used to elute the antibodies bound with Protein A. Moreover, the treatment at low pH for a given time is also preferable in light of virus removal. The contamination of drugs with aggregates formed during this procedure has been reported to promote infusion reaction, complement activation, or antibody-dependent cytotoxicity. It can be estimated easily that these factors lead to side-effects. Therefore, it is very important to reduce the amount of aggregates as much as possible.

Thus, the present inventors have found that aggregate formation at low pH can be suppressed by changing the partial amino acid structures of the heavy chain constant regions of IgG2 and IgG3 antibodies.

The basic idea of modifications of human IgG2 and IgG3 antibodies according to the present invention will be described below in detail. A stabilized human IgG2 antibody of the present invention has at least a substitution of Y for F at the 300th position (the alphabet denotes the single character code of the amino acid; the number denotes the EU index of Kabat et al.; hereinafter, interpreted in the same manner), L for V at the 309th position, or A for T at the 339th position designated by the EU index of Kabat et al. (Kabat et al., Sequences of proteins of Immunological Interest, 1991 Fifth edition) in the heavy chain constant region thereof. Preferably, the antibody has at least the substitutions of Y for F at the 300th position and L for V at the 309th position designated by the EU index of Kabat et al. Alternatively, preferably, the antibody has at least the substitutions of Y for F at the 300th position and A for T at the 339th position designated by the EU index of Kabat et al. Alternatively, preferably, the antibody has at least the substitutions of L for V at the 309th position and A for T at the 339th position designated by the EU index of Kabat et al. Further preferably, the antibody has at least the substitutions of Y for F at the 300th position, L for V at the 309th position, and A for T at the 339th position designated by the EU index of Kabat et al.

Moreover, the stabilized human IgG2 antibody of the present invention has at least a substitution of the CH2 domain of an IgG1 heavy chain for the CH2 domain of the heavy chain constant region thereof. For example, the CH2 domain is substituted by the CH2 domain of an IgG1 heavy chain, or the CH2 and CH3 domains are substituted by the CH2 and CH3 domains of an IgG1 heavy chain.

Further substitutions of A for D270, K322, P329, and P331 or conversion of P331 to S or G (the alphabet denotes the single character code of the amino acid; the number denotes the EU index of Kabat et al. (Kabat et al., Sequences of proteins of Immunological Interest, 1991 Fifth edition)) can improve stability and reduce CDC activity.

Moreover, further substitutions of E for L235 and A for G237 can improve stability and reduce ADCC activity. Conversely, a variation for enhancing CDC activity and/or ADCC activity can be introduced appropriately.

A stabilized human IgG3 antibody of the present invention has at least a substitution of K for N at the 392nd or V for M at the 397th position designated by the EU index of Kabat et al. in the heavy chain constant region thereof. Preferably, the antibody has at least the substitutions of K for N at the 392nd position and V for M at the 397th position designated by the EU index of Kabat et al.

Alternatively, preferably, the antibody has the substitution(s) at the 392nd and/or 397th positions and further has a substitution of Y for F at the 300th position designated by the EU index of Kabat et al.

Alternatively, preferably, the antibody has the substitutions at the 392nd, 397th, and 300th positions and further has a substitution of H for R at the 435th position designated by the EU index of Kabat et al. For example, the antibody has the substitutions at the 392nd and 435th positions, the substitutions at the 397th and 435th positions, the substitutions at the 392nd, 397th, and 435th positions, the substitutions at the 392nd, 300th, and 435th positions, the substitutions at the 397th, 300th, and 435th positions, or the substitutions at the 392nd, 397th, 300th, and 435th positions. The substitution of H for R at the 435th position is intended to permit for the purification of the human IgG3 antibody with Protein A (Ito S et al., Exp Clin Immunogenet. 1990, 7 (2): 91-100).

Moreover, the stabilized human IgG3 antibody of the present invention has at least a substitution of the CH3 domain of an IgG1 heavy chain for the CH3 domain of the heavy chain constant region thereof. For example, the CH3 domain is substituted by the CH3 domain of an IgG1 heavy chain, or the CH2 and CH3 domains are substituted by the CH2 and CH3 domains of an IgG1 heavy chain.

In addition to the substitutions described above, a variation for reducing or enhancing CDC activity and/or ADCC activity can further be introduced into the constant region of the IgG3 heavy chain.

The present invention also provides methods for producing antibodies comprising the substitutions, methods for suppressing the aggregation of antibodies comprising the substitutions, or compositions comprising the antibodies.

Specifically, the present invention is as follows:

[1] An IgG heavy chain comprising the constant region of a human IgG2 heavy chain having at least a substitution of Y for F at the 300th position designated by the EU index of Kabat et al.

[2] An IgG heavy chain comprising the constant region of a human IgG2 heavy chain having at least a substitution of L for V at the 309th position designated by the EU index of Kabat et al.

[3] An IgG heavy chain comprising the constant region of a human IgG2 heavy chain having at least a substitution of A for T at the 339th position designated by the EU index of Kabat et al.

[4] The IgG heavy chain according to any of [1] to [3], wherein the constant region of the heavy chain further comprises an amino acid substitution of S for P at the 331st position designated by the EU index of Kabat et al.

[5] A monoclonal antibody comprising an IgG heavy chain according to any of [1] to [4].

[6] The IgG heavy chain according to any of [1] to [4], wherein the IgG heavy chain has the heavy chain variable region of a monoclonal antibody produced by a hybridoma KM341-1-19 (Accession No. FERM BP-7759).

[7] A monoclonal antibody consisting of: an IgG heavy chain according to [6]; and a light chain having the light chain variable region of a monoclonal antibody produced by a hybridoma KM341-1-19 (Accession No. FERM BP-7759).

[8] The IgG heavy chain according to any of [1] to [4], wherein the IgG heavy chain has the variable region of an IgG heavy chain represented by SEQ ID NO: 2.

[9] A monoclonal antibody consisting of: an IgG heavy chain according to [8]; and a light chain having the variable region of an IgG light chain represented by SEQ ID NO: 4.

[10] The IgG heavy chain according to [4], wherein the IgG heavy chain consists of the portion of a polypeptide represented by SEQ ID NO: 31 except for a signal sequence.

[11] A monoclonal antibody consisting of: an IgG heavy chain according to [10]; and the light chain of a monoclonal antibody consisting of the portion of a polypeptide represented by SEQ ID NO: 33 except for a signal sequence.

[12] A polynucleotide represented by SEQ ID NO: 30.

[13] An expression vector having a polynucleotide according to [12].

[14] A host comprising an expression vector according to [13].

[15] The IgG heavy chain according to [4], wherein the IgG heavy chain is produced by a host according to [14].

[16] A monoclonal antibody consisting of: an IgG heavy chain according to [15]; and the light chain of a monoclonal antibody produced by a host comprising an expression vector having a polynucleotide represented by SEQ ID NO: 32.

[17] A method for producing an IgG heavy chain, comprising the step of substituting Y for F at the 300th position designated by the EU index of Kabat et al. in the constant region of a human IgG2 heavy chain.

[18] A method for producing an IgG heavy chain, comprising the step of substituting L for V at the 309th position designated by the EU index of Kabat et al. in the constant region of a human IgG2 heavy chain.

[19] A method for producing an IgG heavy chain, comprising the step of substituting A for T at the 339th position designated by the EU index of Kabat et al. in the constant region of a human IgG2 heavy chain.

[20] A production method, comprising a method for producing a monoclonal antibody according to any of [17] to [19].

[21] A method for producing an IgG heavy chain, comprising the step of: culturing, in a culture solution, a host comprising an expression vector having a polynucleotide represented by SEQ ID NO: 30; and obtaining a monoclonal antibody heavy chain from the resulting cultures and/or the host.

[22] A method for producing a monoclonal antibody, comprising the step of: culturing, in a culture solution, a host comprising an expression vector having polynucleotides represented by SEQ ID NOS: 30 and 32; and obtaining a monoclonal antibody from the resulting cultures and/or the host.

[23] A method for producing an IgG heavy chain, comprising the step of: culturing, in a culture solution, a host comprising an expression vector having a polynucleotide represented by SEQ ID NO: 34; and obtaining an IgG heavy chain from the resulting cultures and/or the host.

[24] A method for producing a monoclonal antibody, comprising the step of: culturing, in a culture solution, a host comprising an expression vector having polynucleotides represented by SEQ ID NOS: 34 and 36; and obtaining a monoclonal antibody from the resulting cultures and/or the host.

[25] A method for producing a monoclonal antibody, comprising the step of: culturing, in a culture solution, a host comprising an expression vector having polynucleotides encoding the heavy and light chains of a monoclonal antibody according to [5]; and obtaining a monoclonal antibody from the resulting cultures and/or the host.

[26] A method for suppressing monoclonal antibody aggregation, characterized by comprising substituting Y for F at the 300th position designated by the EU index of Kabat et al. in the constant region of a human IgG2 heavy chain.

[27] A method for suppressing monoclonal antibody aggregation, characterized by comprising substituting L for V at the 309th position designated by the EU index of Kabat et al. in the constant region of a human IgG2 heavy chain.

[28] A method for suppressing monoclonal antibody aggregation, characterized by comprising substituting A for T at the 339th position designated by the EU index of Kabat et al. in the constant region of a human IgG2 heavy chain.

[29] A pharmaceutical composition comprising a monoclonal antibody according to any of [7], [9], [11], and [16] as an active ingredient.

[30] The pharmaceutical composition according to [29], wherein the pharmaceutical composition is used in the prevention or treatment of tumor, a pathogen, or autoimmune disease.

[31] A composition comprising a monoclonal antibody according to any of [7], [9], [11], and [16].

[32] An IgG heavy chain comprising the constant region of a human IgG3 heavy chain having at least a substitution of V for M at the 397th position designated by the EU index of Kabat et al.

[33] A monoclonal antibody comprising an IgG heavy chain according to [32].

[34] A method for producing an IgG heavy chain, comprising the step of substituting K for N at the 392nd position designated by the EU index of Kabat et al. in the constant region of a human IgG3 heavy chain.

[35] A method for producing an IgG heavy chain, comprising the step of substituting V for M at the 397th position designated by the EU index of Kabat et al. in the constant region of a human IgG3 heavy chain.

[36] A production method, comprising a method for producing a monoclonal antibody according to [34] or [35].

[37] A method for producing a monoclonal antibody, comprising the step of: culturing, in a culture solution, a host comprising an expression vector having polynucleotides encoding the heavy and light chains of a monoclonal antibody according to [33]; and obtaining a monoclonal antibody from the resulting cultures and/or the host.

[38] A method for suppressing monoclonal antibody aggregation, characterized by comprising substituting K for N at the 392nd position designated by the EU index of Kabat et al. in the constant region of a human IgG3 heavy chain.

[39] A method for suppressing monoclonal antibody aggregation, characterized by comprising substituting V for M at the 397th position designated by the EU index of Kabat et al. in the constant region of a human IgG3 heavy chain.

[40] A composition comprising a monoclonal antibody according to any of [33], [36], and [37].

The present invention further comprises the following aspects:

[41] The IgG heavy chain according to any of [1] to [4], wherein the IgG heavy chain has the heavy chain variable region of a monoclonal antibody produced by a hybridoma 2105 (Accession No. BP-8024).

[42] A monoclonal antibody consisting of: an IgG heavy chain according to [41]; and a light chain having the light chain variable region of a monoclonal antibody produced by a hybridoma 2105 (Accession No. BP-8024).

[43] The IgG heavy chain according to any of [1] to [4], wherein the IgG heavy chain has the variable region of an IgG heavy chain represented by SEQ ID NO: 6.

[44] A monoclonal antibody consisting of: an IgG heavy chain according to [43]; and a light chain having the variable region of an IgG light chain represented by SEQ ID NO: 8.

[45] The IgG heavy chain according to [4], wherein the IgG heavy chain consists of the portion of a polypeptide represented by SEQ ID NO: 35 except for a signal sequence.

[46] A monoclonal antibody consisting of: an IgG heavy chain according to [45]; and the light chain of a monoclonal antibody consisting of the portion of a polypeptide represented by SEQ ID NO: 37 except for a signal sequence.

[47] A polynucleotide represented by SEQ ID NO: 34.

[48] An expression vector having a polynucleotide according to [47].

[49] A host comprising an expression vector according to [48].

[50] The IgG heavy chain according to [4], wherein the IgG heavy chain is produced by a host according to [49].

[51] A monoclonal antibody consisting of: an IgG heavy chain according to [50]; and the light chain of a monoclonal antibody produced by a host comprising an expression vector having a polynucleotide represented by SEQ ID NO: 36.

[52] A pharmaceutical composition comprising a monoclonal antibody according to any of [42], [44], [46], and [51] as an active ingredient.

[53] The pharmaceutical composition according to [52], wherein the pharmaceutical composition is used in the prevention or treatment of tumor, a pathogen, or autoimmune disease.

[54] A composition comprising a monoclonal antibody according to any of [42], [44], [46], and [51].

The antibody of the present invention improved in stability by a substitution of Y for F at the 300th position, L for V at the 309th position, or A for T at the 339th position in the amino acid sequence of the IgG2 heavy chain possesses the characteristics of exhibiting reduced aggregate formation, particularly, reduced aggregate formation at low pH, while maintaining antigen-binding properties. Thus, the antibody of the present invention can be produced stably as a drug. Furthermore, the antibody of the present invention when administered to a test subject easily avoids side-effects caused by contamination with antibody aggregates and can be used with safety.

The antibody of the present invention improved in stability by a substitution of K for N at the 392nd position, V for M at the 397th position, or Y for F at the 300th position in the amino acid sequence of the IgG3 heavy chain possesses the characteristics of exhibiting reduced aggregate formation, particularly, reduced aggregate formation at low pH, while maintaining antigen-binding properties. Thus, the antibody of the present invention can be produced stably as a drug. Furthermore, the antibody of the present invention when administered to a test subject easily avoids side-effects caused by contamination with antibody aggregates and can be used with safety.

Furthermore, an antibody having reduced ADCC and/or CDC in addition to improved stability can be obtained by, for example, a substitution of serine for proline at the 331st position. This antibody when administered to a test subject can avoid side-effects caused by ADCC and/or CDC and can be used as a drug with safety.

The present specification encompasses contents described in the specification and/or drawings of JP Patent Publication (Kokai) No. 2005-005794A that serves as a basis of the priority of the present application.

BEST MODE FOR CARRYING OUT THE INVENTION

Figure 1A:
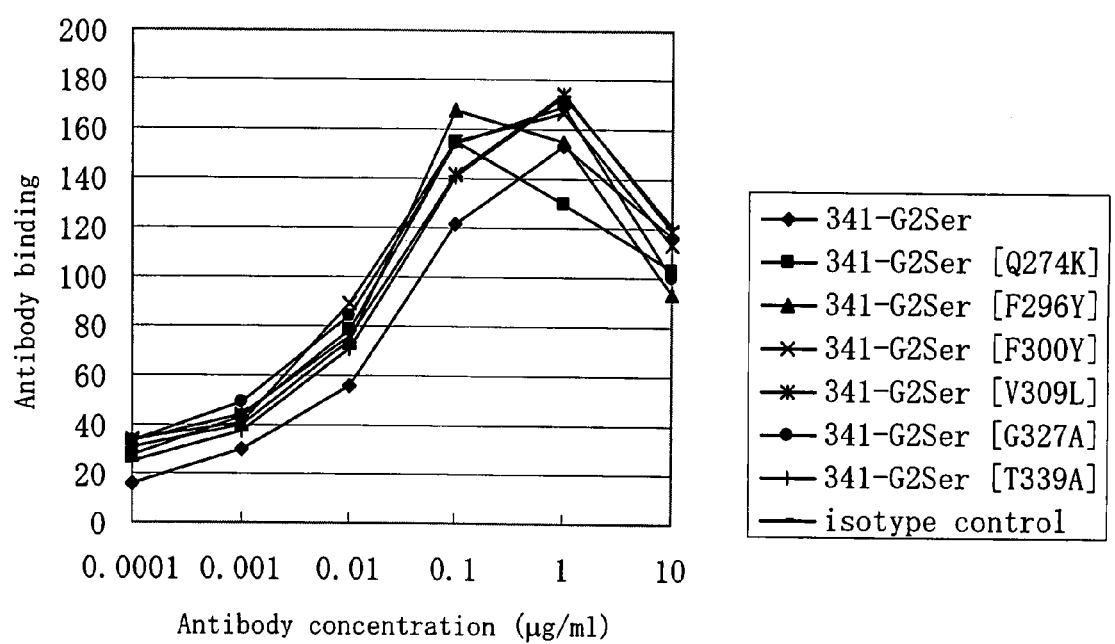
FIG. 1A is a diagram showing the binding activity of variants of an anti-CD40 antibody KM341-1-19 to Ramos cells (Ramos cell binding activity)

1. Improvement in Stability and Physical Property of IgG2 and IgG3 Antibodies

An IgG heavy chain comprises two regions: a variable region that determines binding specificity to antigens; and a constant region that participates in the effector function expression of the antibody. The variable region structurally differs in antigen-binding site sequence depending on the recombination of a gene constituting the variable region and the introduction of a somatic mutation. This brings about the characteristic of being capable of recognizing a very large number of foreign antigens.

Moreover, antibodies are originally molecules responsible for biophylaxis functions against foreign microorganisms, viruses, or cancers and therefore also have the effect of killing and removing cells bound with the antibodies. This is called effector functions. These killing functions are divided into two types, one of which is called Antibody-Dependent Cellular Cytotoxicity (hereinafter, abbreviated to ADCC), and the other of which is called Complement-Dependent Cytotoxicity (hereinafter, abbreviated to CDC). ADCC refers to cytotoxicity that is induced by cellular activation caused by the binding of Macrophage, NK cells, neutrophil, or the like via FcR expressed on the surface thereof to the antibody constant region. On the other hand, CDC refers to cytotoxicity that is caused by the complement system activated by antibody binding to an antigen. These activities are known to differ in intensity depending on antibody subclasses (Charles A. Janeway et al. Immunobiology, 1997, Current Biology Ltd./Garland Publishing Inc.).

The present invention can improve the stability of IgG2 and IgG3 antibodies while maintaining their specific antigen-binding properties. Specifically, a substitution of Y for F at the 300th position, L for V at the 309th position, or A for T at the 339th position in the amino acid sequence of the IgG2 heavy chain can improve antibody stability. The antibody of the present invention may have these substitutions alone or in combination. Moreover, a substitution of the CH2 domain of an IgG1 heavy chain for the CH2 domain of the IgG2 heavy chain or the CH2 and CH3 domains of an IgG1 heavy chain for the CH2 and CH3 domains of the IgG2 heavy chain can improve antibody stability. Alternatively, a substitution of K for N at the 392nd position, V for M at the 397th position, or Y for F at the 300th position in the amino acid sequence of the IgG3 heavy chain according to the present invention can improve antibody stability. The antibody of the present invention may have these substitutions alone or in combination. Moreover, a substitution of the CH3 domain of an IgG1 heavy chain for the CH3 domain of the IgG3 heavy chain or the CH2 and CH3 domains of an IgG1 heavy chain for the CH2 and CH3 domains of the IgG3 heavy chain can improve antibody stability.

In the present invention, a variant antibody comprising the domain of a certain subclass substituted by the domain of another subclass is also referred to as a domain swap variant antibody.

In the present invention, an antibody improved in stability refers to an antibody that has no reduction in antigen-binding ability even under acidic conditions, that is, under low pH conditions, for example, at pH 4 or lower, and hardly forms aggregates under these conditions. Alternatively, the antibody improved in stability refers to an antibody that exhibits a low aggregate content when purified by use of a Protein A or Protein G affinity column. The antibody improved in stability refers to an antibody that forms an aggregate at a content of 10% or lower, preferably 5% or lower, more preferably 1% or lower, for example, when treated at pH 3.5 for 10 minutes or 60 minutes. The aggregate content can be measured, for example, by liquid chromatography.

In the present invention, an antibody improved in physical property refers to an antibody that has ADCC and/or CDC adjusted to desired intensity, in addition to stability, or an antibody that has FcR-binding ability adjusted to a desired level. The adjustment of ADCC and/or CDC and the adjustment of FcR-binding ability can be performed by introducing a variation into the antibody.

An additional appropriate variation can be introduced into the antibody improved in stability to thereby reduce or enhance ADCC and/or CDC.

For example, L235, D265, D270, K322, P331, and P329 (the alphabet denotes the single character code of the amino acid; the number denotes the EU index of Kabat et al. (Kabat et al., Sequences of proteins of Immunological Interest, 1991 Fifth edition); hereinafter, interpreted in the same manner) have been considered to play an important role in the complement-activating capacity of human IgG. These sites can be substituted by other amino acids to thereby reduce CDC activity (Esohe E. Idusogie et al. J. Immunol. 2000, 164: 4178-4184; Yuanyuan Xu et al. J. Biol. Chem. 1994, 269: 3469-3474; Brekke, O. H. et al. Eur. J. Immunol. 1994, 24: 2542; Morgan, A., et al., Immunology 1995, 86: 319; Lund, J., et al., J. Immunol., 1996, 157: 4963; and Tao, M. H., et al., J. Exp. Med. 1993, 178: 661). Specifically, the reduction in CDC activity can be performed by a substitution of A for D270, K322, P329, or P331. Alternatively, the reduction in CDC activity can be performed by a substitution of S or G for P331.

Moreover, Glu233-Ser239, Gly316-Lys338, Lys274-Arg301, Tyr407-Arg416, Asn297, Glu318, Leu234-Ser239, Asp265-Glu269, Asn297-Thr299, and Ala327-Ile332 have been considered to participate in the binding of IgG with FcR (Duncan, A. R., Woof, J. M., Partridge, L. J., Burton, D. R., and Winter, G. (1988) Nature 332, 563-564; Gessner, J. E., Heiken, H., Tamm, A., and Schmidt, R. E. (1998) Ann. Hematol. 76, 231-248; Gavin, A., Hulett, M., and Hogarth, P. M. (1998) in The Immunoglobulin Receptors and Their Physiological and Pathological Roles in Immunity (van de Winkel, J. G. J., and Hogarth, P. M., eds), pp. 11-35, Kluwer Academic Publishers Group, Dordrecht, The Netherlands, Sautes, C. (1997) in Cell-mediated Effects of Immunoglobulins (Fridman, W. H., and Sautes, C., eds), pp. 29-66, R. G. Landes Co., Austin, Tex., Da'ron, M. (1997) Annu. Rev. Immunol. 15, 203-234; Canfield, S. M., and Morrison, S. L. (1991) J. Exp. Med. 173, 1483-1491; Chappel, M. S., Isenman, D. E., Everett, M., Xu, Y.-Y., Dorrington, K. J., and Klein, M. H. (1991) Proc. Natl. Acad. Sci. U.S.A. 88, 9036-9040; Woof, J. M., Partridge, L. J., Jefferis, R., and Burton, D. R. (1986) Mol. Immunol. 23, 319-330; and Wines, B. D., Powell, M. S., Parren, P. W. H. I., Barnes, N., and Hogarth, P. M. (2000) J. Immunol. 164, 5313-5318). A variation can be introduced into these regions to thereby reduce ADCC activity. Specifically, reduction in FcR-binding ability can be performed by a substitution of E for L235 or A for G237.

A variation can be introduced in a manner the reverse of the variations described above to thereby enhance the ADCC and/or CDC of the antibody improved in stability. The antibody of the present invention also encompasses an antibody enhanced in ADCC and/or CDC.

The antibody of the present invention has one or more, preferably 1 to 20, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, or 1 or 2 amino acid variations for enhancing or reducing the ADCC and/or CDC activity.

Examples of an antibody improved in stability that has the substitution of Y for F at the 300th position, L for V at the 309th position, or A for T at the 339th position in the heavy chain of an IgG2 antibody, or an antibody improved in stability that has these substitutions in combination include, but not limited to, anti-CD40 antibodies. More specifically, the antibody is exemplified by an antibody having the light and heavy chain variable regions of an antibody produced by a hybridoma KM341-1-19 (Accession No. BP-7759) or an antibody having the light and heavy chain variable regions of an antibody produced by a hybridoma 2105 (Accession No. BP-8024). Examples of an antibody improved in stability that has the substitution of K for N at the 392nd position, V for M at the 397th position, or Y for F at the 300th position in the heavy chain of an IgG3 antibody, or an antibody improved in stability that has these substitutions in combination include, but not limited to, anti-CD40 antibodies.

2. Definition

Terms used herein are defined as follows:

"CD40" means a polypeptide having the amino acid sequence shown by Clark et al. (E. A. Clark et al., Proc. Natl. Acad. Sci. USA 83: 4494, 1986) or Stamenkovic et al. (I. Stamenkovic et al., EMBO J. 8: 1403, 1989) and is particularly an antigenic polypeptide expressed in the surface of B cells, DC, macrophage, endothelial cells, epithelial cells, or tumor cells thereof.

An "anti-CD40 antibody" means monoclonal and polyclonal antibodies against cellularly expressed CD40, full-length CD40, or partial-length CD40. The anti-CD40 antibody is preferably a monoclonal antibody.

The "agonist" effect of the anti-CD40 antibody means the effect of promoting the binding of CD40 expressed in the surface of cells such as B cells, tumor cells, or dendritic cells with its ligands or the effect of imparting one or more of influences of CD40 ligands on CD40-expressing cells to cells that express CD40. An "agonistic antibody" means an antibody that has such effects. One example of the influences on CD40-expressing cells includes the promotion of B cell growth or the promotion of antibody production.

The "antagonistic" effect of the anti-CD40 antibody means the effect of inhibiting the binding of CD40 expressed in the surface of cells such as B cells, tumor cells, or dendritic cells with its ligands or the effect of neutralizing one or more of influences of CD40 ligands on CD40-expressing cells. An "antagonistic antibody" means an antibody that has such effects. One example of the influences on CD40-expressing cells includes the suppression of B cell growth or the suppression of antibody production.

An "antibody" is derived from genes encoding heavy chain variable and constant regions and light chain variable and constant regions constituting immunoglobulin (collectively called antibody genes). The antibody of the present invention also encompasses antibodies of any immunoglobulin class and antibodies having any isotype. Examples of proteins (antigens) to which the antibody of the present invention binds include, but not limited to, CD40.

A "CH1 domain", "hinge domain", "CH2 domain", and "CH3 domain" denote a portion of the heavy chain constant region of the antibody and are based on the EU index of Kabat et al. (Kabat et al., Sequences of proteins of immunological interest, 1991 Fifth edition). The CH1 domain is the portion comprising the sequence at the 118th to 215th positions according to the EU index, the hinge domain is the portion comprising the sequence at the 216th to 237th positions according to the EU index, the CH2 domain is the portion comprising the sequence at the 238th to 340th positions according to the EU index, and the CH3 domain is the portion consisting of the sequence at the 341st to 446th positions according to the EU index.

A "human antibody" means antibody that is an expression product of antibody genes derived from humans. Examples of previously known human IgG2 include J00230 (SEQ ID NO: 64), AJ250170 (SEQ ID NO: 65), AF449616 (SEQ ID NO: 66), AF449617 (SEQ ID NO: 67), AF449618 (SEQ ID NO: 68), Z49802 (SEQ ID NO: 69), and Z49801 (SEQ ID NO: 70). Examples of previously known human IgG3 include M12958, K01313 (SEQ ID NO: 71), X16110 (SEQ ID NO: 72), X99549 (SEQ ID NO: 73), AJ390236 (SEQ ID NO: 74), AJ390237 (SEQ ID NO: 75), AJ390238 (SEQ ID NO: 76), AJ390241 (SEQ ID NO: 77), AJ390242 (SEQ ID NO: 78), AJ390246 (SEQ ID NO: 79), AJ390247 (SEQ ID NO: 80), AJ390252 (SEQ ID NO: 81), AJ390244 (SEQ ID NO: 82), AJ390254 (SEQ ID NO: 83), AJ390260 (SEQ ID NO: 84), AJ390262 (SEQ ID NO: 85), AJ390272 (SEQ ID NO: 86), AJ390276 (SEQ ID NO: 87), and AJ390279 (SEQ ID NO: 88) (these symbols are Gene Bank Accession Numbers of the genes). The sequences represented by SEQ ID NOS: 64 to 88 denote their respective nucleotide sequences.

A "human IgG heavy chain" is a heavy chain consisting of a heavy chain variable region and a human IgG heavy chain constant region. For example, a "human IgG2 heavy chain" is a heavy chain consisting of a heavy chain variable region and a human IgG2 heavy chain constant region.

A "human IgG antibody" is an antibody consisting of a human IgG heavy chain and a human light chain. For example, a "human IgG2 antibody" is an antibody consisting of a human IgG2 heavy chain and a human light chain.

The antibody of the present invention can be prepared appropriately, for example, by use of an antibody gene isolation method from hybridomas well known by those skilled in the art, the sequence information of the human antibody constant regions of the above-described human antibody genes known in the art, or site-specific mutagenesis into genes.

The antibody of the present invention can be obtained by incorporating the antibody gene into an expression vector; introducing the vector into an appropriate host cell; and collecting and purifying an antibody from the resulting cell or the culture supernatant of the cell.

The vector used is a phage or plasmid capable of autonomously amplifying in a host cell or capable of being incorporated into the chromosome of a host cell. Examples of the plasmid DNA include plasmids derived from *E. coli, Bacillus subtilis*, or yeast. Examples of the phage DNA include λ phages.

The host used in transformation is not particularly limited as long as it can express the gene of interest. Examples thereof include bacteria (e.g., *E. coli* and *Bacillus subtilis*), yeast, animal cells (e.g., COS cells and CHO cells), and insect cells.

A gene delivery method into a host is known in the art. Examples thereof include any method (e.g., a method using calcium ions, electroporation, spheroplast, lithium acetate, calcium phosphate, and lipofection methods). Examples of a gene delivery method into an animal described below include microinjection, a gene transfer method into ES cells using electroporation or lipofection, and a nuclear transplantation method.

In the present invention, "cultures" mean any of (a) culture supernatants, (b) cultured cells or cultured strains or homogenates thereof, and (c) secreted products from transformants. To culture transformants, a medium suitable to a host used is used, and a static culture method, a culture method with roller bottles, or the like is adopted.

When the protein of interest is produced within strains or cells after culture, the antibody is collected by homogenizing the strains or cells. Alternatively, when the antibody of interest is produced outside strains or cells, the culture solution is directly used or, for example, centrifuged to remove the strains or cells. Then, general biochemical methods using a variety of chromatography techniques used in protein isolation and purification can be used alone or in appropriate combination to thereby isolate and purify the antibody of interest from the cultures.

Furthermore, an animal host comprising the gene of the antibody of interest incorporated in the endogenous gene, for example, a transgenic cow, transgenic goat, transgenic sheep, or transgenic pig is prepared by use of a transgenic animal production technique, and monoclonal antibodies derived form the antibody gene can be obtained in large amounts from milk secreted from the transgenic animal (Wright, G., et al. (1991) Bio/Technology 9, 830-834). In in-vitro hybridoma culture, a hybridoma is amplified, maintained, and stored to meet a variety of conditions such as the property of a cell species to be cultured, the purposes of experiments or research, and culture methods. This in-vitro hybridoma culture can be performed by use of a known nutritional medium used for monoclonal antibody production in a culture supernatant or every nutritional medium induced and prepared from a known basal medium.

3. Pharmaceutical Composition

The scope of the present invention also encompasses a pharmaceutical composition comprising a purified preparation of the antibody of the present invention. Preferably, such a pharmaceutical composition comprises physiologically acceptable diluents or carriers, in addition to the antibody and may be a mixture with other antibodies or other drugs such as antibiotics. Examples of an appropriate carrier include, but not limited to, saline, phosphate-buffered saline, glucose-supplemented phosphate-buffered saline, and buffered saline. Alternatively, the antibody may be lyophilized (freeze-dried) and reconstituted for use, when needed, by the addition of such a buffered aqueous solution. Administration routes are oral routes and non-enteral routs including intravenous, intramuscular, subcutaneous, and intraperitoneal injection or drug administration.

In this case, an effective dose combining an effective amount of the antibody of the present invention and an appropriate diluent and a pharmaceutically available carrier is 0.0001 mg to 100 mg per kg of body weight per dosage, which is administered at 2-day to 8-week intervals.

The pharmaceutical composition comprising an agonistic anti-CD40 antibody as the antibody of the present invention is used as an adjuvant (antivirus or anti-infectious disease agent). In this context, a pathogen is exemplified by type A, B, C, D, or E hepatitis virus, HIV, influenza virus, herpes simplex virus, cytomegalovirus, EB virus, papilloma virus, chlamydia, mycoplasma, *toxoplasma*, malaria, trypanosome, and tuberculosis. Alternatively, the pharmaceutical composition of the present invention is used as an anti-tumor agent. Examples of tumor to be treated by the pharmaceutical composition include malignant tumor containing CD40-expressing cancer cells, for example, lymphoma (e.g., Hodgkin lymphoma), leukemia, malignant melanoma, pancreas cancer, lung cancer, ovarian cancer, bladder cancer, breast cancer, colon cancer, prostatic cancer, and head and neck cancer. Alternatively, the pharmaceutical composition of the present invention is used as a therapeutic agent for autoimmune disease. Disease to be treated by the pharmaceutical agent is exemplified by rheumatism. These diseases may occur concurrently. Alternatively, the pharmaceutical composition of the present invention can also be used as an adjuvant in combination with vaccines such as cancer-specific peptides.

4. Composition

The scope of the present invention also encompasses a composition comprising the antibody of the present invention. The composition comprises other ingredients, for example, buffers (intended for moderating pH changes; examples thereof include sodium glutamate), stabilizers (intended for enhancing the chemical or physical stability of the antibody; examples thereof include glycine), surfactants (examples thereof include polysorbate), or preservatives, in addition to the antibody. The composition is, for example, in an aqueous solution or freeze-dried form. The composition can be used, for example, as a reagent in antigen analysis. Aggregate formation is suppressed in the antibody of the present invention having an amino acid or domain substitution as compared with in antibodies free from the substitution. Therefore, the composition can be produced efficiently from the viewpoint of yields and so on. Moreover, the antibody of the present invention hardly causes aggregation in an analytical solution in antigen analysis and can therefore produce a high-precision result.

EXAMPLES

The present invention will be described specifically with reference to Examples below. However, the present invention is not intended to be limited to these Examples.

Example 1

Preparation of Anti-CD40 Antibodies Comprising Fused IgG1/IgG2 Constant Region

Of anti-CD40 antibodies described in WO 02/088186, an antibody having the light and heavy chain variable regions of an antibody (hereinafter, a 341-1-19 antibody) produced by a hybridoma KM341-1-19 (Accession No. BP-7759) and an antibody having the light and heavy chain variable regions of an antibody (hereinafter, a 2105 antibody) produced by a hybridoma 2105 (Accession No. BP-8024) were prepared. The antibodies produced by the hybridomas KM341-1-19 (Accession No. BP-7759) and 2105 (Accession No. BP-8024) have been shown to be agonistic antibodies.

The 341-1-19 antibody is an antibody that is produced by the hybridoma KM341-1-19, which has been deposited as Accession No. FERM BP-7759 on Sep. 27, 2001 with International Patent Organism Depositary, National Institute of Advanced Industrial Science and Technology (Central 6, 1-1-1, Higashi, Tsukuba, Ibaraki, Japan). The 2105 antibody is an antibody that is produced by the hybridoma 2105, which has been deposited as Accession No. FERM BP-8024 on Apr. 17, 2002 with International Patent Organism Depositary, National Institute of Advanced Industrial Science and Technology (Central 6, 1-1-1, Higashi, Tsukuba, Ibaraki, Japan).

Nucleotide sequences encoding the heavy and light chain variable regions of the 341-1-19 antibody and amino acid sequences of the heavy and light chains are respectively shown below.

A signal sequence in the nucleotide sequence (SEQ ID NO: 1) of the heavy chain of the 341-1-19 antibody starts at adenine (A) at the 50th position. The boundary between the signal sequence and the variable region is positioned between [adenine] ([A]) at the 109th position and cytosine (C) at the 110th position, while the boundary between the variable region and the constant region is positioned between adenine (A) at the 493rd position and guanine (G) at the 494th position (examined with gene sequence prediction software Signal P ver. 2).

The boundary between the signal sequence and the variable region in the amino acid sequence (SEQ ID NO: 2) of the heavy chain of the 341-1-19 antibody is positioned between serine (S) at the 20th position and glutamine (Q) at the 21st position, while the boundary between the variable region and the constant region is positioned between serine (S) at the 148th position and alanine (A) at the 149th position.

Thus, the nucleotide sequence of the heavy chain variable region of the 341-1-19 antibody reaches from cytosine (C) at the 110th position to adenine (A) at the 493rd position in SEQ ID NO: 1. The amino acid sequence of the heavy chain variable region of the 341-1-19 antibody reaches from glutamine (Q) at the 21st position to serine (S) at the 148th position in SEQ ID NO: 2.

A signal sequence in the nucleotide sequence (SEQ ID NO: 3) of the light chain of the 341-1-19 antibody starts at adenine (A) at the 29th position. The boundary between the signal sequence and the variable region is positioned between [adenine] ([A]) at the 88th position and guanine (G) at the 89th position, while the boundary between the variable region and the constant region is positioned between adenine (A) at the 400th position and [cytosine] ([C]) at the 401st position (examined with gene sequence prediction software Signal P ver. 2).

The boundary between the signal sequence and the variable region in the amino acid sequence (SEQ ID NO: 4) of the light chain of the 341-1-19 antibody is positioned between glycine (G) at the 20th position and glutamic acid (E) at the 21st position, while the boundary between the variable region and the constant region is positioned between lysine (K) at the 124th position and [arginine] ([R]) at the 125th position.

Thus, the nucleotide sequence of the light chain variable region of the 341-1-19 antibody reaches from guanine (G) at the 89th position to adenine (A) at the 400th position in SEQ ID NO: 3. The amino acid sequence of the light chain variable region of the 341-1-19 antibody reaches from glutamic acid (E) at the 21st position to lysine (K) at the 124th position in SEQ ID NO: 4.

```
341-1-19 heavy chain nucleotide sequence
                                        (SEQ ID NO: 1)
GTCGACGCTGAATTCTGGCTGACCAGGGCAGCCACCAGAGCTCCAGACAA

TGTCTGTCTCCTTCCTCATCTTCCTGCCCGTGCTGGGCCTCCCATGGGGT

GTCCTGTCACAGGTCCAACTGCAGCAGTCAGGTCCAGGACTGGTGAAGCC

CTCGCAGACCCTCTCACTCACCTGTGCCATCTCCGGGGACAGTGTCTCTA
```

-continued
```
GCAACAGTGCTACTTGGAACTGGATCAGGCAGTCCCCATCGAGAGACCTT

GAGTGGCTGGGAAGGACATACTACAGGTCCAAGTGGTATCGTGATTATGT

AGGATCTGTGAAAAGTCGAATAATCATCAACCCAGACACATCCAACAACC

AGTTCTCCCTGCAGCTGAACTCTGTGACTCCCGAGGACACGGCTATATAT

TACTGTACAAGAGCACAGTGGCTGGGAGGGGATTACCCCTACTACTACAG

TATGGACGTCTGGGGCCAAGGGACCACGGTCACCGTCTCTTCAGCCTCCA

CCAAGGGCCCATCGGTCTTCCCCCTGGCGCCCTGCTCCAGGAGCACCTCC

GAGAGCACAGCGGCCCTGGGCTGCCTGGTCAAGGACTACTTCCCCGAACC

GGTGACGGTGTCGTGGAACTCAGGCGCTCTGACCAGCGGCGTGCACACCT

TCCCAGCTGTCCTACAGTCCTCAGGACTCTACTCCCTCAGCAGCGTGGTG

ACCGTGCCCTCCAGCAACTTCGGCACCCAGACCTACACCTGCAACGTAGA

TCACAAGCCCAGCAACACCAAGGTGGACAAGACAGTTGAGCGCAAATGTT

GTGTCGAGTGCCCACCGTGCCCAGCACCACCTGTGGCAGGACCGTCAGTC

TTCCTCTTCCCCCCAAAACCCAAGGACACCCTCATGATCTCCCGGACCCC

TGAGGTCACGTGCGTGGTGGTGGACGTGAGCCACGAAGACCCCGAGGTCC

AGTTCAACTGGTACGTGGACGGCGTGGAGGTGCATAATGCCAAGACAAAG

CCACGGGAGGAGCAGTTCAACAGCACGTTCCGTGTGGTCAGCGTCCTCAC

CGTTGTGCACCAGGACTGGCTGAACGGCAAGGAGTACAAGTGCAAGGTCT

CCAACAAAGGCCTCCCAGCCCCCATCGAGAAAACCATCTCCAAAACCAAA

GGGCAGCCCCGAGAACCACAGGTGTACACCCTGCCCCCATCCCGGGAGGA

GATGACCAAGAACCAGGTCAGCCTGACCTGCCTGGTCAAAGGCTTCTACC

CCAGCGACATCGCCGTGGAGTGGGAGAGCAATGGGCAGCCGGAGAACAAC

TACAAGACCACACCTCCCATGCTGGACTCAGACGGCTCCTTCTTCCTCTA

CAGCAAGCTCACCGTGGACAAGAGCAGGTGGCAGCAGGGGAACGTCTTCT

CATGCTCCGTGATGCATGAGGCTCTGCACAACCACTACACGCAGAAGAGC

CTCTCCCTGTCTCCGGGTAAATGAGGATCC 341-1-19 heavy chain amino acid sequence
                                        (SEQ ID NO: 2)
MSVSFLIFLPVLGLPWGVLSQVQLQQSGPGLVKPSQTLSLTCAISGDSVS

SNSATWNWIRQSPSRDLEWLGRTYYRSKWYRDYVGSVKSRIIINPDTSNN

QFSLQLNSVTPEDTAIYYCTRAQWLGGDYPYYYSMDVWGQGTTVTVSSAS

TKGPSVFPLAPCSRSTSESTALALGCLVKDYFPEPVTVSWNSGALTSGVH

TFPAVLQSSGLYSLSSVVTVPSSNFGTQTYTCNVDHKPSNTKVDKTVERK

CCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKGF

YPSDIAVEWESNGQPENNYKTTPPMLDSDGSFFLYSKLTVDKSRWQQGNV

FSCSVMHEALHNHYTQKSLSLSPGK 341-1-19 light chain nucleotide sequence
                                        (SEQ ID NO: 3)
ACTGCTCAGTTAGGACCCAGAGGGAACCATGGAAGCCCCAGCTCAGCTTC

TCTTCCTCCTGCTACTCTGGCTCCCAGATACCACCGGAGAAATTGTGTTG

ACACAGTCTCCAGCCACCCTGTCTTTGTCTCCAGGGGAAAGAGCCACCCT
```

-continued
CTCCTGCAGGGCCAGTCAGAGTGTTAGCAGCTACTTAGCCTGGTACCAAC

AGAAACCTGGCCAGGCTCCCAGGCTCCTCATCTATGATGCATCCAACAGG

GCCACTGGCATCCCAGCCAGGTTCAGTGGCAGTGGGTCTGGGACAGACTT

CACTCTCACCATCAGCAGCCTAGAGCCTGAAGATTTTGCAGTTTATTACT

GTCAGCAGCGTAGCAACACTTTCGGCCCTGGGACCAAAGTGGATATCAAA

CGTACG 341-1-19 light chain amino acid sequence
(SEQ ID NO: 4)
MEAPAQLLFLLLLWLPDTTGEWLTQSPATLSLSPGERATLSCRASQSVSS

YLAWYQQKPGQAPRLLIYDASNRATGIPARFSGSGSGTDFTLTISSLEPE

DFAVYYCQQRSNTFGPGTKVDIKRT

DNAs encoding the heavy and light chain variable regions of the 2105 antibody and amino acid sequences of the heavy and light chains are respectively shown below.

A signal sequence in the nucleotide sequence (SEQ ID NO: 5) of the heavy chain of the 2105 antibody starts at adenine (A) at the 70th position. The boundary between the signal sequence and the variable region is positioned between [thymine] ([T]) at the 126th position and guanine (G) at the 127th position, while the boundary between the variable region and the constant region is positioned between adenine (A) at the 495th position and guanine (G) at the 496th position (examined with gene sequence prediction software Signal P ver. 2).

The boundary between the signal sequence and the variable region in the amino acid sequence (SEQ ID NO: 6) of the heavy chain of the 2105 antibody is positioned between cysteine (C) at the 19th position and glutamic acid (E) at the 20th position, while the boundary between the variable region and the constant region is positioned between serine (S) at the 142nd position and alanine (A) at the 143rd position.

Thus, the nucleotide sequence of the heavy chain variable region of the 2105 antibody reaches from guanine (G) at the 127th position to adenine (A) at the 495th position in SEQ ID NO: 5. The amino acid sequence of the heavy chain variable region of the 2105 antibody reaches from glutamic acid (E) at the 20th position to serine (S) at the 142nd position in SEQ ID NO: 6.

A signal sequence in the nucleotide sequence (SEQ ID NO: 7) of the light chain of the 2105 antibody starts at adenine (A) at the 28th position. The boundary between the signal sequence and the variable region is positioned between [adenine] ([A]) at the 87th position and guanine (G) at the 88th position, while the boundary between the variable region and the constant region is positioned between adenine (A) at the 405th position and [cytosine] ([C]) at the 406th position (examined with gene sequence prediction software Signal P ver. 2).

The boundary between the signal sequence and the variable region in the amino acid sequence (SEQ ID NO: 8) of the light chain of the 2105 antibody is positioned between glycine (G) at the 20th position and glutamic acid (E) at the 21st position, while the boundary between the variable region and the constant region is positioned between lysine (K) at the 126th position and [arginine] ([R]) at the 127th position.

Thus, the nucleotide sequence of the light chain variable region of the 2105 antibody reaches from guanine (G) at the 88th position to adenine (A) at the 405th position in SEQ ID NO: 7. The amino acid sequence of the light chain variable region of the 2105 antibody reaches from glutamic acid (E) at the 21st position to lysine (K) at the 126th position in SEQ ID NO: 8.

2105 heavy chain nucleotide sequence
(SEQ ID NO: 5)
CTGAACACAGACCCGTCGACTCCCAGGTGTTTCCATTCAGTGATCAGCAC

TGAACACAGAGGACTCACCATGGAGTTGGGACTGAGCTGGATTTTCCTTT

TGGCTATTTTAAAAGGTGTCCAGTGTGAAGTGCAGCTGGTGGAGTCTGGG

GGAGGCTTGGTACAGCCTGGCAGGTCCCTGAGACTCTCCTGTGCAGCCTC

TGGATTCACCTTTGATGATTATGCCATGCACTGGGTCCGGCAAGCTCCAG

GGAAGGGCCTGGAGTGGGTCTCAGGTATTAGTTGGAATAGTGGTAGCTTG

GTGCATGCGGACTCTGTGAAGGGCCGATTCACCATCTCCAGAGACAACGC

CAAGAACTCCCTGTATCTGCAAATGAACAGTCTGAGAGCTGAGGACACGG

CCTTGTATTACTGTGCAAGAGATAGGCTATTTCGGGGAGTTAGGTACTAC

GGTATGGACGTCTGGGGCCAAGGGACCACGGTCACCGTCTCCTCAGCTAG

CACCAAGG 2105 heavy chain amino acid sequence
(SEQ ID NO: 6)
MELGLSWIFLLAILKGVQCEVQLVESGGGLVQPGRSLRLSCAASGFTFDD

YAMHWVRQAPGKGLEWVSGISWNSGSLVHADSVKGPRFTISRDNAKNSLY

LQMNSLRAEDTALYYCARDRLFRGVRYYGMDVWGQGTTVTVSSASTK 2105 light chain nucleotide sequence
(SEQ ID NO: 7)
CTGCTCAGTTAGGACCCAGAGGGAACCATGGAAGCCCCAGCTCAGCTTCT

CTTCCTCCTGCTACTCTGGCTCCCAGATACCACCGGAGAAATTGTGTTGA

CACAGTCTCCAGCCACCCTGTCTTTGTCTCCAGGGGAAAGAGCCACCCTC

TCCTGCAGGGCCAGTCAGAGTGTTAGCAGCTACTTAGCCTGGTACCAACA

GAAACCTGGCCAGGCTCCCAGGCTCCTCATCTATGATGCATCCAACAGGG

CCACTGGCATCCCAGCCAGGTTCAGTGGCAGTGGGTCTGGGACAGACTTC

ACTCTCACCATCAGCAGCCTAGAGCCTGAAGATTTTGCAGTTTATTACTG

TCAGCAGCGTAGCCACTGGCTCACTTTCGGCGGGGGGACCAAGGTGGAGA

TCAAACGTACGGTG 2105 light chain amino acid sequence
(SEQ ID NO: 8)
MEAPAQLLFLLLLWLPDTTGEIVLTQSPATLSLSPGERATLSCRASQSVS

SYLAWYQQKPGQAPRLLIYDASNRATGIPARFSGSGSGTDFTLTISSLEP

EDFAVYYCQQRSHWLTFGGGTKVEIKRTV

The present inventors have found that an anti-CD40 antibody 4D11 (having an IgG4 subclass) and its variant 4D11PE (prepared by digesting, with BglII and NheI, a DNA fragment containing the heavy and light chains of the 4D11 antibody gene; purifying the resulting fragment; and then ligating the fragment into an N5KG4PE vector (IDEC Pharmaceuticals); N5KG4PE and N5KG4P contain S228P and L235E point mutations and an S228P point mutation, respectively, in the IgG4 constant region) form approximately 10% aggregates under conditions involving the charge of their culture supernatants onto a Protein A column (Amersham Biosciences), elution with 0.1 M citric acid buffer (pH 2.7), and subsequent incubation at 37° C. for 1 minute and for 10 minutes, whereas 4D114D11G1 comprising the 4D11 constant region derived from IgG1 forms few aggregates (JP Patent Publication (Kokai) No. 2003-431408A). Likewise, in order to identify a region in IgG1 involved in the suppression of aggregate formation at low pH by use of domain swap variant antibodies for IgG2, domain swap variant antibodies IgG[1/1/2/2] ([1/1/2/2] refers to CH1, hinge, CH2, and CH3 domains in order from the left and means that the CH1 domain is derived from IgG1, the hinge domain is derived form IgG1, the CH2 domain is derived from IgG2, and the CH3 domain is derived from IgG2; hereinafter, interpreted in the same manner), IgG[2/2/1/1], IgG[2/2/1/2], and IgG[2/2/2/1] were prepared as described below.

To prepare IgG[1/1/2/2], N5KG1-Val Lark (IDEC Pharmaceuticals; hereinafter, abbreviated to N5KG1) was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and 24ch4: AGGGGTCCGGGAGATCATGAGAGTGTC-CTT (SEQ ID NO: 10). At the same time, an antibody expression vector N5KG2 (IDEC Pharmaceuticals, U.S. Pat. No. 6,001,358; "G2" means that its heavy chain constant region is derived from IgG2; hereinafter, interpreted in the same manner) was used as a template to perform 15 cycles of reaction at 98° C. for 1 second, 60° C. for 30 seconds, and 72° C. for 30 seconds using primers 24ch3: AAGGACACTCTCAT-GATCTCCCGGACCCCT (SEQ ID NO: 11) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG1122.

To prepare IgG[2/2/1/1], N5KG2 was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and 24ch4: AGGGGTCCGGGAGATCATGAGAGTGTCCTT (SEQ ID NO: 10). At the same time, N5KG1 was used as a template to perform 15 cycles of reaction at 98° C. for 1 second, 60° C. for 30 seconds, and 72° C. for 30 seconds using primers 24ch3: AAGGACACTCTCATGATCTCCCGGACCCCT (SEQ ID NO: 11) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG2211.

To prepare IgG[2/2/1/2], the N5KG2211 thus prepared was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and CH3consR: GGTGTACACCTGTG-GCTCTCGGGGCTGCCC (SEQ ID NO: 13). At the same time, N5KG2 was used as a template to perform 15 cycles of reaction at 98° C. for 1 second, 60° C. for 30 seconds, and 72° C. for 30 seconds using primers CH3cons: GGGCAGC-CCCGAGAGCCACAGGTGTACACC (SEQ ID NO: 14) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG2212.

To prepare IgG[2/2/2/1], N5KG2 was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and CH3consR: GGTGTACACCTGTGGCTCTCGGGGCT-GCCC (SEQ ID NO: 13). At the same time, N5KG1 was used as a template to perform 15 cycles of reaction at 98° C. for 1 second, 60° C. for 30 seconds, and 72° C. for 30 seconds using primers CH3cons: GGGCAGCCCCGAGAGCCACAGGT-GTACACC (SEQ ID NO: 14) and linkH2: tgatcatacgtagatat-cacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG2221.

Each of the expression vectors was digested with BglII and NheI, and the light and heavy chain variable regions of the 341-1-19 antibody were inserted thereinto to complete expression vectors.

Moreover, 341G2Ser and 2105G2Ser were prepared as the antibody having the light and heavy chain variable regions of an antibody produced by a hybridoma KM341-1-19 (Accession No. BP-7759) and the antibody having the light and heavy chain variable regions of an antibody produced by a hybridoma 2105 (Accession No. BP-8024), respectively.

The boundary between the signal sequence and the variable region in the nucleotide sequence (SEQ ID NO: 15) of the heavy chain of the 341G2Ser is positioned between [adenine] ([A]) at the 60th position and cytosine (C) at the 61st position, while the boundary between the variable region and the constant region is positioned between adenine (A) at the 444th position and guanine (G) at the 445th position (examined with gene sequence prediction software Signal P ver. 2).

The boundary between the signal sequence and the variable region in the amino acid sequence (SEQ ID NO: 16) of the heavy chain of the 341G2Ser is positioned between serine (S) at the 20th position and glutamine (Q) at the 21st position, while the boundary between the variable region and the constant region is positioned between serine (S) at the 148th position and alanine (A) at the 149th position.

Thus, the nucleotide sequence of the heavy chain variable region of the 341G2Ser reaches from cytosine (C) at the 61st position to adenine (A) at the 444th position in SEQ ID NO: 15. The amino acid sequence of the heavy chain variable region of the 341G2Ser reaches from glutamine (Q) at the 21st position to serine (S) at the 148th position in SEQ ID NO: 16.

```
341G2Ser heavy chain full-length nucleotide
sequence
                                      (SEQ ID NO: 15)
ATGTCTGTCTCCTTCCTCATCTTCCTGCCCGTGCTGGGCCTCCCATGGGG

TGTCCTGTCACAGGTCCAACTGCAGCAGTCAGGTCCAGGACTGGTGAAGC

CCTCGCAGACCCTCTCACTCACCTGTGCCATCTCCGGGGACAGTGTCTCT

AGCAACAGTGCTACTTGGAACTGGATCAGGCAGTCCCCATCGAGAGACCT
```

```
TGAGTGGCTGGGAAGGACATACTACAGGTCCAAGTGGTATCGTGATTATG

TAGGATCTGTGAAAAGTCGAATAATCATCAACCCAGACACATCCAACAAC

CAGTTCTCCCTGCAGCTGAACTCTGTGACTCCCGAGGACACGGCTATATA

TTACTGTACAAGAGCACAGTGGCTGGGAGGGGATTACCCCTACTACTACA

GTATGGACGTCTGGGGCCAAGGGACCACGGTCACCGTCTCCTCAGCTAGC

ACCAAGGGCCCATCGGTCTTCCCCCTGGCGCCCTGCTCCAGGAGCACCTC

CGAGAGCACAGCGGCCCTGGGCTGCCTGGTCAAGGACTACTTCCCCGAAC

CGGTGACGGTGTCGTGGAACTCAGGCGCTCTGACCAGCGGCGTGCACACC

TTCCCAGCTGTCCTACAGTCCTCAGGACTCTACTCCCTCAGCAGCGTGGT

GACCGTGCCCTCCAGCAACTTCGGCACCCAGACCTACACCTGCAACGTAG

ATCACAAGCCCAGCAACACCAAGGTGGACAAGACAGTTGAGCGCAAATGT

TGTGTCGAGTGCCCACCGTGCCCAGCACCACCTGTGGCAGGACCGTCAGT

CTTCCTCTTCCCCCCAAAACCCAAGGACACCCTCATGATCTCCCGGACCC

CTGAGGTCACGTGCGTGGTGGTGGACGTGAGCCACGAAGACCCCGAGGTC

CAGTTCAACTGGTACGTGGACGGCGTGGAGGTGCATAATGCCAAGACAAA

GCCACGGGAGGAGCAGTTCAACAGCACGTTCCGTGTGGTCAGCGTCCTCA

CCGTTGTGCACCAGGACTGGCTGAACGGCAAGGAGTACAAGTGCAAGGTC

TCCAACAAAGGCCTCCCAGCCTCCATCGAGAAAACCATCTCCAAACCAAA

GGGCAGCCCCGAGAACCACAGGTGTACACCCTGCCCCCATCCCGGGAGGA

GATGACCAAGAACCAGGTCAGCCTGACCTGCCTGGTCAAAGGCTTCTACC

CCAGCGACATCGCCGTGGAGTGGGAGAGCAATGGGCAGCCGGAGAACAAC

TACAAGACCACACCTCCCATGCTGGACTCCGACGGCTCCTTCTTCCTCTA

CAGCAAGCTCACCGTGGACAAGAGCAGGTGGCAGCAGGGGAACGTCTTCT

CATGCTCCGTGATGCATGAGGCTCTGCACAACCACTACACGCAGAAGAGC

CTCTCCCTGTCTCCGGGTAAATGA
```

341G2Sser heavy chain full-length amino acid sequence
(SEQ ID NO: 16)
```
MSVSFLIFLPVLGLPWGVLSQVQLQQSGPGLVKPSQTLSLTCAISGDSVS

SNSATWNWIRQSPSRDLEWLGRTYYRSKWYRDYVGSVKSRIIINPDTSNN

QFSLQLNSVTPEDTAIYYCTRAQWLGGDYPYYYSMDVWGQGTTVTVSSAS

TKGPSVFPLAPCSRSTSESTAALGCLVKDYFPEPVTVSWNSGALTSGVHT

FPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEV

QFNWYVDGVEVHNAKTKPREEQFNSTFRVVSVLTVVHQDWLNGKEYKCKV

SNKGLPASIEKTISKTKGQPREPQVYTLPPSREEMTKNQVSLTCLVKGFY

PSDIAVEWESNGQPENNYKTTPPMLDSDGSFFLYSKLTVDKSRWQQGNVF

SCSVMHEALHNHYTQKSLSLSPGK
```

The boundary between the signal sequence and the variable region in the nucleotide sequence (SEQ ID NO: 17) of the light chain of the 341G2Ser is positioned between [adenine] ([A]) at the 60th position and guanine (G) at the 61st position, while the boundary between the variable region and the constant region is positioned between adenine (A) at the 372nd position and [cytosine] ([C]) at the 373rd position (examined with gene sequence prediction software Signal P ver. 2).

The boundary between the signal sequence and the variable region in the amino acid sequence (SEQ ID NO: 18) of the light chain of the 341G2Ser is positioned between glycine (G) at the 20th position and glutamic acid (E) at the 21st position, while the boundary between the variable region and the constant region is positioned between lysine (K) at the 124th position and [arginine] ([R]) at the 125th position. Thus, the nucleotide sequence of the light chain variable region of the 341G2Ser reaches from guanine (G) at the 61st position to adenine (A) at the 372nd position in SEQ ID NO: 17. The amino acid sequence of the light chain variable region of the 341G2Ser reaches from glutamic acid (E) at the 21st position to lysine (K) at the 124th position in SEQ ID NO: 18.

341G2Ser light chain full-length nucleotide sequence
(SEQ ID NO: 17)
```
ATGGAAGCCCCAGCTCAGCTTCTCTTCCTCCTGCTACTCTGGCTCCCAGA

TACCACCGGAGAAATTGTGTTGACACAGTCTCCAGCCACCCTGTCTTTGT

CTCCAGGGGAAAGAGCCACCCTCTCCTGCAGGGCCAGTCAGAGTGTTAGC

AGCTACTTAGCCTGGTACCAACAGAAACCTGGCCAGGCTCCCAGGCTCCT

CATCTATGATGCATCCAACAGGGCCACTGGCATCCCAGCCAGGTTCAGTG

GCAGTGGGTCTGGGACAGACTTCACTCTCACCATCAGCAGCCTAGAGCCT

GAAGATTTTGCAGTTTATTACTGTCAGCAGCGTAGCAACACTTTCGGCCC

TGGGACCAAAGTGGATATCAAACGTACGGTGGCTGCACCATCTGTCTTCA

TCTTCCCGCCATCTGATGAGCAGTTGAAATCTGGAACTGCCTCTGTTGTG

TGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGG

ACAGCAAGGACAGCACCTACAGCCTCAGCAGCACCCTGACGCTGAGCAAA

GCAGACTACGAGAAACACAAAGTCTACGCCTGCGAAGTCACCCATCAGGG

CCTGAGCTCGCCCGTCACAAAGAGCTTCAACAGGGGAGAGTGTTGA
```

341G2Ser light chain full-length amino acid sequence
(SEQ ID NO: 18)
```
MEAPAQLLFLLLLWLPDTTGEIVLTQSPATLSLSPGERATLSCRASQSVS

SYLAWYQQKPGQAPRLLIYDASNRATGIPARFSGSGSGTDFTLTISSLEP

EDFAVYYCQQRSNTFGPGTKVDIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC
```

The boundary between the signal sequence and the variable region in the nucleotide sequence (SEQ ID NO: 19) of the heavy chain of the 2105G2Ser is positioned between [thymine] ([T]) at the 57th position and guanine (G) at the 58th position, while the boundary between the variable region and the constant region is positioned between adenine (A) at the 426th position and guanine (G) at the 427th position (examined with gene sequence prediction software Signal P ver. 2).

The boundary between the signal sequence and the variable region in the amino acid sequence (SEQ ID NO: 20) of the heavy chain of the 2105G2Ser is positioned between cysteine (C) at the 19th position and glutamic acid (E) at the 20th position, while the boundary between the variable region and the constant region is positioned between serine (S) at the 142nd position and alanine (A) at the 143rd position.

Thus, the nucleotide sequence of the heavy chain variable region of the 2105G2Ser reaches from guanine (G) at the 58th position to adenine (A) at the 426th position in SEQ ID NO: 19. The amino acid sequence of the heavy chain variable region of the 2105G2Ser reaches from glutamic acid (E) at the 20th position to serine (S) at the 142nd position in SEQ ID NO: 20.

2105G2Ser heavy chain full-length nucleotide sequence
(SEQ ID NO: 19)
ATGGAGTTGGGACTGAGCTGGATTTTCCTTTTGGCTATTTTAAAAGGTGT
CCAGTGTGAAGTGCAGCTGGTGGAGTCTGGGGGAGGCTTGGTACAGCCTG
GCAGGTCCCTGAGACTCTCCTGTGCAGCCTCTGGATTCACCTTTGATGAT
TATGCCATGCACTGGGTCCGGCAAGCTCCAGGGAAGGGCCTGGAGTGGGT
CTCAGGTATTAGTTGGAATAGTGGTAGCTTGGTGCATGCGGACTCTGTGA
AGGGCCGATTCACCATCTCCAGAGACAACGCCAAGAACTCCCTGTATCTG
CAAATGAACAGTCTGAGAGCTGAGGACACGGCCTTGTATTACTGTGCAAG
AGATAGGCTATTTCGGGGAGTTAGGTACTACGGTATGGACGTCTGGGGCC
AAGGGACCACGGTCACCGTCTCCTCAGCTAGCACCAAGGGCCCATCGGTC
TTCCCCCTGGCGCCCTGCTCCAGGAGCACCTCCGAGAGCACAGCGGCCCT
GGGCTGCCTGGTCAAGGACTACTTCCCCGAACCGGTGACGGTGTCGTGGA
ACTCAGGCGCTCTGACCAGCGGCGTGCACACCTTCCCAGCTGTCCTACAG
TCCTCAGGACTCTACTCCCTCAGCAGCGTGGTGACCGTGCCCTCCAGCAA
CTTCGGCACCCAGACCTACACCTGCAACGTAGATCACAAGCCCAGCAACA
CCAAGGTGGACAAGACAGTTGAGCGCAAATGTTGTGTCGAGTGCCCACCG
TGCCCAGCACCACCTGTGGCAGGACCGTCAGTCTTCCTCTTCCCCCCAAA
ACCCAAGGACACCCTCATGATCTCCCGGACCCCTGAGGTCACGTGCGTGG
TGGTGGACGTGAGCCACGAAGACCCCGAGGTCCAGTTCAACTGGTACGTG
GACGGCGTGGAGGTGCATAATGCCAAGACAAAGCCACGGGAGGAGCAGTT
CAACAGCACGTTCCGTGTGGTCAGCGTCCTCACCGTTGTGCACCAGGACT
GGCTGAACGGCAAGGAGTACAAGTGCAAGGTCTCCAACAAAGGCCTCCCA
GCCTCCATCGAGAAAACCATCTCCAAAACCAAAGGGCAGCCCCGAGAACC
ACAGGTGTACACCCTGCCCCCATCCCGGGAGGAGATGACCAAGAACCAGG
TCAGCCTGACCTGCCTGGTCAAAGGCTTCTACCCCAGCGACATCGCCGTG
GAGTGGGAGAGCAATGGGCAGCCGGAGAACAACTACAAGACCACACCTCC
CATGCTGGACTCCGACGGCTCCTTCTTCCTCTACAGCAAGCTCACCGTGG
ACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGG
TAAATGA 2105G2Ser heavy chain full-length amino acid sequence
(SEQ ID NO: 20)
MELGLSWIFLLAILKGVQCEVQLVESGGGLVQPGRSLRLSCAASGFTFDD
YAMHWVRQAPGKGLEWVSGISWNSGSLVHADSVKGRFTISRDNAKNSLYL
QMNSLRAEDTALYYCARDRLFRGVRYYGMDVWGQGTTVTVSSASTKGPSV
FPLAPCSRSTSESTAALGCLVKDYFPEPVTVSWNSGALTSGVHTFPAVLQ
SSGLYSLSSVVTVPSSNFGTQTYTCNVDHKPSNTKVDKTVERKCCVECPP -continued
CPAPPVAGPSVFLFPPKPKDTLMISRTPEVTCVVVDVSHEDPEVQFNWYV
DGVEVHNAKTKPREEQFNSTFRVVSVLTVVHQDWLNGKEYKCKVSNKGLP
ASIEKTISKTKGQPREPQVYTLPPSREEMTKNQVSLTCLVKGFYPSDIAV
EWESNGQPENNYKTTPPMLDSDGSFFLYSKLTVDKSRWQQGNVFSCSVMH
EALHNHYTQKSLSLSPGK The boundary between the signal sequence and the variable region in the nucleotide sequence (SEQ ID NO: 21) of the light chain of the 2105G2Ser is positioned between [adenine] ([A]) at the 60th position and guanine (G) at the 61st position, while the boundary between the variable region and the constant region is positioned between adenine (A) at the 378th position and [cytosine] ([C]) at the 379th position (examined with gene sequence prediction software Signal P ver. 2).

The boundary between the signal sequence and the variable region in the amino acid sequence (SEQ ID NO: 22) of the light chain of the 2105G2Ser is positioned between glycine (G) at the 20th position and glutamic acid (E) at the 21st position, while the boundary between the variable region and the constant region is positioned between lysine (K) at the 126th position and [arginine] ([R]) at the 127th position. Thus, the nucleotide sequence of the light chain variable region of the 2105G2Ser reaches from guanine (G) at the 61st position to adenine (A) at the 378th position in SEQ ID NO: 21. The amino acid sequence of the light chain variable region of the 2105G2Ser reaches from glutamic acid (E) at the 21st position to lysine (K) at the 126th position in SEQ ID NO: 22.

2105G2Ser light chain full-length nucleotide sequence
(SEQ ID NO: 21)
ATGGAAGCCCCAGCTCAGCTTCTCTTCCTCCTGCTACTCTGGCTCCCAGA
TACCACCGGAGAAATTGTGTTGACACAGTCTCCAGCCACCCTGTCTTTGT
CTCCAGGGGAAAGAGCCACCCTCTCCTGCAGGGCCAGTCAGAGTGTTAGC
AGCTACTTAGCCTGGTACCAACAGAAACCTGGCCAGGCTCCCAGGCTCCT
CATCTATGATGCATCCAACAGGGCCACTGGCATCCCAGCCAGGTTCAGTG
GCAGTGGGTCTGGGACAGACTTCACTCTCACCATCAGCAGCCTAGAGCCT
GAAGATTTTGCAGTTTATTACTGTCAGCAGCGTAGCCACTGGCTCACTTT
CGGCGGGGGGACCAAGGTGGAGATCAAACGTACGGTGGCTGCACCATCTG
TCTTCATCTTCCCGCCATCTGATGAGCAGTTGAAATCTGGAACTGCCTCT
GTTGTGTGCCTGCTGAATAACTTCTATCCCAGAGAGGCCAAAGTACAGTG
GAAGGTGGATAACGCCCTCCAATCGGGTAACTCCCAGGAGAGTGTCACAG
AGCAGGACAGCAAGGACAGCACCTACAGCCTCAGCAGCACCCTGACGCTG
AGCTGAGCAAAGCAGACTACGAGAAACACAAAGTCTACGCCTGCGAAGTC
ACCCATCAGGGCCTGAGCTCGCCCGTCACAAAGAGCTTCAACAGGGGAGA
GTGTTGA 2105G2Ser light chain full-length amino acid sequence
(SEQ ID NO: 22)
MEAPAQLLFLLLLWLPDTTGEIVLTQSPATLSLSPGERATLSCRASQSVS
SYLAWYQQKPGQAPRLLIYDASNRATGIPARFSGSGSGTDFTLTISSLEP
EDFAVYYCQQRSHWLTFGGGTKVEIKRTVAAPSVFIFPPSDEQLKSGTAS -continued
VVCLLNNFYPREAKVQWKVDNALQSGNSQESVTEQDSKDSTYSLSSTLTL

SKADYEKHKVYACEVTHQGLSSPVTKSFNRGEC

Example 2

Expression and Purification of Domain Swap Variant Anti-CD40 Antibodies and Amino Acid Substitution Variant Antibodies Each expression vector DNA prepared in Example 1 was prepared with EndoFree Plasmid Kit (Qiagen) and introduced into suspension 293 cells (Invitrogen Life Technologies) by use of FreeStyle™ 293 Expression System (Invitrogen Life Technologies) according to the manufacturer's recommended protocol. A culture supernatant containing each antibody was obtained by transient expression. The culture supernatant (approximately 500 µg in terms of IgG) filtered with a membrane filter (MILLIPORE) of 0.22 µm in pore size was charged onto an antibody purification affinity column HiTrap rProtein A FF (column volume of 1 ml) (Amersham Biosciences). After washing with PBS (-), the antibodies were eluted with 20 mM citric acid buffer. (pH 3.4) and collected into a tube containing 200 mM phosphoric acid buffer (pH 7.0).

Example 3

Measurement of Aggregate Contents of Antibody Solutions

The aggregate contents of the antibody solutions were analyzed with a high-performance liquid chromatograph apparatus (manufactured by Shimadzu) and a TSK-G3000 SW column (manufactured by Tosoh) using 20 mM sodium phosphate and 500 mM NaCl pH 7.0 as solvents. The elution positions were compared with a gel filtration HPLC molecular weight marker (Oriental Yeast) (Cat No. 40403701) to thereby identify the peaks of the antibody protein monomers and higher-molecular-weight aggregates. The aggregate contents were calculated from each peak area.

Example 4

Evaluation of Stability of Domain Swap Variant Anti-CD40 Antibodies

The aggregate content of each antibody sample completely purified by the method shown in Example 2 was measured by the method of Example 3 and was thereby confirmed to be 0% in all the samples. These purified antibody samples (300 µl each) were separately adjusted to pH 3.5 by the addition of 60 µl of a buffer (pH 2.7) comprising 200 mM sodium citrate and 50 mM NaCl and incubated at 37° C. for 10 minutes or 60 minutes. Then, the low-pH treated solutions (150 µl each) were separately neutralized by the addition of 37.5 µl of 500 mM sodium phosphate buffer (pH 8.0). The aggregate contents of the antibody solutions after low-pH treatment were measured by the method shown in Example 3.

As a result, the antibody in which at least the CH2 domain was derived from IgG1 (IgG[2/2/1/1] or IgG[2/2/1/2]) was shown to be as stable at low pH as antibodies comprising the whole constant region derived from IgG1 (Table 1). Table 1 shows the stability of the IgG2/IgG1 domain swap variant antibodies at low pH.

TABLE 1

| Purified antibody | Aggregate (%) | |
|---|---|---|
| | 10 min.* | 60 min.* |
| 341-G1 | 0.00 | 0.00 |
| 341-G2Ser | 1.25 | 4.96 |
| 341-G [1/1/2/2] | 0.73 | 3.10 |
| 341-G [2/2/1/1] | 0.00 | 0.00 |
| 341-G [2/2/1/2] | 0.00 | 0.00 |
| 341-G [2/2/2/1] | 1.33 | 4.58 |

*Incubation time at low pH

Example 5

Preparation of One-amino Acid Variant Having One-amino Acid Variation in IgG2 CH2 Domain The domain swap variant antibody IgG[2/2/1/2] in which the CH2 domain of the constant region of the 341-G2Ser antibody was derived from IgG1 was found in Example 4 to form few aggregates. Therefore, to further narrow down candidate amino acid residues contributing to the suppression of aggregate formation, each variant comprising the IgG2 amino acid residue converted to an IgG1 amino acid residue (341-G2Ser[Q274K] (the Gln residue at the 274th position was converted to Lys; hereinafter, interpreted in the same manner), 341-G2Ser[F296Y], 341-G2Ser[F300Y], 341-G2Ser[V309L], 341-G2Ser[G327A], and 341-G2Ser[T339A]) was prepared by focusing on 6 amino acid residues (at the 274th, 296th, 300th, 309th, 327th, and 339th positions designated by the EU index of Kabat et al.) different between IgG1 and IgG4 present within the CH2 domain of the 341G2Ser antibody. The DNA of an anti-CD40 antibody 341-G2Ser expression vector (N5KG2Ser-341) was used as a template to prepare each kind of variant DNA encoding the antibody having an amino acid substitution in the constant region by site-specific mutagenesis using GeneEditor™ in vitro Site-Directed Mutagenesis System (Promega). Oligonucleotides (5'-terminally phosphorylated) for mutagenesis used were Q274K: AGACCCCGAG GTCAAGTTCA ACTGGTACGT G (SEQ ID NO: 23), F296Y: CGGGAGGAGC AGTACAACAG CACGTTCC (SEQ ID NO: 24), F300Y: AGTTCAACAG CACGTACCGT GTGGTCAGC (SEQ ID NO: 25), V309L: GCGTCCTCAC CGTTCTGCAC CAGGACTGG (SEQ ID NO: 26), Q327A: AGGTCTCCAA CAAAGCCCTC CCAGCCTCC (SEQ ID NO: 27), and T339A: GAAAAC-CATC TCCAAAGCCA AAGGGCAGCC C (SEQ ID NO: 28). The oligonucleotide for mutagenesis of interest and Selection Oligonucleotide included in the kit were annealed to the template DNA to synthesize a mutagenized strand. Then, variants were selected by use of the principle that only variants can amplify in the presence of GeneEditor™ Antibiotic Selection Mix. More specifically, the dsDNA template was incubated at room temperature for 5 minutes under alkali conditions (0.2 M NaOH and 0.2 mM EDTA (final concentration)), then neutralized by the addition of 1/10 volumes of 2 M ammonium acetate (pH 4.6), and collected by ethanol precipitation. In different tubes prepared for the 6 kinds of variants, the oligonucleotide for mutagenesis, Selection Oligonucleotide (Top Select Oligo, 5'-terminally phosphorylated) for acquisition of new antibiotic resistance, and an annealing buffer included in the kit were added to the template DNA treated by alkali denaturation. Then, annealing was performed at a temperate kept at 75° C. for 5 minutes and gradually lowered to 37° C. Next, to perform variant strand synthesis and ligation, Synthesis 10×buffer, T4 DNA Polymerase, and T4 DNA ligase included in the kit were added thereto to perform reaction at 37° C. for 90 minutes. Plasmid DNA was prepared from transformant E. coli obtained from competent cells BMH 71-18 mutS transfected and cultured in the presence of GeneEditor™ Antibiotic Selection Mix. Competent cells JM109 were further transformed with the DNA and then inoculated onto an LB plate containing Gene-Editor™ Antibiotic Selection Mix. The transformants of each variant formed on the plate were cultured. Plasmid DNA was purified therefrom and analyzed for its nucleotide sequence. As a result of DNA nucleotide sequence analysis, the expression vectors of 6 kinds of anti-CD40 antibody variants comprising the amino acid variation of interest introduced therein were obtained. The plasmid DNAs expressing these one-amino acid substitution anti-CD40 antibody variant proteins were respectively designated as N5KG2Ser-341-Q274K, N5KG2Ser-341-F296Y, N5KG2Ser-341-F300Y, N5KG2Ser-341-V309L, N5KG2Ser-341-G327A, and N5KG2Ser-341-T339A.

Example 6

Evaluation of Suppression of Aggregate Formation of One-amino Acid Variants

The one-amino acid variant antibodies were expressed and purified according to Example 2 from their expression vectors of Example 5 and subjected to low-pH treatment according to Example 4. Aggregate contents were measured according to Example 3.

As a result, a variant whose aggregate formation at low pH was suppressed by the one-amino acid variation at the same level as IgG1 or IgG[2/2/11/2] was not found, whereas the aggregate formation was confirmed to be suppressed partially, but not completely, in the 341-G2Ser[F300Y], 341-G2Ser[V309L], and 341-G2Ser[T339A] (Table 2). Table 2 shows the stability of the antibodies having a one-IgG1-amino acid substitution introduced into the IgG2 CH2 domain at low pH.

TABLE 2

| Purified antibody | Aggregate (%) | |
|---|---|---|
| | 10 min.* | 60 min.* |
| 341-G2Ser [Q274K] | 1.31 | 4.79 |
| 341-G2Ser [F296Y] | 0.93 | 3.88 |
| 341-G2Ser [F300Y] | 0.00 | 2.24 |
| 341-G2Ser [V309L] | 0.00 | 2.61 |
| 341-G2Ser [G327A] | 0.94 | 4.35 |
| 341-G2Ser [T339A] | 0.00 | 3.66 |
| 341-G1 | 0.00 | 0.00 |
| 341-G2Ser | 0.97 | 4.80 |

*Incubation time at low pH

Example 7

As shown in Example 6, the variants (341-G2Ser[F300Y], 341-G2Ser[V309L], and 341-G2Ser[T339A]) whose aggregate formation was partially suppressed were found from the study using the variants of the 341G2Ser antibody having a one-amino acid substitution in the CH2 domain. Therefore, to further promote the suppression of aggregate formation, variants having any two or all of the 3 one-amino acid variations in combination were prepared. The prepared variants were 4 kinds: 341-G2Ser[F300Y/V309L] (the amino acid residue F at the 300th position was converted to Y, and V at the 309th position was further converted to L; hereinafter, interpreted in the same manner), 341-G2Ser[F300Y/T339A], 341-G2Ser [V309L/T339A], and 341-G2Ser[F300Y/V309L/T339A] (F at the 300th position was converted to Y, V at the 309th position was converted to L, and T at the 339th position was converted to A). A method for the variant expression vector preparation was performed according to the site-specific mutagenesis of Example 5 using GeneEditor™ in vitro Site-Directed Mutagenesis System (Promega) except that to perform mutagenesis at several sites, a newly prepared longer oligonucleotide for mutagenesis was annealed to the template vector DNA, or two or more of the oligonucleotides for mutagenesis of Example 5 were simultaneously annealed thereto). The oligonucleotides for mutagenesis used were F300YV309L: AGTTCAACAG CACGTACCGT GTGGT-CAGCG TCCTCACCGT TCTGCACCAG GACTGG (SEQ ID NO: 29) for 341-G2Ser[F300Y/V309L] preparation, the F300Y and T339A used in Example 5 for 341-G2Ser[F300Y/T339A] preparation, V309L and T339A for 341-G2Ser [V309L/T339A] preparation, and F300YV309L and T339A for 341-G2Ser[F300Y/V309L/T339A] preparation. Candidate plasmid DNA of each variant antibody expression vector obtained by the site-specific mutagenesis shown in Example 5 was selected by DNA nucleotide sequence analysis to obtain expression vectors of 4 kinds of anti-CD40 antibody variants having the amino acid variation of interest introduced therein. The plasmid DNAs expressing these anti-CD40 antibody variant proteins were respectively designated as N5KG2Ser-341-F300Y/V309L, N5KG2Ser-341-F300Y/T339A, N5KG2Ser-341-V309L/T339A, and N5KG2Ser-341-F300Y/V309L/T339A.

A nucleotide sequence encoding the heavy chain of the 341-G2Ser[F300Y/V309L/T339A] and an amino acid sequence of the heavy chain are shown below.

```
341-G2Ser[F300Y/V309L/T339A] heavy chain
nucleotide sequence
                                            (SEQ ID NO: 30)
ATGTCTGTCTCCTTCCTCATCTTCCTGCCCGTGCTGGGCCTCCCATGGGG

TGTCCTGTCACAGGTCCAACTGCAGCAGTCAGGTCCAGGACTGGTGAAGC

CCTCGCAGACCCTCTCACTCACCTGTGCCATCTCCGGGGACAGTGTCTCT

AGCAACAGTGCTACTTGGAACTGGATCAGGCAGTCCCCATCGAGAGACCT

TGAGTGGCTGGGAAGGACATACTACAGGTCCAAGTGGTATCGTGATTATG

TAGGATCTGTGAAAAGTCGAATAATCATCAACCCAGACACATCCAACAAC

CAGTTCTCCCTGCAGCTGAACTCTGTGACTCCCGAGGACACGGCTATATA

TTACTGTACAAGAGCACAGTGGCTGGGAGGGGATTACCCCTACTACTACA

GTATGGACGTCTGGGGCCAAGGGACCACGGTCACCGTCTCCTCAGCTAGC

ACCAAGGGCCCATCGGTCTTCCCCCTGGCGCCCTGCTCCAGGAGCACCTC

CGAGAGCACAGCGGCCCTGGGCTGCCTGGTCAAGGACTACTTCCCCGAAC

CGGTGACGGTGTCGTGGAACTCAGGCGCTCTGACCAGCGGCGTGCACACC

TTCCCAGCTGTCCTACAGTCCTCAGGACTCTACTCCCTCAGCAGCGTGGT

GACCGTGCCCTCCAGCAACTTCGGCACCCAGACCTACACCTGCAACGTAG

ATCACAAGCCCAGCAACACCAAGGTGGACAAGACAGTTGAGCGCAAATGT

TGTGTCGAGTGCCCACCGTGCCCAGCACCACCTGTGGCAGGACCGTCAGT

CTTCCTCTTCCCCCCAAAACCCAAGGACACCCTCATGATCTCCCGGACCC
```

-continued
```
CTGAGGTCACGTGCGTGGTGGTGGACGTGAGCCACGAAGACCCCGAGGTC

CAGTTCAACTGGTACGTGGACGGCGTGGAGGTGCATAATGCCAAGACAAA

GCCACGGGAGGAGCAGTTCAACAGCACGTACCGTGTGGTCAGCGTCCTCA

CCGTTCTGCACCAGGACTGGCTGAACGGCAAGGAGTACAAGTGCAAGGTC

TCCAACAAAGGCCTCCCAGCCTCCATCGAGAAAACCATCTCCAAAGCCAA

AGGGCAGCCCCGAGAACCACAGGTGTACACCCTGCCCCCATCCCGGGAGG

AGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAA

CTACAAGACCACACCTCCCATGCTGGACTCCGACGGCTCCTTCTTCCTCT

ACAGCAAGCTCACCGTGGACAAGAGCAGGTGGCAGCAGGGGAACGTCTTC

TCATGCTCCGTGATGCATGAGGCTCTGCACAACCACTACACGCAGAAGAG

CCTCTCCCTGTCTCCGGGTAAATGA
```

The boundary between the signal sequence and the variable region in SEQ ID NO: 30 is positioned between adenine (A) at the 60th position and cytosine (C) at the 61st position (examined with gene sequence prediction software Signal P ver. 2).

341-G2Ser[F300Y/V309L/T339A] heavy chain amino acid sequence
(SEQ ID NO: 31)
```
MSVSFLIFLPVLGLPWGVLSQVQLQQSGPGLVKPSQTLSLTCAISGDSVS

SNSATWNWIRQSPSRDLEWLGRTYYRSKWYRDYVGSVKSRIIINPDTSNN

QFSLQLNSVTPEDTAIYYCTRAQWLGGDYPYYYSMDVWGQGTTVTVSSAS

TKGPSVFPLAPCSRSTSESTAALGCLVKDYFPEPVTVSWNSGALTSGVHT

FPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEV

QFNWYVDGVEVHNAKTKPREEQFNSTYRVVSVLTVLHQDWLNGKEYKCKV

SNKGLPASIEKTISKAKGQPREPQVYTLPPSREEMTKNQVSLTCLVKGFY

PSDIAVEWESNGQPENNYKTTPPMLDSDGSFFLYSKLTVDKSRWQQGNVF

SCSVMHEALHNHYTQKSLSLSPGK
```

The boundary between the signal sequence and the variable region in SEQ ID NO: 31 is positioned between serine (S) at the 20th position and glutamine (Q) at the 21st position (examined with gene sequence prediction software Signal P ver. 2).

A nucleotide sequence encoding the light chain of the 341-G2Ser[F300Y/V309L/T339A] and an amino acid sequence of the light chain are shown below.

341-G2Ser[F300Y/V309L/T339A] light chain nucleotide sequence
(SEQ ID NO: 32)
```
ATGGAAGCCCCAGCTCAGCTTCTCTTCCTCCTGCTACTCTGGCTCCCAGA

TACCACCGGAGAAATTGTGTTGACACAGTCTCCAGCCACCCTGTCTTTGT

CTCCAGGGGAAAGAGCCACCCTCTCCTGCAGGGCCAGTCAGAGTGTTAGC

AGCTACTTAGCCTGGTACCAACAGAAACCTGGCCAGGCTCCCAGGCTCCT

CATCTATGATGCATCCAACAGGGCCACTGGCATCCCAGCCAGGTTCAGTG

GCAGTGGGTCTGGGACAGACTTCACTCTCACCATCAGCAGCCTAGAGCCT

GAAGATTTTGCAGTTTATTACTGTCAGCAGCGTAGCAACACTTTCGGCCC

TGGGACCAAAGTGGATATCAAACGTACGGTGGCTGCACCATCTGTCTTCA

TCTTCCCGCCATCTGATGAGCAGTTGAAATCTGGAACTGCCTCTGTTGTG

TGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGG

ACAGCAAGGACAGCACCTACGCCTCAGCAGCACCCTGACGCTGAGCAAA

GCAGACTACGAGAAACACAAAGTCTACGCCTGCGAAGTCACCCATCAGGG

CCTGAGCTCGCCCGTCACAAAGAGCTTCAACAGGGGAGAGTGTTGA
```

The boundary between the signal sequence and the variable region in SEQ ID NO: 32 is positioned between adenine (A) at the 60th position and guanine (G) at the 61st position (examined with gene sequence prediction software Signal P ver. 2).

341-G2Ser[F300Y/V309L/T339A] light chain amino acid sequence
(SEQ ID NO: 33)
```
MEAPAQLLFLLLLWLPDTTGEIVLTQSPATLSLSPGERATLSCRASQSVS

SYLAWYQQKPGQAPRLLIYDASNRATGIPARFSGSGSGTDFTLTISSLEP

EDFAVYYCQQRSNTFGPGTKVDIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC
```

The boundary between the signal sequence and the variable region in SEQ ID NO: 33 is positioned between glycine (G) at the 20th position and glutamic acid (E) at the 21st position (examined with gene sequence prediction software Signal P ver. 2).

Example 8

Evaluation of Suppression of Aggregate Formation of 341G2Ser Variants

The 341G2Ser variants were expressed and purified according to Example 2 from their expression vectors of Example 7 and subjected to low-pH treatment according to Example 4. Aggregate contents were measured according to Example 3 to evaluate stability at low pH.

As a result, aggregate formation at low pH was confirmed to be suppressed most in the 341-G2Ser[F300Y/V309L/T339A] (Table 3).

TABLE 3

| Purified antibody | Aggregate (%) | |
|---|---|---|
| | 10 min.* | 60 min.* |
| 341-G2Ser [F300Y/V309L] | 0.00 | 1.31 |
| 341-G2Ser [F300Y/T339A] | 0.00 | 1.62 |
| 341-G2Ser [V309L/T339A] | 0.00 | 2.04 |
| 341-G2Ser [F300Y/V309L/T339A] | 0.00 | 0.46 |
| 341-G1 | 0.00 | 0.00 |
| 341-G2Ser | 1.08 | 3.70 |

*Incubation time at low pH

Example 9

Study on Suppression of Aggregate Formation of 2105G2Ser at Low pH

The 2105G2Ser was studied in the same way as the 341G2Ser for whether aggregate formation under low-pH conditions can be suppressed when the antibody was allowed to have the IgG2 constant region having the F300YV309LT339A variation in which 3 amino acids in the CH2 domain were converted to IgG1 amino acids. A DNA fragment containing the light and heavy chain variable regions of N5KG2Ser-341-F300Y/V309L/T339A was excised by digestion with BglII and NheI. The light and heavy chain variable regions of 2105 were inserted instead thereof. The obtained plasmid DNA expressing the 2105 antibody variant protein was designated as N5KG2Ser-2105-F300YV309LT339A.

DNA encoding the full-length H chain of the 2105-G2Ser [F300Y/V309L/T339A] and an amino acid sequence of the H chain are shown below.

```
2105-G2Ser[F300Y/V309L/T339A] heavy chain
nucleotide sequence
                                        (SEQ ID NO: 34)
ATGGAGTTGGGACTGAGCTGGATTTTCCTTTTGGCTATTTTAAAAGGTGT

CCAGTGTGAAGTGCAGCTGGTGGAGTCTGGGGGAGGCTTGGTACAGCCTG

GCAGGTCCCTGAGACTCTCCTGTGCAGCCTCTGGATTCACCTTTGATGAT

TATGCCATGCACTGGGTCCGGCAAGCTCCAGGGAAGGGCCTGGAGTGGGT

CTCAGGTATTAGTTGGAATAGTGGTAGCTTGGTGCATGCGGACTCTGTGA

AGGGCCGATTCACCATCTCCAGAGACAACGCCAAGAACTCCCTGTATCTG

CAAATGAACAGTCTGAGAGCTGAGGACACGGCCTTGTATTACTGTGCAAG

AGATAGGCTATTTCGGGGAGTTAGGTACTACGGTATGGACGTCTGGGGCC

AAGGGACCACGGTCACCGTCTCCTCAGCTAGCACCAAGGGCCCATCGGTC

TTCCCCCTGGCGCCCTGCTCCAGGAGCACCTCCGAGAGCACAGCGGCCCT

GGGCTGCCTGGTCAAGGACTACTTCCCCGAACCGGTGACGGTGTCGTGGA

ACTCAGGCGCTCTGACCAGCGGCGTGCACACCTTCCCAGCTGTCCTACAG

TCCTCAGGACTCTACTCCCTCAGCAGCGTGGTGACCGTGCCCTCCAGCAA

CTTCGGCACCCAGACCTACACCTGCAACGTAGATCACAAGCCCAGCAACA

CCAAGGTGGACAAGACAGTTGAGCGCAAATGTTGTGTCGAGTGCCCACCG

TGCCCAGCACCACCTGTGGCAGGACCGTCAGTCTTCCTCTTCCCCCCAAA

ACCCAAGGACACCCTCATGATCTCCCGGACCCCTGAGGTCACGTGCGTGG

TGGTGGACGTGAGCCACGAAGACCCCGAGGTCCAGTTCAACTGGTACGTG

GACGGCGTGGAGGTGCATAATGCCAAGACAAAGCCACGGGAGGAGCAGTT

CAACAGCACGTACCGTGTGGTCAGCGTCCTCACCGTTCTGCACCAGGACT

GGCTGAACGGCAAGGAGTACAAGTGCAAGGTCTCCAACAAAGGCCTCCCA

GCCTCCATCGAGAAAACCATCTCCAAAGCCAAAGGGCAGCCCCGAGAACC

ACAGGTGTACACCCTGCCCCCATCCCGGGAGGAGATGACCAAGAACCAGG

TCAGCCTGACCTGCCTGGTCAAAGGCTTCTACCCCAGCGACATCGCCGTG

GAGTGGGAGAGCAATGGGCAGCCGGAGAACAACTACAAGACCACACCTCC

CATGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGA
```

The boundary between the signal sequence and the variable region in SEQ ID NO: 34 is positioned between thymine (T) at the 57th position and guanine (G) at the 58th position (examined with gene sequence prediction software Signal P ver. 2).

```
2105-G2Ser[F300Y/V309L/T339A] heavy chain amino
acid sequence
                                        (SEQ ID NO: 35)
MELGLSWIFLLAILKGVQCEVQLVESGGGLVQPGRSLRLSCAASGFTFDD

YAMHWVRQAPGKGLEWVSGISWNSGSLVHADSVKGRFTISRDNAKNSLYL

QMNSLRAEDTALYYCARDRLFRGVRYYGMDVWGQGTTVTVSSASTKGPSV

FPLAPCSRSTSESTAALGCLVKDYFPEPVTVSWNSGALTSGVHTFPAVLQ

SSGLYSLSSVVTVPSSNFGTQTYTCNVDHKPSNTKVDKTVERKCCVECPP

CPAPPVAGPSVFLFPPKDTLMISRTPEVTCVVVDVSHEDPEVQFNWYVDG

VEVHNAKTKPREEQFNSTYRVVSVLTVLHQDWLNGKEYKCKVSNKGLPAS

IEKTISKAKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPGK
```

The boundary between the signal sequence and the variable region in SEQ ID NO: 35 is positioned between cysteine (C) at the 19th position and glutamic acid (E) at the 20th position (examined with gene sequence prediction software Signal P ver. 2).

A nucleotide sequence encoding the light chain of the 2105-G2Ser[F300Y/V309L/T339A] and an amino acid sequence of the light chain are shown below.

```
2105-G2Ser[F300Y/V309L/T339A] light chain
nucleotide sequence
                                        (SEQ ID NO: 36)
ATGGAAGCCCCAGCTCAGCTTCTCTTCCTCCTGCTACTCTGGCTCCCAGA

TACCACCGGAGAAATTGTGTTGACACAGTCTCCAGCCACCCTGTCTTTGT

CTCCAGGGGAAAGAGCCACCCTCTCCTGCAGGGCCAGTCAGAGTGTTAGC

AGCTACTTAGCCTGGTACCAACAGAAACCTGGCCAGGCTCCCAGGCTCCT

CATCTATGATGCATCCAACAGGGCCACTGGCATCCCAGCCAGGTTCAGTG

GCAGTGGGTCTGGGACAGACTTCACTCTCACCATCAGCAGCCTAGAGCCT

GAAGATTTTGCAGTTTATTACTGTCAGCAGCGTAGCCACTGGCTCACTTT

CGGCGGGGGGACCAAGGTGGAGATCAAACGTACGGTGGCTGCACCATCTG

TCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA
```

-continued

TCAGGGCCTGAGCTCGCCCGTCACAAAGAGCTTCAACAGGGGAGAGTGTT

GA

The boundary between the signal sequence and the variable region in SEQ ID NO: 36 is positioned between adenine (A) at the 60th position and guanine (G) at the 61st position (examined with gene sequence prediction software Signal P ver. 2).

2105-G2Ser[F300Y/V309L/T339A] light chain amino acid sequence
(SEQ ID NO: 37)
MEAPAQLLFLLLLWLPDTTGEIVLTQSPATLSLSPGERATLSCRASQSVS

SYLAWYQQKPGQAPRLLIYDASNRATGIPARFSGSGSGTDFTLTISSLEP

EDFAVYYCQQRSHWLTFGGGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

The boundary between the signal sequence and the variable region in SEQ ID NO: 37 is positioned between glycine (G) at the 20th position and glutamic acid (E) at the 21st position (examined with gene sequence prediction software Signal P ver. 2).

Antibodies were expressed and purified by the method of Example 2 from this expression vector and control vectors N5KG2Ser-2105 and N5KG1-2105 and examined for their stability at low pH by the methods of Examples 4 and 3.

As a result, the 2015 antibody, which even comprised an IgG1 constant region, highly formed aggregates and did not exhibit effect as much as 341G2Ser. When the 2105-G2Ser and its variant 2105-G2Ser[F300YV309LT339A] were compared, the latter was confirmed to be enhanced in stability (Table 4).

TABLE 4

| Purified antibody | Aggregate (%) | |
|---|---|---|
| | 10 min.* | 60 min.* |
| 2105-G1 | 0.00 | 13.4 |
| 2105-G2Ser | 2.33 | 48.9 |
| 2105-G2Ser [F300YV309LT339A] | 1.07 | 37.3 |

Example 10

Avidity of Anti-CD40 Antibodies to Ramos Cells

To examine whether the domain swap variant antibodies prepared in Example 2 and the variant antibodies prepared in Example 5 exhibit binding activity at the same level as their original antibodies, the binding activity to Ramos [ATCC] cells expressing CD40 was measured.

Ramos cell lines were suspended at a concentration of $2 \times 10^6$ cells/ml in a staining buffer (SB) of PBS containing 0.1% $NaN_3$ and 2% FCS. The cell suspension (100 µl/well) was dispensed into a 96-well round-bottomed plate (manufactured by Becton, Dickinson and Company). The culture supernatant (50 µl) of each hybridoma was added to the plate and incubated at an ice temperature for 30 minutes. A human IgG1 antibody against human serum albumin was used as a negative control and adjusted with a hybridoma culture medium to a concentration of 2 µg/ml. A 50 µl aliquot thereof was added to the plate and incubated at an ice temperature for 15 minutes. After washing with SB, 50 µl of an R-PE fluorescently labeled anti-human antibody (manufactured by Southern Biotechnology) diluted 250 folds was added thereto and incubated at an ice temperature for 15 minutes. After washing two times with SB, the cells were suspended in 300 to 500 µl of FACS buffer solution. The fluorescence intensity of each cell was measured with FACS (FACSort, FACScan, manufactured by Becton, Dickinson and Company).

Figure 1B:
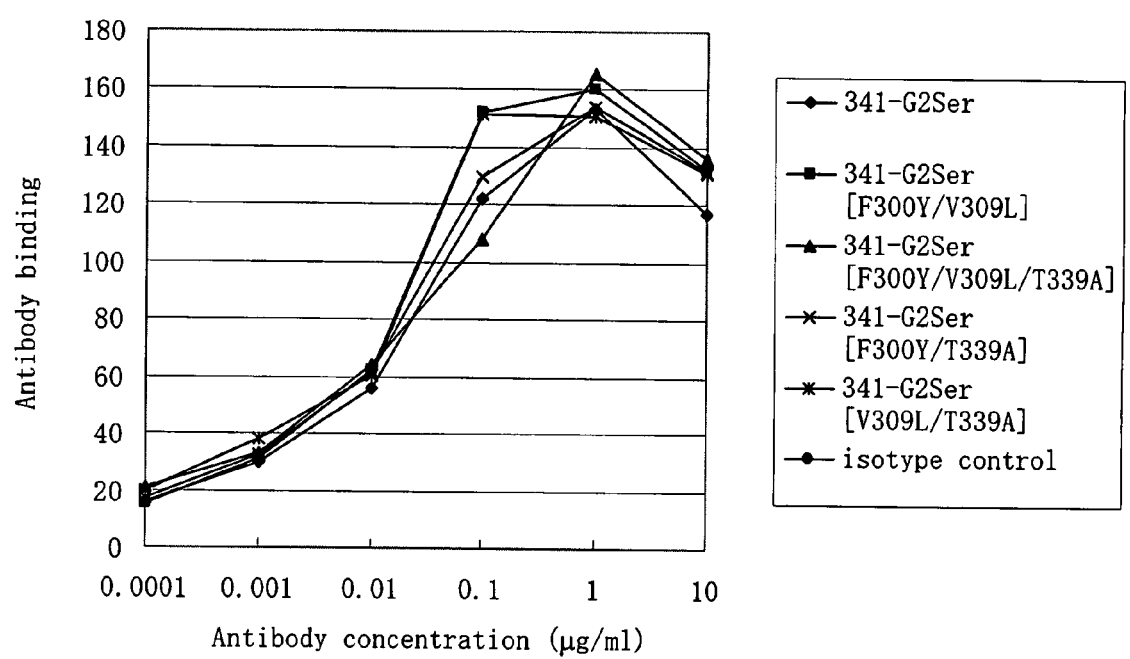
FIG. 1B is a diagram showing the binding activity of variants of an anti-CD40 antibody KM341-1-19 to Ramos cells (Ramos cell binding activity)
Figure 1C:
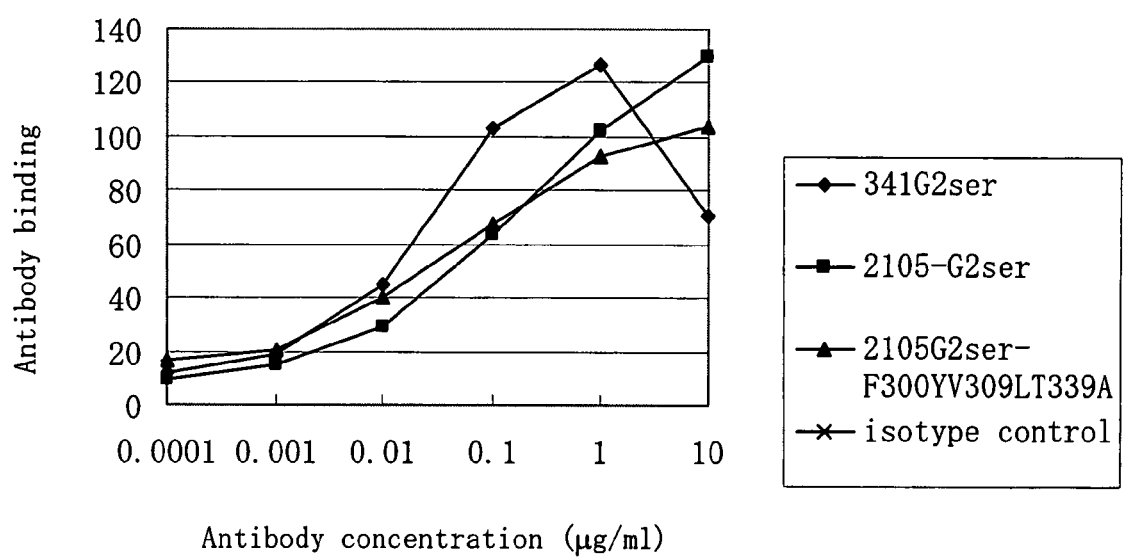
FIG. 1C is a diagram showing the binding activity of variants of anti-CD40 antibodies KM341-1-19 and 2105 to Ramos cells (Ramos cell binding activity)

As a result, difference in binding property was not observed among the domain swap variant antibodies and the variant antibodies (FIGS. 1A, 1B, and 1C). In FIGS. 1A, 1B, and 1C, the unit of the antibody binding represented by the longitudinal axis is average fluorescence intensity. The values of the isotype control shown in FIGS. 1A, 1B, and 1C are 7.15, 7.15, and 5.01, respectively.

Example 11

Promotion of CD95 Expression in Ramos Cells by Anti-CD40 Antibodies 341-1-19 and 2105 are known to be agonist antibodies. The influence of the structural change of the constant regions of the antibodies on their agonist activity was examined. Ramos cells have been observed to have increases in CD95 expression by the addition of CD40 ligands. The agonist activity of the antibodies was examined by using, as an index, whether the addition of the antibodies to the cells causes increases in CD95 expression.

A Ramos cell suspension with a concentration of $1.0 \times 10^6$ cells/ml was inoculated at a concentration of 50 µl/well onto a 96-well plate. The culture supernatant or the purified antibody was added at a concentration of 100 µl/well to the 96-well plate. After overnight culture, the cells were collected and analyzed with FACS using an R-PE labeled anti-CD95 antibody (Pharmingen NJ).

Figure 2A:
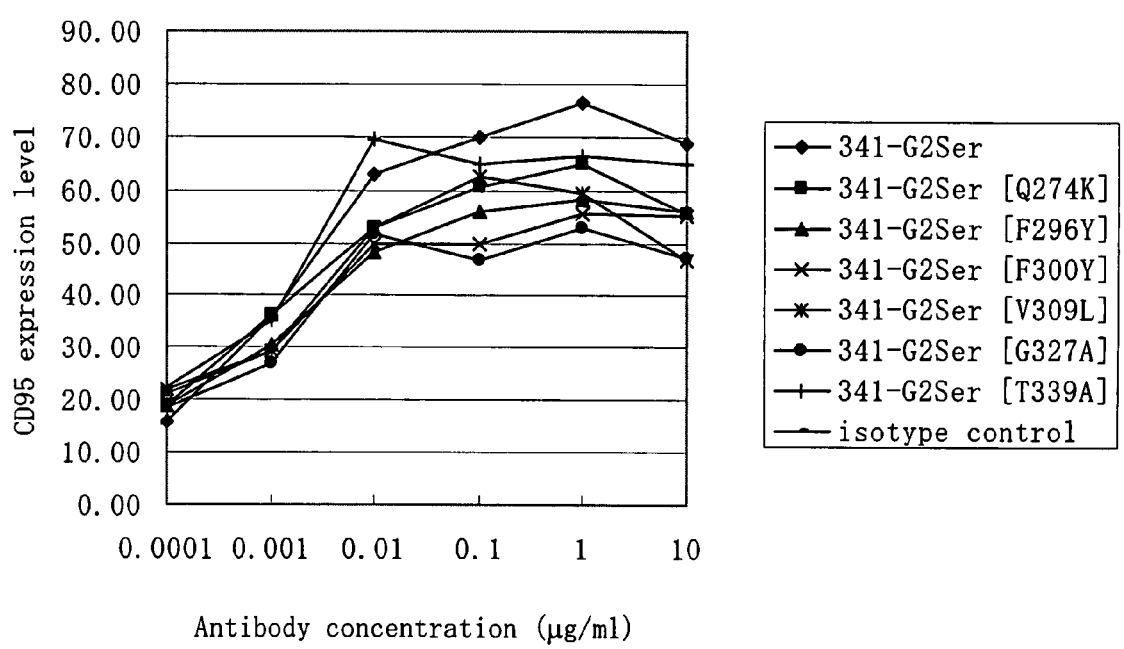
FIG. 2A is a diagram showing the promotion of CD95 expression in Ramos cells (CD95 expression-inducing activity for Ramos cells) by variants of an anti-CD40 antibody KM341-1-19.
Figure 2B:
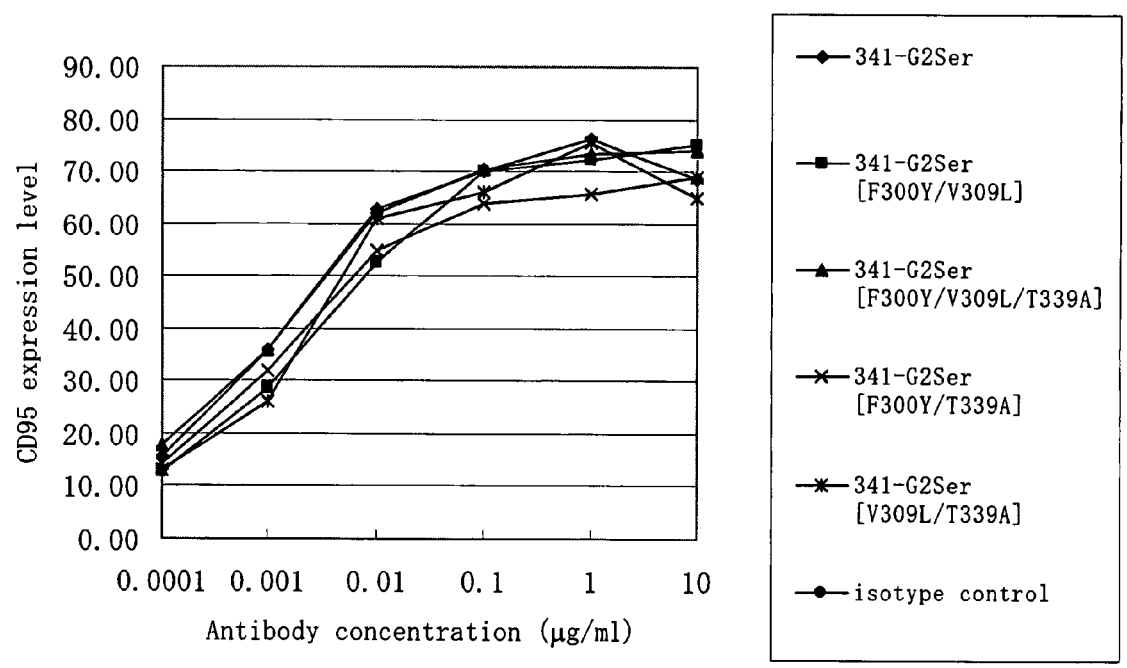
FIG. 2B is a diagram showing the promotion of CD95 expression in Ramos cells (CD95 expression-inducing activity for Ramos cells) by variants of an anti-CD40 antibody KM341-1-19.
Figure 2C:
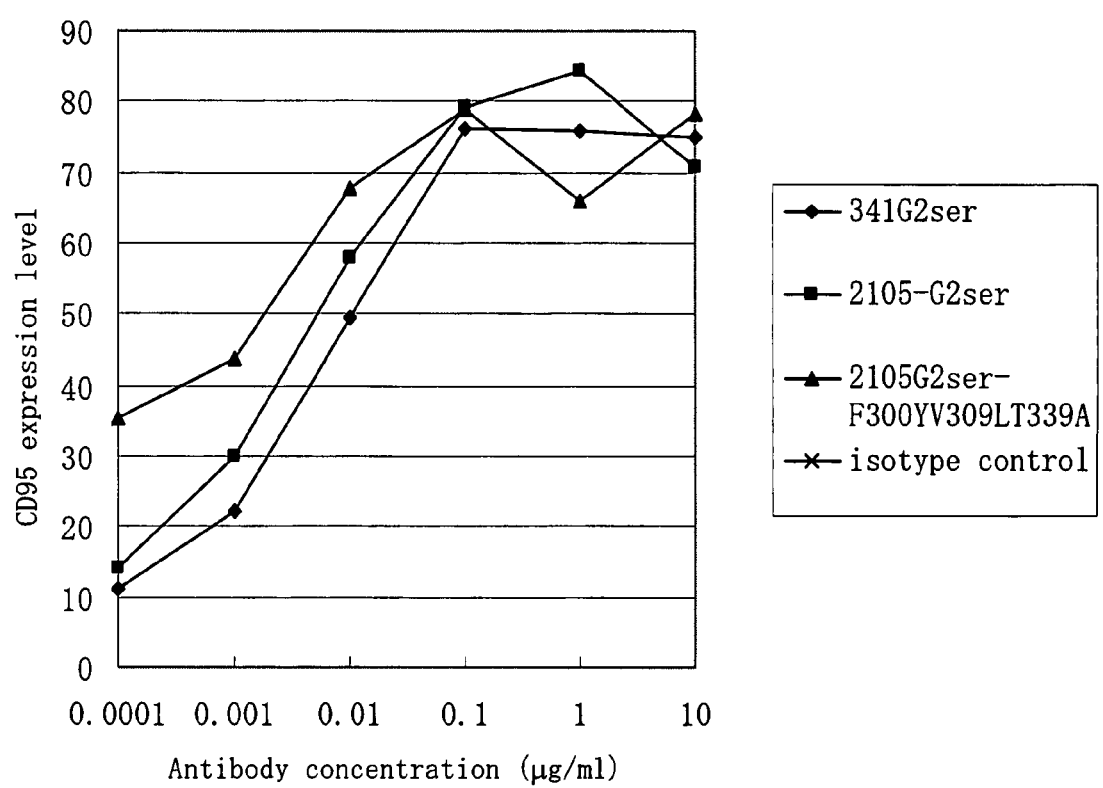
FIG. 2C is a diagram showing the promotion of CD95 expression in Ramos cells (CD95 expression-inducing activity for Ramos cells) by variants of anti-CD40 antibodies KM341-1-19 and 2105.

As a result, a change in antagonist activity of the antibodies attributed to the structural change of the constant region was not observed (FIGS. 2A, 2B, and 2C). In FIGS. 2A, 2B, and 2C, the unit of the CD95 expression level represented by the longitudinal axis is average fluorescence intensity. The values of the isotype control shown in FIGS. 2A, 2B, and 2C are 7.58, 7.58, and 6.29, respectively.

Example 12

Preparation of Anti-CD40 Antibodies Comprising Fused IgG1/IgG3 Constant Region

Antibodies were prepared by use of the light and heavy chain variable regions of a 4D11 antibody, of anti-CD40 antibodies described in WO 02/088186. These two antibodies have been shown to act as antagonists.

The 4D11 antibody is an antibody that is produced by a hybridoma 4D11, which has been deposited as Accession No. FERM BP-7758 on Sep. 27, 2001 with International Patent Organism Depositary, National Institute of Advanced Industrial Science and Technology (Central 6, 1-1-1, Higashi, Tsukuba, Ibaraki, Japan).

Nucleotide sequences encoding the heavy and light chain variable regions of the 4D11 antibody and amino acid sequences of the heavy and light chains are respectively shown below.

The boundary between the signal sequence and the variable region in the nucleic acid sequence (SEQ ID NO: 38) of the heavy chain of the 4D11 antibody is positioned between [cytosine] ([C]) at the 93rd position and cytosine (C) at the 94th position, while the boundary between the variable region and the constant region is positioned between adenine (A) at the 456th position and guanine (G) at the 457th position (examined with gene sequence prediction software Signal P ver. 2).

The boundary between the signal sequence and the variable region in the amino acid sequence (SEQ ID NO: 39) of the heavy chain of the 4D11 antibody is positioned between serine (S) at the 26th position and glutamine (Q) at the 27th position, while the boundary between the variable region and the constant region is positioned at serine (S) at the 147th position and alanine (A) at the 148th position.

Thus, the nucleic acid sequence of the heavy chain variable region of the 4D11 antibody reaches from cytosine (C) at the 94th position to adenine (A) at the 456th position in SEQ ID NO: 38. The amino acid sequence of the heavy chain variable region of the 4D11 antibody reaches from glutamine (Q) at the 27th position to serine (S) at the 147th position in SEQ ID NO: 39.

The boundary between the signal sequence and the variable region in the nucleic acid sequence (SEQ ID NO: 40) of the light chain of the 4D11 antibody is positioned between [thymine] ([T]) at the 124th position and guanine (G) at the 125th position, while the boundary between the variable region and the constant region is positioned between adenine (A) at the 442nd position and [cytosine] ([C]) at the 443rd position (examined with gene sequence prediction software Signal P ver. 2).

The boundary between the signal sequence and the variable region in the amino acid sequence (SEQ ID NO: 41) of the light chain of the 4D11 antibody is positioned between cysteine (C) at the 22nd position and alanine (A) at the 23rd position, while the boundary between the variable region and the constant region is positioned at lysine (K) at the 128th position and [arginine] ([R]) at the 129th position.

Thus, the nucleic acid sequence of the light chain variable region of the 4D11 antibody reaches from guanine (G) at the 125th position to adenine (A) at the 442nd position in SEQ ID NO: 40. The amino acid sequence of the light chain variable region of the 4D11 antibody reaches from alanine (A) at the 23rd position to lysine (K) at the 128th position in SEQ ID NO: 41.

```
4D11 heavy chain nucleotide sequence
                                         (SEQ ID NO: 38)
ATATGTCGACGAGTCATGGATCTCATGTGCAAGAAAATGAAGCACCTGTG

GTTCTTCCTCCTGCTGGTGGCGGCTCCCAGATGGGTCCTGTCCCAGCTGC

AGCTGCAGGAGTCGGGCCCAGGACTACTGAAGCCTTCGGAGACCCTGTCC

CTCACCTGCACTGTCTCTGGCGGCTCCATCAGCAGTCCTGGTTACTACGG

GGGCTGGATCCGCCAGCCCCAGGGAAGGGGCTGGAGTGGATTGGGAGTA

TCTATAAAAGTGGGAGCACCTACCACAACCCGTCCCTCAAGAGTCGAGTC

ACCATATCCGTAGACACGTCCAAGAACCAGTTCTCCCTGAAGCTGAGCTC

TGTGACCGCCGCAGACACGGCTGTGTATTACTGTACGAGACCTGTAGTAC

GATATTTTGGGTGGTTCGACCCCTGGGGCCAGGGAACCCTGGTCACCGTC

TCCTCAGCTAGC

4D11 heavy chain amino acid sequence
                                         (SEQ ID NO: 39)
MDLMCKKMKHLWFFLLLVAAPRWVLSQLQLQESGPGLLKPSETLSLTCTV

SGGSISSPGYYGGWIRQPPGKGLEWIGSIYKSGSTYHNPSLKSRVTISVD

TSKNQFSLKLSSVTAADTAVYYCTRPVVRYFGWFDPWGQGTLVTVSSAS

4D11 light chain nucleotide sequence
                                         (SEQ ID NO: 40)
AGATCTTAAGCAAGTGTAACAACTCAGAGTACGCGGGGAGACCCACTCAG

GACACAGCATGGACATGAGGGTCCCCGCTCAGCTCCTGGGGCTTCTGCTG

CTCTGGCTCCCAGGTGCCAGATGTGCCATCCAGTTGACCCAGTCTCCATC

CTCCCTGTCTGCATCTGTAGGAGACAGAGTCACCATCACTTGCCGGGCAA

GTCAGGGCATTAGCAGTGCTTTAGCCTGGTATCAGCAGAAACCAGGGAAA

GCTCCTAAGCTCCTGATCTATGATGCCTCCAATTTGGAAAGTGGGGTCCC

ATCAAGGTTCAGCGGCAGTGGATCTGGGACAGATTTCACTCTCACCATCA

GCAGCCTGCAGCCTGAAGATTTTGCAACTTATTACTGTCAACAGTTTAAT

AGTTACCCGACGTTCGGCCAAGGGACCAAGGTGGAAATCAAACGTACG

4D11 light chain amino acid sequence
                                         (SEQ ID NO: 41)
MDMRVPAQLLGLLLLWLPGARCAIQLTQSPSSLSASVGDRVTITCRASQG

ISSALAWYQQKPGKAPKLLIYDASNLESGVPSRFSGSGSGTDFTLTISSL

QPEDFATYYCQQFNSYPTFGQGTKVEIKRT
```

In order to identify a region in IgG1 involved in the suppression of aggregate formation at low pH by use of domain swap variant antibodies for IgG3 antibodies in the same way as IgG2 antibodies, domain swap variant antibodies IgG[1/1/3/3] ([1/1/3/3] refers to CH1, hinge, CH2, and CH3 domains in order from the left and means that the CH1 domain is derived from IgG1, the hinge domain is derived form IgG1, the CH2 domain is derived from IgG3, and the CH3 domain is derived from IgG3; hereinafter, interpreted in the same manner), IgG[3/3/1/1], IgG[3/3/1/3], and IgG[3/3/3/1] were prepared as described below.

To prepare IgG[1/1/3/3], N5KG1-Val Lark (IDEC Pharmaceuticals; hereinafter, abbreviated to N5KG1) was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and 13ch1-R: GTCTTCGTGGCTCACGTCCACCAC-CACGCA (SEQ ID NO: 42). At the same time, an antibody expression vector N5KG3 (IDEC Pharmaceuticals, U.S. Pat. No. 6,001,358; "G3" means that its heavy chain constant region is derived from IgG3; hereinafter, interpreted in the same manner) was used as a template to perform 15 cycles of reaction at 98° C. for 1 second, 60° C. for 30 seconds, and 72° C. for 30 seconds using primers 13ch1: TGCGTGGTGGTG-GACGTGAGCCACGAAGAC (SEQ ID NO: 43) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG1133.

To prepare IgG[3/3/1/1], N5KG3 was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and 13ch1-R: GTCTTCGTGGCTCACGTCCACCACCACGCA (SEQ ID NO: 42). At the same time, N5KG1 was used as a template to perform 15 cycles of reaction at 98° C. for 1 second, 60° C. for 30 seconds, and 72° C. for 30 seconds using primers 13ch1:

TGCGTGGTGGTGGACGTGAGCCACGAAGAC (SEQ ID NO: 43) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG3311.

To prepare IgG[3/3/1/3], the N5KG3311 thus prepared was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and CH3consR: GGTGTACACCTGTG-GCTCTCGGGGCTGCCC (SEQ ID NO: 13). At the same time, N5KG3 was used as a template to perform 15 cycles of reaction at 98° C. for 1 second, 60° C. for 30 seconds, and 72° C. for 30 seconds using primers CH3cons: GGGCAGC-CCCGAGAGCCACAGGTGTACACC (SEQ ID NO: 14) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG3313.

To prepare IgG[3/3/3/1], N5KG3 was used as a template to perform 15 cycles of reaction at 98° C. for 1 second, 60° C. for 30 seconds, and 72° C. for 30 seconds using primers linkH: gggtacgtcctcacattcagtgatcag (SEQ ID. NO: 9) and CH3consR: GGTGTACACCTGTGGCTCTCGGGGCT-GCCC (SEQ ID NO: 13). At the same time, N5KG1 was used as a template to perform 15 cycles of reaction at 98° C. for 1 second, 60° C. for 30 seconds, and 72° C. for 30 seconds using primers CH3cons: GGGCAGCCCCGAGAGCCACAGGT-GTACACC (SEQ ID NO: 14) and linkH2: tgatcatacgtagatat-cacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG3331.

Each of the expression vectors was digested with BglII and NheI, and the light and heavy chain variable regions of 4D11 were inserted thereinto to complete expression vectors.

Example 13

Expression and Purification of CD40 Antibodies of IgG3 and Measurement of Aggregate Contents of Purified Antibodies Each prepared expression vector DNA was expressed according to Example 2. The obtained culture supernatant (approximately 300 μg in terms of IgG) was charged onto an antibody purification affinity column HiTrap rProtein G HP (column volume of 1 ml) (Amersham Biosciences). After washing with PBS (−), the antibodies were eluted with 20 mM citric acid buffer (pH 2.7) and collected into a tube containing 200 mM phosphoric acid buffer (pH 7.0). Table 5 shows the aggregate content of each antibody sample after purification. The aggregate content of the 4D11-G3 antibody was 20% or more, whereas the domain swap variant antibodies (4D11-G[3311] and 4D11-G[3331]) comprising the CH3 domain of the constant region converted to IgG1 CH3 domain formed aggregates in a very small percentage and were found to be improved to the IgG1 level.

TABLE 5

| Purified antibody | Aggregate (%) |
|---|---|
| 4D11-G1 | 1.4 |
| 4D11-G3 | 23.4 |
| 4D11-G[1133] | 25.2 |
| 4D11-G[3311] | 0.0 |
| 4D11-G[3313] | 23.4 |
| 4D11-G[3331] | 0.0 |

Example 14

Evaluation of Stability of IgG3/IgG1 Domain Swap Variant Anti-CD40 Antibodies at Low pH Aggregate formation was shown to be remarkably suppressed in the 4D11-G[3331] after purification with the antibody purification affinity column. Therefore, for the purpose of further examining stability at low pH, the purified 4D11-G[3331] and 4D11-G[3311] domain swap variant antibodies of Example 13 were used and subjected to low-pH treatment according to Example 4. Then, aggregate contents were measured according to Example 3.

As a result, the 4D11-G[3311] domain swap variant antibody was shown to be as stable even under low-pH treatment conditions as or more stable than antibodies comprising the whole constant region derived from IgG1 (Table 6). Moreover, the 4D11-G[3331] exhibited a suppressed aggregate content of 3% or lower even after incubation treatment for 60 minutes and was confirmed to be stable at low pH. Table 6 shows the stability of the IgG3/IgG1 domain swap variant antibodies at low pH.

TABLE 6

| | Aggregate (%) | |
|---|---|---|
| Purified antibody | 10 min.* | 60 min.* |
| 4D11-G[3331] | 0.85 | 2.51 |
| 4D11-G[3311] | 0.00 | 0.72 |
| 4D11-G1 | 2.01 | 1.80 |

*Incubation time at low pH

Example 15

Preparation of One-amino Acid Variant Having One-amino Acid Variation in IgG3 CH3 Constant Region The analysis results using the domain swap variants demonstrated that mainly CH3 is involved in the aggregation formation of IgG3 in affinity purification using Protein G. Therefore, each variant comprising the IgG3 amino acid residue converted to an IgG1 amino acid residue (4D11-G3-[E356D] (the E residue at the 356th position was converted to D; hereinafter, interpreted in the same manner), 4D11-G3

[M358L], 4D11-G3[N392K], 4D11-G3[M397V], 4D11-G3 [I422V], and 4D11-G3-[R435H]) was prepared by focusing on 6 amino acid residues (at the 356th, 358th, 392nd, 397th, 422nd, and 435th positions designated by the EU index of Kabat et al.) different between IgG1 and IgG3 present within the CH3 domain.

To prepare IgG3-[E356D], N5KG3 was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and E356D-r: CTTGGTCATCTCATCCCGGGATGGGGG (SEQ ID NO: 44). At the same time, an antibody expression vector N5KG3 was used as a template to perform 15 cycles of reaction at 98° C. for 1 second, 60° C. for 30 seconds, and 72° C. for 30 seconds using primers E356D: CCCCCATCCCGG-GATGAGATGACCAAG (SEQ ID NO: 45) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG3-E356D.

To prepare IgG3[M358L], N5KG3 was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and M358L-r: CTGGTTCTTGGTCAGCTCCTCCCGGGA (SEQ ID NO: 46). At the same time, an antibody expression vector N5KG3 was used as a template to perform 15 cycles of reaction at 98° C. for 1 second, 60° C. for 30 seconds, and 72° C. for 30 seconds using primers M358L: TCCCGGGAG-GAGCTGACCAAGAACCAG (SEQ ID NO: 47) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG3-M358L.

To prepare IgG3[N392K], N5KG3 was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and N392K-r: GGGAGGCGTGGTCTTGTAGTTGTTCTC (SEQ ID NO: 48). At the same time, an antibody expression vector N5KG3 was used as a template to perform 15 cycles of reaction at 98° C. for 1 second, 60° C. for 30 seconds, and 72° C. for 30 seconds using primers N392K: GAGAACAACTA-CAAGACCACGCCTCCC (SEQ ID NO: 49) and linkH2: tgatcatacgtagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG3-N392K.

To prepare IgG3[I422V], N5KG3 was used as a template to perform 15 cycles of reaction at 98° C. for 1 second, 60° C. for 30 seconds, and 72° C. for 30 seconds using primers linkH: gggtacgtcctcacattcagtgatcag (SEQ ID NO: 9) and I422V-r: GGAGCATGAGAAGACGTTCCCCTGCTG (SEQ ID NO: 50). At the same time, an antibody expression vector N5KG3 was used as a template to perform 15 cycles of reaction at 98° C. for 1 second, 60° C. for 30 seconds, and 72° C. for 30 seconds using primers I422V: CAGCAGGGGAACGTCT-TCTCATGCTCC (SEQ ID NO: 51) and linkH2: tgatcatacg-tagatatcacggc (SEQ ID NO: 12). The amplified DNA fragments were purified with a PCR purification kit, and these two purified DNA fragments were mixed in equal amounts and then subjected to 5 cycles of reaction at 98° C. for 1 second, 60° C. for 30 seconds, and 72° C. for 30 seconds and additional 15 cycles of reaction with primers linkH and linkH2. The resulting amplified DNA fragment was cleaved with NheI and BamHI and substituted for the IgG1 constant region of an N5KG1 vector. This expression vector was designated as N5KG3-I422V.

To prepare IgG3[R435H], N5KG3 was used as a template to perform 30 cycles of reaction at 98° C. for 1 second, 60° C. for 30 seconds, and 72° C. for 30 seconds using primers linkH: gggtacgtcctcacattcagtgatcag (SEQ ID NO: 9) and R435H: CCCGGATCCTCATTTACCCGGAGACAGG-GAGAGGCTCTTCTGCGTGTAGTGGTTG TG (SEQ ID NO: 52). The amplified DNA fragment was cleaved with NheI and BamHI and substituted for the IgG1 constant region of an N5KG1 vector. This expression vector was designated as N5KG3-R435H.

Each of the expression vectors was digested with BglII and NheI, and the light and heavy chain variable regions of 4D11 were inserted thereinto to complete expression vectors.

To prepare 4D11-G3[M397V], the DNA of N5KG3-4D11 was used as a template to prepare variant DNA by the site-specific mutagenesis using GeneEditor™ in vitro Site-Directed Mutagenesis System (Promega) shown in Example 5. An oligonucleotide (5-terminally phosphorylated) for mutagenesis used was M397V: CACCACGCCT CCCGT-GCTGG ACTCCGAC (SEQ ID NO: 53). Candidate plasmid DNA of the variant antibody expression vector obtained by the site-specific mutagenesis was selected by DNA nucleotide sequence analysis to obtain an expression vector of a variant having the amino acid variation of interest introduced therein. This expression vector was designated as N5KG3-M397V.

Example 16

Evaluation of Suppression of Aggregate Formation of 4D11-G3 Variants

Each variant comprising the IgG3 amino acid residue converted to an IgG1 amino acid residue (4D11-G3[E356D], 4D111-G3[M358L], 4D11-G3[N392K], 4D11-G3[M397V], 4D11-G3[I422V], and 4D11-G3-[R435H]) was expressed from each expression vector DNA of according to Example 2. The antibodies were purified from the obtained culture supernatant (approximately 500 μg in terms of IgG) according to Example 13. Table 7 shows the aggregate content of each antibody sample after purification. As shown in Table 7, the 4D11-G[N392K] and 4D11-G[M397V] were found to form aggregates in a decreased percentage (approximately 10%), whereas the 4D11-G3 antibody and other one-amino acid residue variants exhibited an aggregate content of 20% or higher.

TABLE 7

| Purified antibody | Aggregate (%) |
| --- | --- |
| 4D11-G1 | 1.4 |
| 4D11-G3 | 24.7 |
| 4D11-G[3331] | 0.0 |
| 4D11-G3[E356D] | 23.6 |
| 4D11-G3[M358L] | 23.4 |
| 4D11-G3[N392K] | 12.4 |
| 4D11-G3[M397V] | 7.2 |
| 4D11-G3[I422V] | 27.7 |
| 4D11-G3[R435H] | 25.1 |

Example 17

Evaluation of Suppression of Aggregate Formation of 4D11-G3 Variants (2)

As shown in Example 16, the variants (4D11-G3[N392K] and 4D11-G3[M397V]) whose aggregate formation was partially suppressed were found from the study using the variants of the IgG3 antibody having an one-amino acid substitution in the constant region. Therefore, for the purpose of further enhancing the effect of suppressing aggregate formation, a variant (4D11-G3[N392KM397V]) having both of these two amino acid variations was prepared. A method for the variant expression vector preparation was performed according to the site-specific mutagenesis of Example 5 using GeneEditor™ in vitro Site-Directed Mutagenesis System (Promega). An oligonucleotide (5'-terminally phosphorylated) for mutagenesis used was N392KM397V: GGGCAGCCGG AGAACAACTA CAAGACCACG CCTCCCGTGC TGGACTCCGA CGGCTCC (SEQ ID NO: 54). Candidate plasmid DNA of the obtained variant antibody expression vector was selected by DNA nucleotide sequence analysis to obtain an expression vector of an anti-CD40 antibody variant having the amino acid variation of interest introduced therein. The plasmid DNA expressing the anti-CD40 antibody variant protein was designated as N5KG3-4D11-N392KM397V.

Example 18

Evaluation of Suppression of Aggregate Formation of 4D11-G3 Variants (3)

In Examples 13 and 14, it could be confirmed that a substitution of the CH3 domain of an IgG1 heavy chain for the CH3 domain of the IgG3 heavy chain or the CH2 and CH3 domains of an IgG1 heavy chain for the CH2 and CH3 domains of the IgG3 heavy chain can improve antibody stability. Therefore, to further narrow down candidate amino acid residues contributing to the suppression of aggregate formation, each variant comprising the 4D11-G[3331] amino acid residue converted to an IgG1 amino acid residue was prepared by further focusing on two amino acid residues (at the 300th and 309th positions designated by the EU index of Kabat et al.) shown to be involved in the suppression of aggregate formation of IgG2 shown in Example 6, among the amino acid residues different between IgG1 and IgG3 present within the CH2 domain of the IgG3 antibody. The prepared variants were 3 kinds: 4D11-G[3331][F300Y] (the amino acid residue F at the 300th position of the domain swap variant 4D11-G[3331] was converted to Y; hereinafter, interpreted in the same manner), 4D11-G[3331][T339A], and 4D11-G[3331][F300YT339A] (F at the 300th position was converted to Y, and T at the 339th position was converted to A). A method for the variant expression vector preparation was performed according to the site-specific mutagenesis of Example 5 using GeneEditor™ in vitro Site-Directed Mutagenesis System (Promega) except that for the 4D11-G[3331][F300YT339A], two oligonucleotides were simultaneously annealed to the template vector DNA. The oligonucleotides for mutagenesis used were G3_F300Y: CAGTACAACA GCACGTACCG TGTGGTCAGC (SEQ ID NO: 55) for 4D11-G[3331][F300Y] preparation, G3_T339A: GAAAACCATC TCCAAAGCCA AAGGACAGCC C (SEQ ID NO: 56) for 4D11-G[3331][T339A] preparation, and G3_F300Y and G3_T339A for 341-G2Ser [V309L/T339A] preparation. Candidate plasmid DNA of each variant antibody expression vector obtained by the site-specific mutagenesis shown in Example 5 was selected by DNA nucleotide sequence analysis to obtain expression vectors of 3 kinds of anti-CD40 antibody variants having the amino acid variation of interest introduced therein. The plasmid DNAs expressing these anti-CD40 antibody variant proteins were respectively designated as N5KG[3331]-4D11-F300Y, N5KG[3331]-4D11-T339A, and N5KG[3331]-4D11-F300YT339A.

Example 19

Expression and Purification of Amino Acid Substitution Variant Antibodies and Measurement of Aggregate Content of Purified Antibodies The expression vector DNAs prepared in Examples 17 and 18 were expressed according to Example 2. The antibodies were purified from the obtained culture supernatant (approximately 300 µg in terms of IgG) by use of the antibody purification affinity column HiTrap rProtein G HP shown in Example 13. Table 8 shows the aggregate content of each antibody sample after purification. The 4D11-G3 antibody exhibited an aggregate content of approximately 30%, whereas any of the variants formed no detected aggregate.

TABLE 8

| Purified antibody | Aggregate (%) |
| --- | --- |
| 4D11-G3 | 29.7 |
| 4D11-G3[N392KM397V] | 0.0 |
| 4D11-G[3331][F300Y] | 0.0 |
| 4D11-G[3331][T339A] | 0.0 |
| 4D11-G[3331][F300YT339A] | 0.0 |

Example 20

Evaluation of Stability of Amino Acid Substitution Variant Antibodies at Low pH

The stability of the 3 kinds of variants of the 4D11-G[3331] having an amino acid substitution in the CH2 domain at low pH was confirmed. The purified antibodies of Example 19 were used and subjected to low-pH treatment according to Example 4. Aggregate contents were measured according to Example 3.

As a result, the amino acid substitution variants of the 4D11-G[3331] exhibited suppressed aggregate formation not only after purification but also under low-pH treatment conditions and were confirmed to be improved in stability. Table 9 shows the stability of the IgG3/IgG1 domain swap variant antibodies at low pH.

TABLE 9

| Purified antibody | Aggregate (%) | |
|---|---|---|
| | 10 min.* | 60 min.* |
| 4D11-G[3311] | 0.00 | 0.00 |
| 4D11-G[3331][F300Y] | 0.00 | 0.00 |
| 4D11-G[3331][T339A] | 0.00 | 1.78 |
| 4D11-G[3331][F300YT339A] | 0.00 | 0.00 |

*Incubation time at low pH

Example 21

Preparation of Amino Acid Variants Having Amino Acid Variation in Constant Region of IgG3

Taking, into consideration in comprehensive manners, the analysis results of improvement in the stability of the IgG3/IgG1 domain swap variant antibodies and various kinds of amino acid variants, 4D11-G3[N392KM397V][R435H] and 4D11-G3[F300Y][N392KM397V][R435H] were prepared and evaluated as antibodies capable of improving IgG3 antibody stability most. The 4D11-G3[N392KM397V][R435H] is a three-amino acid residue variant comprising the amino acid residue N at the 392nd position of the IgG3 antibody converted to K, the amino acid residue M at the 397th position converted to V, and the amino acid residue R at the 435th position converted to H. Alternatively, the 4D11-G3[F300Y][N392KM397V][R435H] is a four-amino acid residue variant comprising 4D11-G3[N392KM397V][R435H] and additionally comprising the amino acid residue F at the 300th position converted to Y. However, in both the variants, the amino acid residue variation R435H was introduced to permit for the purification of the antibody proteins with Protein A (Ito S et al., Exp Clin Immunogenet. 1990, 7 (2): 91-100). A method for the variant expression vector preparation was performed according to the site-specific mutagenesis of Example 5 using GeneEditor™ in vitro Site-Directed Mutagenesis System (Promega) except that the N5KG3-R435H expression vector DNA shown in Example 12 was used as a template. Oligonucleotides for mutagenesis used were N392KM397V: GGGCAGCCGG AGAACAACTA CAAGACCACG CCTCCCGTGC TGGACTCCGA CGGCTCC (SEQ ID NO: 57) for 4D11-G3[N392KM397V][R435H] preparation and several oligonucleotides G3_F300Y: CAGTACAACA GCACGTACCG TGTGGTCAGC (SEQ ID NO: 58) and N392KM397V simultaneously annealed to the template vector DNA for 4D11-G3[F300Y][N392KM397V][R435H] preparation. Candidate plasmid DNA of each variant antibody expression vector obtained by the site-specific mutagenesis shown in Example 5 was selected by DNA nucleotide sequence analysis to obtain expression vectors of 2 kinds of anti-CD40 antibody variants having the amino acid variation of interest introduced therein. The plasmid DNAs expressing these anti-CD40 antibody variant proteins were respectively designated as N5KG3-4D11-[N392KM397V][R435H] and N5KG3-4D11-[F300Y][N392KM397V][R435H].

A nucleotide sequence encoding the heavy chain of the 4D11-G3[F300Y][N392KM397V][R435H] and an amino acid sequence of the heavy chain are shown below.

4D11-G3[F300Y][N392KM397V][R435H] heavy chain
nucleotide sequence
(SEQ ID NO: 59)
ATGGATCTCATGTGCAAGAAAATGAAGCACCTGTGGTTCTTCCTCCTGCT

GGTGGCGGCTCCCAGATGGGTCCTGTCCCAGCTGCAGCTGCAGGAGTCGG

GCCCAGGACTACTGAAGCCTTCGGAGACCCTGTCCCTCACCTGCACTGTC

TCTGGCGGCTCCATCAGCAGTCCTGGTTACTACGGGGGCTGGATCCGCCA

GCCCCCAGGGAAGGGGCTGGAGTGGATTGGGAGTATCTATAAAAGTGGGA

GCACCTACCACAACCCGTCCCTCAAGAGTCGAGTCACCATATCCGTAGAC

ACGTCCAAGAACCAGTTCTCCCTGAAGCTGAGCTCTGTGACCGCCGCAGA

CACGGCTGTGTATTACTGTACGAGACCTGTAGTACGATATTTTGGGTGGT

TCGACCCCTGGGGCCAGGGAACCCTGGTCACCGTCTCCTCAGCTAGCACC

AAGGGCCCATCGGTCTTCCCCCTGGCGCCCTGCTCCAGGAGCACCTCTGG

GGGCACAGCGGCCCTGGGCTGCCTGGTCAAGGACTACTTCCCCGAACCGG

TGACGGTGTCGTGGAACTCAGGCGCCCTGACCAGCGGCGTGCACACCTTC

CCGGCTGTCCTACAGTCCTCAGGACTCTACTCCCTCAGCAGCGTGGTGAC

CGTGCCCTCCAGCAGTTTGGGCACCCAGACCTACACCTGCAACGTGAATC

ACAAGCCCAGCAACACCAAGGTGGACAAGAGAGTTGAGCTCAAAACCCCA

CTTGGTGACACAACTCACACATGCCCACGGTGCCCAGAGCCCAAATCTTG

TGACACACCTCCCCCGTGCCCACGGTGCCCAGAGCCCAAATCTTGTGACA

CACCTCCCCCATGCCCACGGTGCCCAGAGCCCAAATCTTGTGACACACCT

CCCCCGTGCCCAAGGTGCCCAGCACCTGAACTCCTGGGAGGACCGTCAGT

CTTCCTCTTCCCCCCAAAACCCAAGGATACCCTTATGATTTCCCGGACCC

CTGAGGTCACGTGCGTGGTGGTGGACGTGAGCCACGAAGACCCCGAGGTC

CAGTTCAAGTGGTACGTGGACGGCGTGGAGGTGCATAATGCCAAGACAAA

GCTGCGGGAGGAGCAGTACAACAGCACGTACCGTGTGGTCAGCGTCCTCA

CCGTCCTGCACCAGGACTGGCTGAACGGCAAGGAGTACAAGTGCAAGGTC

TCCAACAAAGCCCTCCCAGCCCCCATCGAGAAAACCATCTCCAAAACCAA

AGGACAGCCCCGAGAACCACAGGTGTACACCCTGCCCCCATCCCGGGAGG

AGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAA

CTACAAGACCACGCCTCCCGTGCTGGACTCCGACGGCTCCTTCTTCCTCT

ACAGCAAGCTCACCGTGGACAAGAGCAGGTGGCAGCAGGGGAACATCTTC

TCATGCTCCGTGATGCATGAGGCTCTGCACAACCACTACACGCAGAAGAG

CCTCTCCCTGTCTCCGGGTAAATGA

The boundary between the signal sequence and the variable region in SEQ ID NO: 59 is positioned between cytosine (C) at the 78th position and cytosine (C) at the 79th position (examined with gene sequence prediction software Signal P ver. 2).

4D11-G3[F300Y][N392KM397V][R435H] heavy chain
amino acid sequence
(SEQ. ID NO: 60)
MDLMCKKMKHLWFFLLLVAAPRWVLSQLQLQESGPGLLKPSETLSLTCTV

SGGSISSPGYYGGWIRQPPGKLEWIGSIYKSGSTYHNPSLKSRVTISVDT

SKNQFSLKLSSVTAADTAVYYCTRPVVRYFGWFDPWGQGTLVTVSSASTK

GPSVFPLAYCSRSTSGGTAALGCLVKDYFPEPVTVSWNSGALTSGVHTFP

AVLQSSGLYSLSSVVTVPSSSLGTQTYTCNVNHKPSNTKVDKRVELKTPL

-continued
GDTTHTCPRCPEPKSCDTPPPCPRCPEPKSCDTPPPCPRCPEPKSCDTPP

PCPRCPAPELLGGPSVFLFPPKPKDTLMISRTPEVTCVVVDVSHEDPEVQ

FKWYVDGVEVHNAKTKLREEQYNSTYRVVSVLTVLHQDWLNGKEYKCKVS

NKALPAPIEKTISKTKGQPREPQVYTLPPSREEMTKNQVSLTCLVKGFYP

SDIAVEWESNGQPENNYKTTPPVLDSDGSFFLYSKLTVDKSRWQQGNIFS

CSVMHEALHNHYTQKSLSLSPGK

The boundary between the signal sequence and the variable region in SEQ ID NO: 60 is positioned between serine (S) at the 26th position and glutamine (Q) at the 27th position (examined with gene sequence prediction software Signal P ver. 2).

A nucleotide sequence encoding the light chain of the 4D11-G3[F300Y][N392KM397V][R435H] and an amino acid sequence of the heavy chain are shown below.

```
4D11-G3[F300Y][N392KM397V][R435H] light chain
nucleotide sequence
                                    (SEQ ID NO: 61)
ATGGACATGAGGGTCCCCGCTCAGCTCCTGGGGCTTCTGCTGCTCTGGCT

CCCAGGTGCCAGATGTGCCATCCAGTTGACCCAGTCTCCATCCTCCCTGT

CTGCATCTGTAGGAGACAGAGTCACCATCACTTGCCGGGCAAGTCAGGGC

ATTAGCAGTGCTTTAGCCTGGTATCAGCAGAAACCAGGGAAAGCTCCTAA

GCTCCTGATCTATGATGCCTCCAATTTGGAAAGTGGGGTCCCATCAAGGT

TCAGCGGCAGTGGATCTGGGACAGATTTCACTCTCACCATCAGCAGCCTG

CAGCCTGAAGATTTTGCAACTTATTACTGTCAACAGTTTAATAGTTACCC

GACGTTCGGCCAAGGGACCAAGGTGGAAATCAAACGTACGGTGGCTGCAC

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAAGCAGACTACGAGAAACACAAAGTCTACGCCTGCGAAGT

CACCCATCAGGGCCTGAGCTCGCCCGTCACAAAGAGCTTCAACAGGGGAG

AGTGTTGA
```

The boundary between the signal sequence and the variable region in SEQ ID NO: 61 is positioned between thymine (T) at the 66th position and guanine (G) at the 67th position (examined with gene sequence prediction software Signal P ver. 2).

```
4D11-G3[F300Y][N392KM397V][R435H] light chain
amino acid sequence
                                    (SEQ ID NO: 62)
MDMRVPAQLLGLLLLWLPGARCAIQLTQSPSSLSASVGDRVTITCRASQG

ISSALAWYQQKPGKAPKLLIYDASNLESGVPSRFSGSGSGTDFTLTISSL

QPEDFATYYCQQFNSYPTFGQGTKVEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC
```

The boundary between the signal sequence and the variable region in SEQ ID NO: 62 is positioned between cysteine (C) at the 22nd position and alanine (A) at the 23rd position (examined with gene sequence prediction software Signal P ver. 2).

Example 22

Evaluation of Suppression of Aggregate Formation of Purified 4D1'-G3 [N392KM397V] [R435H] and 4D11-G3 [F300Y][N392KM397V][R435H] Antibodies The expression vector DNAs of the 4D11-G3 [N392KM397V][R435H] and 4D11-G3[F300Y] [N392KM397V][R435H] were expressed according to Example 2. The antibodies were purified from the obtained culture supernatant (approximately 400 μg in terms of IgG) by the method shown in Example 2 by use of HiTrap rProtein A FF. Table 10 shows the aggregate content of each antibody sample after purification. As shown in Examples 10 and 13, the 4D11-G3 antibody exhibited an aggregate content of 20% or higher, whereas these variants exhibited an aggregate content decreased to the same level (1% or lower) as the IgG1 antibody and were found to exhibit significantly suppressed aggregate formation.

TABLE 10

| Purified antibody | Aggregate (%) |
|---|---|
| 4D11-G1 | 0.84 |
| 4D11-G[3311] | 0.00 |
| 4D11-G[3331] | 0.30 |
| 4D11-G3[N392KM397V][R435H] | 0.00 |
| 4D11-G3[F300Y][N392KM397V][R435H] | 0.44 |

Example 23

Evaluation of Stability of 4D11-G3[N392KM397V][R435H] and 4D11-G3[F300Y][N392KM397V][R435H] Antibodies at low pH The stability of the 4D11-G3-[N392KM397V][R435H] and 4D11-G3[F300Y][N392KM397V][R435H] antibodies at low pH was confirmed. The purified antibodies of Example 15 were used and subjected to low-pH treatment according to Example 4. Aggregate contents were measured according to Example 3.

As a result, these amino acid substitution variants exhibited suppressed aggregate formation not only after purification but also under low-pH treatment conditions and were confirmed to be improved in stability. Table 11 shows the stability of the IgG3/IgG1 domain swap variant antibodies at low pH.

TABLE 11

| | Aggregate (%) | |
|---|---|---|
| Purified antibody | 10 min.* | 60 min.* |
| 4D11-G1 | 0.13 | 0.00 |
| 4D11-G[3311] | 0.00 | 0.00 |
| 4D11-G[3331] | 0.79 | 3.79 |
| 4D11-G3[N392KM397V][R435H] | 0.00 | 1.50 |
| 4D11-G3[F300Y][N392KM397V][R435H] | 0.00 | 0.00 |

*Incubation time at low pH

Example 24

Avidity of Anti-CD40 Antibodies to Ramos Cells

To examine whether the domain swap variant and one-amino acid substitution variant antibodies prepared in Examples 12 and 13 exhibit binding activity at the same level as their original antibodies, the binding activity to Ramos [ATCC] cells expressing CD40 was measured.

Ramos cell lines were suspended at a concentration of $2×10^6$ cells/ml in a staining buffer (SB) of PBS containing 0.1% $NaN_3$ and 2% FCS. The cell suspension (100 μl/well) was dispensed into a 96-well round-bottomed plate (manufactured by Becton, Dickinson and Company). The culture supernatant (50 μl) of each hybridoma was added to the plate and incubated at an ice temperature for 30 minutes. A human IgG1 antibody against human serum albumin was used as a negative control and adjusted to a concentration of 2 μg/ml with a hybridoma culture medium. A 50 μl aliquot thereof was added to the plate and incubated at an ice temperature for 15 minutes. After washing with SB, 50 μl of an R-PE fluorescently labeled anti-human antibody (manufactured by Southern Biotechnology) diluted 250 folds was added thereto and incubated at an ice temperature for 15 minutes. After washing two times with SB, the cells were suspended in 300 to 500 μl of FACS buffer solution. The fluorescence intensity of each cell was measured with FACS (FACSort, FACScan, manufactured by Becton, Dickinson and Company).

Figure 3:
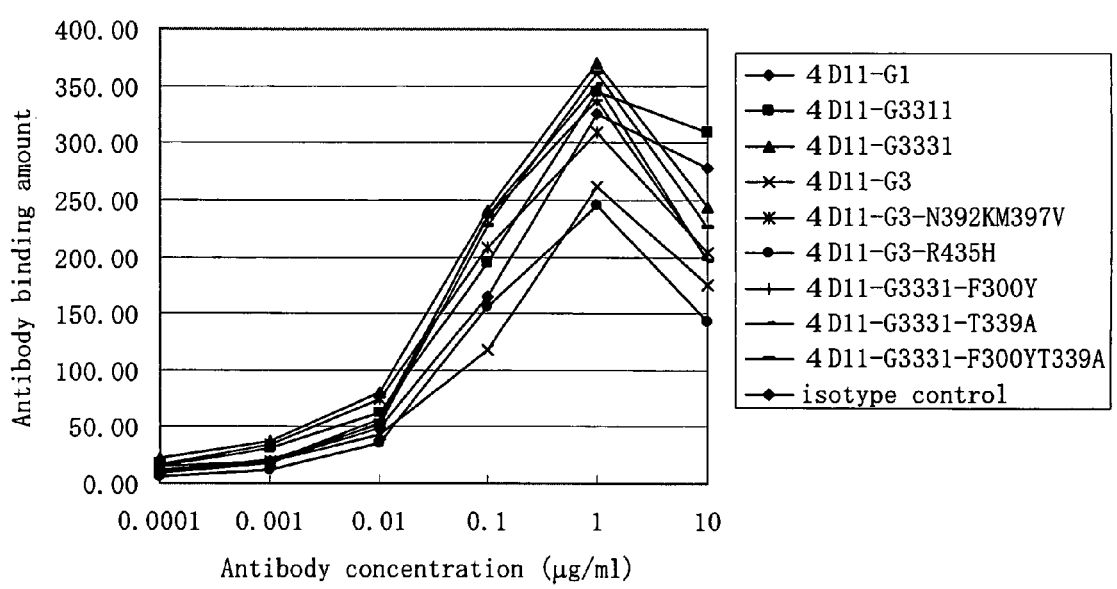
FIG. 3 is a diagram showing the binding activity of variants of an anti-CD40 antibody 4D11 to Ramos cells (Ramos cell binding activity)

As a result, difference in binding property was not observed among the domain swap variant antibodies and the variant antibodies (FIG. 3). In FIG. 3, the unit of the antibody binding amount represented by the longitudinal axis is average fluorescence intensity. The value of the isotype control is 5.01.

Example 25

Suppression of CD95 Expression in Ramos Cells by Anti-CD40 Antibodies

4D11 and KM281-1-10 are known to be antagonist antibodies. The influence of the structural change of the constant regions of antibodies on their antagonist activity was examined. Ramos cells have been observed to have increases in CD95 expression by the addition of CD40 ligands. The antagonist activity of the antibodies was examined by using, as an index, whether the addition of the antibodies can suppress increases in CD95 expression.

A Ramos cell suspension with a concentration of $10×10^6$ cells/ml was inoculated at a concentration of 50 μl/well onto a 96-well plate. The culture supernatant or the purified antibody was adjusted with a medium to a concentration of 2 μg/ml and added at a concentration of 100 μl/well to the 96-well plate. A soluble CD40 ligand (ALEXIS CORPORATION) and an anti-FLAG antibody (M2, Sigma) were added at a concentration of 4 μg/ml each to a medium, which was then added at a concentration of 50 μl/well to the 96-well plate. After overnight culture, the cells were collected and analyze with FACS using an R-PE labeled anti-CD95 antibody (Pharmingen NJ).

Figure 4:
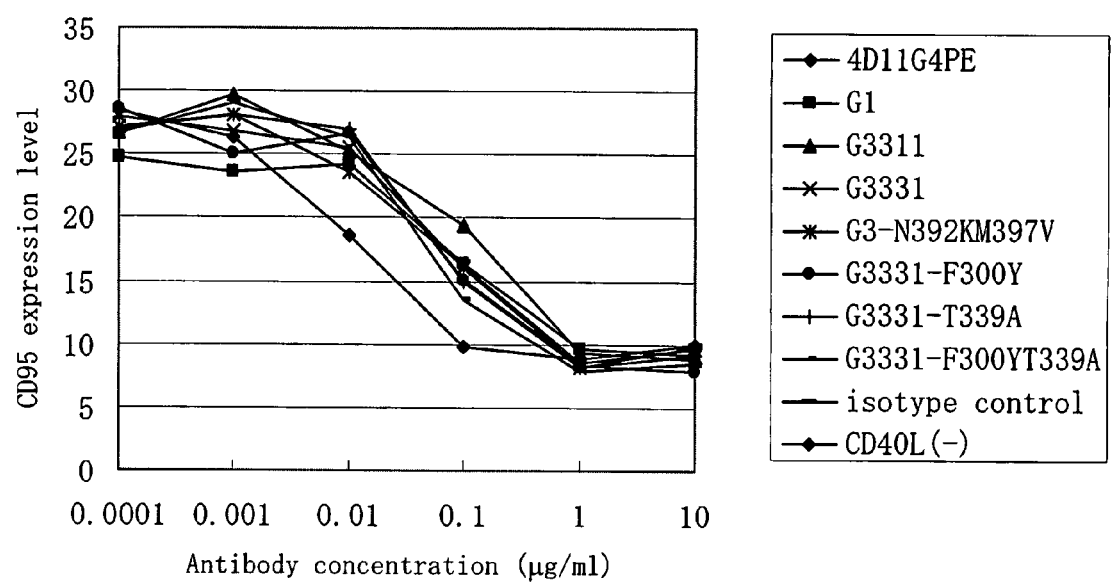
FIG. 4 is a diagram showing the suppression of CD95 expression in Ramos cells (antagonist activity evaluation) by variants of an anti-CD40 antibody 4D11.

As a result, a change in antagonist activity of the antibodies attributed to the structural change of the constant region was not observed (FIG. 4). In FIG. 4, the unit of the CD95 expression level represented by the longitudinal axis is average fluorescence intensity. The values of the isotype control and CD40 (−) are 27.17 and 6.59, respectively.

A human IgG3 heavy chain constant region has polymorphisms and comprises a consensus sequence described below. The present invention also encompasses an antibody having the heavy chain constant region with the consensus sequence below (SEQ ID NO: 63) to which the variations of the present invention is applied. In the sequence below, a variation can be caused in, for example, underlined F at the 300th position, T at the 399th position, N at the 392nd position, M at the 397th position, and R at the 435th position to thereby obtain the stabilized antibody of the present invention.

ASTKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVEL

KTPLGDTTHTCPRCPEPKSCDTPPPCPRCPEPKSCDTPPPCPRCPEPKSC

DTPPPCPRCPAPELLGGPSVFLFPPKPKDTLMISRTPEVTCVVVDVSHED

PEVQFKWYVDGVEVHNAKTKPREEQYNST<u>F</u>RVVSVLTVLHQDWLNGKEYK

CKVSNKALPAPIEKTISK<u>T</u>KGQPREPQVYTLPPSREEMTKNQVSLTCLVK

GFYPSDIAVEWESSGQPENNY<u>N</u>TTPP<u>M</u>LDSDGSFFLYSKLTVDKSRWQQG

NIFSCSVMHEALHN<u>R</u>FTQKSLSLSPGK

All publications, patents, and patent applications cited herein are incorporated herein by reference in their entirety.

Free text for sequence listing SEQ ID NOS: 9 to 14, 23 to 29, and 42 to 58: primer

The invention claimed is:

1. An isolated and non-naturally occurring IgG heavy chain comprising the constant region of a human IgG2 heavy chain having at least a substitution of Y for F at the 300th position designated by the EU index as defined by Kabat.

2. An isolated and non-naturally occurring IgG heavy chain comprising the constant region of a human IgG2 heavy chain having at least a substitution of L for V at the 309th position designated by the EU index as defined by Kabat.

3. An isolated and non-naturally occurring IgG heavy chain comprising the constant region of a human IgG2 heavy chain having at least a substitution of A for T at the 339th position designated by the EU index as defined by Kabat.

4. A method for producing an IgG antibody, comprising the step of substituting Y for F at the 300th position designated by the EU index as defined by Kabat in the constant region of a human IgG2 heavy chain.

5. A method for producing an IgG heavy chain, comprising the step of substituting L for V at the 309th position designated by the EU index as defined by Kabat in the constant region of a human IgG2 heavy chain.

6. A method for producing an IgG antibody, comprising the step of substituting A for T at the 339th position designated by the EU index as defined by Kabat in the constant region of a human IgG2 heavy chain.

7. A method for producing a monoclonal antibody, comprising a production method according to any one of claims 4 to 6.

8. A method for producing a monoclonal antibody, comprising the step of: culturing, in a culture solution, a host comprising an expression vector having polynucleotides encoding the heavy and light chains of the IgG antibody according to any one of claims 1-3; and obtaining a monoclonal antibody from the resulting cultures and/or the host.

9. A method for suppressing monoclonal antibody aggregation, characterized by comprising substituting Y for F at the 300th position designated by the EU index as defined by Kabat in the constant region of a human IgG2 heavy chain.

10. A method for suppressing monoclonal antibody aggregation, characterized by comprising substituting L for V at the 309th position designated by the EU index as defined by Kabat in the constant region of a human IgG2 heavy chain.

11. A method for suppressing monoclonal antibody aggregation, characterized by comprising substituting A for T at the 339th position designated by the EU index as defined by Kabat in the constant region of a human IgG2 heavy chain.

12. An isolated and non-naturally occurring IgG heavy chain comprising the constant region of a human IgG3 heavy chain having at least a substitution of V for M at the 397th position designated by the EU index as defined by Kabat.

13. A method for producing an IgG heavy chain, comprising the step of substituting K for N at the 392nd position designated by the EU index as defined by Kabat in the constant region of a human IgG3 heavy chain.

14. A method for producing an IgG antibody, comprising the step of substituting V for M at the 397th position designated by the EU index as defined by Kabat in the constant region of a human IgG3 heavy chain.

15. A method for producing a monoclonal antibody, comprising a production method according to claim 13.

16. A method for producing a monoclonal antibody, comprising the step of: culturing, in a culture solution, a host comprising an expression vector having polynucleotides encoding the heavy and light chains of a monoclonal antibody according to claim 12; and obtaining a monoclonal antibody from the resulting cultures and/or the host.

17. A method for suppressing monoclonal antibody aggregation, characterized by comprising substituting K for N at the 392nd position designated by the EU index as defined by Kabat in the constant region of a human IgG3 heavy chain.

18. A method for suppressing monoclonal antibody aggregation, characterized by comprising substituting V for M at the 397th position designated by the EU index as defined by Kabat in the constant region of a human IgG3 heavy chain.

19. An antibody comprising the constant region of a human IgG3 heavy chain according to claim 12, wherein the antibody is a monoclonal antibody.

20. A method for producing a monoclonal antibody, comprising a production method according to claim 14.

* * * * *

UNITED STATES PATENT AND TRADEMARK OFFICE
CERTIFICATE OF CORRECTION

PATENT NO. : 8,716,451 B2
APPLICATION NO. : 11/794950
DATED : May 6, 2014
INVENTOR(S) : Nobuaki Takahashi and Hideaki Yoshida It is certified that error appears in the above-identified patent and that said Letters Patent is hereby corrected as shown below:

In the claims

Column 145, lines 60-63 (Claim 1),

"1. An isolated and non-naturally occurring IgG heavy chain comprising the constant region of a human IgG2 heavy chain having at least a substitution of Y for F at the 300th position designated by the EU index as defined by Kabat.", should be -- 1. An isolated and non-naturally occurring IgG antibody comprising the constant region of a human IgG2 heavy chain having at least a substitution of Y for F at the 300th position designated by the EU index as defined by Kabat. --.

Column 145, lines 64-67 (Claim 2),

"2. An isolated and non-naturally occurring IgG heavy chain comprising the constant region of a human IgG2 heavy chain having at least a substitution of L for V at the 309th position designated by the EU index as defined by Kabat.", should be -- 2. An isolated and non-naturally occurring IgG antibody comprising the constant region of a human IgG2 heavy chain having at least a substitution of L for V at the 309th position designated by the EU index as defined by Kabat. --.

Column 146, lines 60-63 (Claim 3),

"3. An isolated and non-naturally occurring IgG heavy chain comprising the constant region of a human IgG2 heavy chain having at least a substitution of A for T at the 339th position designated by the EU index as defined by Kabat.", should be Signed and Sealed this
Twelfth Day of April, 2016

Michelle K. Lee
*Director of the United States Patent and Trademark Office*

-- 3. An isolated and non-naturally occurring IgG antibody comprising the constant region of a human IgG2 heavy chain having at least a substitution of A for T at the 339th position designated by the EU index as defined by Kabat. --.

Column 147, line 31 to Column 148, line 2 (Claim 12),

"12. An isolated and non-naturally occurring IgG heavy chain comprising the constant region of a human IgG3 heavy chain having at least a substitution of V for M at the 397th position designated by the EU index as defined by Kabat.", should be -- 12. An isolated and non-naturally occurring IgG antibody comprising the constant region of a human IgG3 heavy chain having at least a substitution of V for M at the 397th position designated by the EU index as defined by Kabat. --.